United States Patent [19]
Pastan et al.

[11] Patent Number: 6,011,002
[45] Date of Patent: *Jan. 4, 2000

[54] CIRCULARLY PERMUTED LIGANDS AND CIRCULARLY PERMUTED CHIMERIC MOLECULES

[75] Inventors: Ira Pastan; Robert J. Kreitman, both of Potomac; Raj K. Puri, North Potamac, all of Md.

[73] Assignee: The United States of America as represented by the Department of Health and Human Services, Washington, D.C.

[*] Notice: This patent is subject to a terminal disclaimer.

[21] Appl. No.: 08/722,258

[22] PCT Filed: Apr. 6, 1995

[86] PCT No.: PCT/US95/04468

§ 371 Date: Jan. 8, 1997

§ 102(e) Date: Jan. 8, 1997

[87] PCT Pub. No.: WO95/27732

PCT Pub. Date: Oct. 19, 1995

Related U.S. Application Data

[63] Continuation-in-part of application No. 08/225,224, Apr. 8, 1994, Pat. No. 5,635,599.

[51] Int. Cl.[7] .......................... C07K 14/00; A61K 38/16
[52] U.S. Cl. .................. 514/2; 514/12; 530/350; 530/351; 530/395; 530/397; 530/399; 436/501
[58] Field of Search .................... 514/2, 8, 12; 435/69.1, 435/69.5, 69.52, 69.7, 172.3; 436/501; 530/350, 351, 395, 397, 399

[56] References Cited

U.S. PATENT DOCUMENTS 5,635,599  6/1997  Pastan et al. ......................... 530/351

FOREIGN PATENT DOCUMENTS

A O 367 166  5/1990  European Pat. Off. .
A O 370 205  5/1990  European Pat. Off. .

OTHER PUBLICATIONS

Curti. Crit. Rev. Oncology/Hematology 14:29–39, 1993.
Jain. Sci. Am. 271:58–65, 1994.
Buchwalder, et al., A fully active variant of dihydrofolate reductase with a circularly permuted sequence. *Biochemistry*, 31: 1621–1630 (1992).
Cunningham, et al., Favin versus concanavalin A: circularly permuted amino acid sequences. *Proc. Natl. Acad. Sci. USA*, 76: 3218–3222 (1979).
Goldenberg, et al. Circular and circularly permuted forms of bovine pancreatic trypsin inhibitor. *J. Mol. Biol.*, 165: 407–413 (1983).
Goldenberg, Circularly permuted proteins. *Protein Eng.*, 7: 493–495 (1989).
Hoppe, et al., Insulin analogues with permuted A chain N–terminus. *Z. Physiol. Chem.*, 356: 981–986 (1975). (Abstract only).
Horlick, et al., Permuteins of interleukin 1β—a simplified approach for the construction of permutated proteins having new termini. *Protein Eng.*, 5: 427–431 (1992).

(List continued on next page.)

*Primary Examiner*—Elizabeth Kemmerer
*Attorney, Agent, or Firm*—Townsend and Townsend and Crew LLP

[57] ABSTRACT

The present invention provides for circularly permuted ligands which possess specificity and binding affinity comparable to or greater than the specificity and binding affinity of the original (unpermuted) ligand. The invention further provides for novel chimeric molecules comprising a circularly permuted ligand joined to one or more molecules of interest.

50 Claims, 9 Drawing Sheets

OTHER PUBLICATIONS

Luger, et al., Correct folding of circularly permuted variants of a βα barrel enzyme in vivo. *Science*, 243: 206–210 (1989).

Min, et al., Non–glycosylated recombinant pro–concanavalin A is active without polypeptide cleavage. *E.M.B.O. J.*, 11: 1303–1307 (1992).

Pan, et al., Circularly permuted DNA, RNA and proteins—a review. *Gene*, 125:11–114 (1993).

Pastan, et al., 1992 *Ann. Rev. Biochem.* 61:331–54.

Ogata et al., 1989 *PNAS USA* 86:4215–9.

Puri et al., *J. Cancer Res.* 51:3011–.

Pastan et al., *Science* 254:1173–7.

Kreitman et al., *PNAS USA* 91:6889–93.

*The Journal of Biological Chemistry*, vol. 268, No. 19, Jul. 5, 1993 pp. 14065–14070, Waldemar Debinski et al. see page 14068, first paragraph of the Discussion.

*Science*, vol. 245, Sep. 29, 1989 pp. 1493–1496, Cynthia E. Dunbar et al., 'Carboxyl–terminal–modified interleukin–3 is retained intracellularly and stimulates autocrine growth' see the whole document.

*Cancer Research*, vol. 55, No. 15, Aug. 1, 1995 pp. 3357–3363, Robert J. Kreitman et al., 'Increased antitumor activity of a circularly permuted interleukin 4–toxin in mice with interleukin 4 receptor–bearing human carcinoma'.

Pan, et al., Circularly permuted DN

CIRCULARLY PERMUTED LIGANDS AND CIRCULARLY PERMUTED CHIMERIC MOLECULES

This application claims priority to U.S. Pat. No. 5,635,599 and PCT application U.S. 95/04468.

FIELD OF THE INVENTION

This invention relates to the production and use of circularly permuted ligands and chimeric proteins formed by the joining of two or more proteins where one of the proteins is circularly permuted. The chimeric proteins may be fusion proteins.

BACKGROUND OF THE INVENTION

In a chimeric molecule, two or more molecules that exist separately in their native state are joined together to form a single molecule having the desired functionality of all of its constituent molecules. The constituent molecules of a chimeric molecule may be joined by chemical conjugation or, where the constituent molecules are all polypeptides, they may be fused together to form a single continuous polypeptide. If one of the constituent molecules is a ligand, then the resulting chimeric molecules bind to cells bearing receptors specific for the particular ligand.

Where the first constituent molecule is a ligand and the second protein is a cytotoxin, the chimeric molecule may act as a potent cell-killing agent specifically targeting the cytotoxin to cells bearing a particular receptor type. For example, chimeric fusion proteins which include interleukin 4 (IL4) or transforming growth factor (TGFα) fused to Pseudomonas exotoxin (PE) or interleukin 2 (IL2) fused to Diphtheria toxin (DT) have been tested for their ability to specifically target and kill cancer cells (Pastan et al., *Ann. Rev. Biochem.*, 61: 331–354 (1992)).

Alternatively, where the ligand is attached to another specific binding moiety such as an antibody, a growth factor, or another ligand, the chimeric molecule may act as a highly specific bifunctional ligand. This ligand may act to bind and enhance the interaction between cells or cellular components to which the chimeric molecule binds. Thus, for example, where the chimeric molecule is a fusion protein in which a growth factor is fused to an antibody or antibody fragment (e.g. an Fv fragment of an antibody), the antibody may specifically bind antigen positive cancer cells while the growth factor binds receptors (e.g., IL2 or IL4 receptors) on the surface of immune cells. The fusion protein may thus act to enhance and direct an immune response toward target cancer cells.

Ligands are typically employed in chimeric molecules to act as specific targeting moieties. Generally it is desirable to increase specificity and affinity and decrease cross-reactivity of the chimeric molecule to make it more effective. For example, native PE and DT are highly toxic compounds that typically bring about death through liver toxicity. PE and DT can be transformed into chimeric toxins by removing the native targeting component of the toxin and replacing it with a different specific targeting moiety (e.g. IL4 which targets cells bearing IL4 receptors). However, even these chimeric toxins show some non-specific binding. They attack the liver in addition to their target cells and, when given in large doses, may also produce death due to liver toxicity.

It has been observed that growth factors, and other targeting moieties, frequently show lower specificity and affinity for their targets when they are incorporated into chimeric molecules such as fusion proteins. See, for example, Debinski, et al., *J. Biol. Chem.*, 268: 14065–14070 (1993); Lorberboum-Galski, et al., *J. Biol. Chem.*, 263: 18650–18656 (1988); Williams, et al., *J. Biol. Chem.*, 265: 11885–11889 (1990); and Edwards, et al. *Mol. Cell. Biol.*, 9: 2860–2867 (1989).

SUMMARY OF THE INVENTION

This invention provides novel modified forms of ligands such as interleukin 4 (IL4) wherein the amino and carboxy ends are joined together, directly or through a linker, and new amino and carboxy terminal ends are formed al. a different location within the ligand. These modified ligands are as fully active as the original ligands. Since the modification of the ligand represents a rearrangement of the molecule, neither the function, nor the desirability of such molecules was apparent prior to the work described here. Such rearranged molecules are also referred to as circularly permuted molecules.

The circularly permuted ligands are especially useful when employed as a component in a chimeric molecule such as a fusion protein of interest. Oftentimes fusion, or chemical conjugation, of a protein to an original terminus of a ligand interferes with binding of the ligand to its native receptor. For example, fusing a toxin to the carboxy terminus of IL4 greatly interferes with the binding of IL4 to its receptor.

Specific binding affinity of IL4-containing chimeric molecules (e.g. fusion proteins) and cytotoxicity of toxin fusion proteins is greatly enhanced by the use of the circularly permuted (CP) ligands (e.g. CP IL4) described herein. The increased affinity and cytotoxicity obtained by circular permutation of the targeting molecule renders the chimeric CP ligand-cytotoxin molecules of the present invention particularly well suited for in vivo use. Thus this invention provides for methods of inhibiting the in vivo growth of tumor cells by contacting the cells with the cytotoxic chimeric molecules, in particular cytotoxic fusion proteins described herein. In addition, this invention provides for a method of specifically delivering a molecule (e.g., an effector molecule such as a cytotoxin, an antibody, a ligand, a drug, a liposome, a label, a binding protein, a radioactive compound, etc.) to a target cell in vivo. The method involves administering to a mammal a molecule comprising a circularly permuted ligand in a pharmaceutically acceptable carrier; wherein the ligand specifically binds the target cell.

It is believed that the reduced affinity in growth factor-toxin or other ligand-toxin fusion proteins is due, at least in part, to the inability of the targeting moiety to achieve its native conformation when incorporated into a chimeric molecule or to stearic hinderance between the active site of the targeting moiety and the fused protein. This invention overcomes these limitations providing novel ligands and ligand fusion proteins that have a binding specificity and affinity comparable to or greater than native ligand fusion proteins. Thus, a valuable use for circularly permuted ligands is disclosed here and it is shown that such functional permuted ligands may be effectively fused to proteins of interest, such as toxins.

Figure 1A:
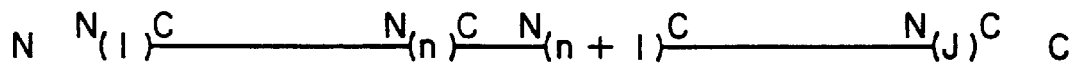
FIG. 1 schematically illustrates the circular permutation of a linear polymer (e.g., a protein). (A) An unpermuted (native) linear protein of length J in which the amino acid residues are numbered sequentially from the amino to the carboxyl terminus from 1 to J. A pair of adjacent amino acids will be numbered n and n+1 respectively where n is an integer ranging from 1 to J−1. The "N" and "C" superscripts on these residues indicates the orientation of the alpha carbon amino and carboxyl groups in each amino acid. (B) The protein of (A) has been circularized by joining the amino and carboxyl termini with a linker (double lines). The circularized protein is then opened at an opening site between the original amino and carboxyl terminal amino acids. The location of the opening site is between adjacent residues n and n+1. (C) Elimination of the peptide bond between residues n and n+1 produces a free alpha carbon carboxyl group on residue n and a free alpha carbon amino group) on residue n+1. Thus, these residues become the new carboxyl and amino termini respectively. Proceeding from the amino to the carboxyl terminus, the protein thus comprises a sequence corresponding essentially to the amino acid sequence of residues n+1 through J of the protein in (a) followed by the linker, followed by a sequence corresponding essentially to the amino acid sequence of residues 1 through n of the protein in (a).
Figure 1B:
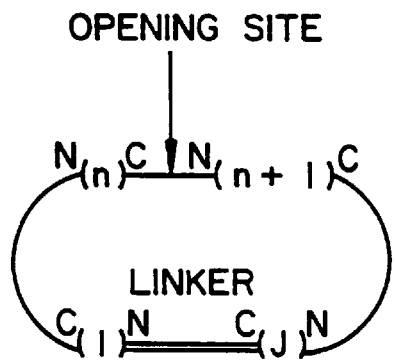
Figure 1C:
Figure 2C:
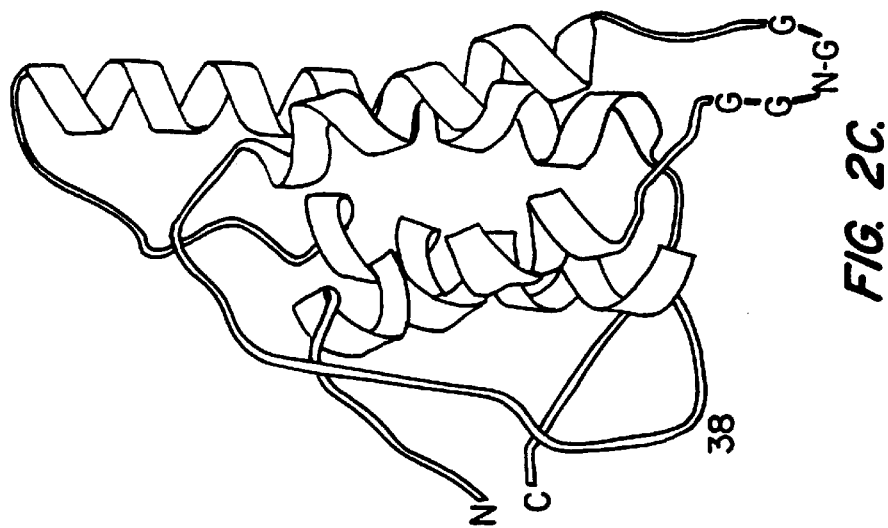
FIG. 2 shows a schematic three dimensional diagram of IL4 and circularly permuted mutants. The three dimensional structure of IL4, based on the NMR coordinates (Powers et al. *Science,* 256: 1673–1677 (1992); Powers et al. *Biochem.,* 32: 6744: 6762 (1993)) was converted to the schematic form shown in A by the Molscript Program (Luger et al. *Science,* 243: 206–210 (1989)). The numbering system used here is based on the 129 amino acid mature IL4 protein, of Sequence Id. No.: 2 which, in recombinant form, is preceded by Met (Redfield et al., *Biochemistry,* 30: 11029–11035 (1991). The structures of IL4(38-37) in B and IL4(105-104) in C were based on that of IL4. IL4(38-37) consisted of Met followed by amino acids 38–129, GGNGG (SEQ ID NO:50), amino acids 1–37 and a C-terminal alanine. IL4 (105-104) consisted of Met followed by amino acids 105–129, GGNGG (SEQ ID NO:50) and 1–104. For cloning purposes, each IL4 mutant contained alanine at the new C-terminus. This alanine was residue 104 for IL4(105-104) and constituted an extra residue for IL4(38-37).

FIG. 3 shows the binding and proliferative activity of circularly permuted IL4 mutants. (A) Displacement analysis: Bound [$^{125}$I]-IL4 plotted as a function of IL4 (O), IL4(38-37) (▲) or IL4(105-104) (□) concentration (B) Mitogenic activity: [$^{3}$H]-thymidine incorporation by CTLL$^{hIL4R}$ cells plotted as a function of IL4(O), IL4(38-37) (▲) or IL4(105-105) (□) concentration. For A and B, the data is composed of the means of triplicate or quadruplicate experiments and error bars represent standard deviations from the mean.

FIG. 4 shows the binding and cytotoxic activity of circularly permuted IL4-PE fusion protein IL4(38-37)-PE38Q compared to the native IL4-PE fusion protein IL4-PE38Q. (A) Amount of ([$^{125}$I]-IL4) bound to DAUDI cells plotted as a function of the concentration of IL4(□), IL4(38-37)-PE38Q (●) or IL4-PE38Q (○) in the culture media. (B) Uptake of [$^{3}$H]-leucine by ATAC-4 cells in the presence of varying concentrations of IL4(38-37)-PE38Q (●) or IL4-PE38Q (○). Cells were also incubated with IL4(38-37)-PE38Q (▲) or IL4-PE38Q (Δ) each combined with an excess (10 μg/ml) of IL4. The $IC_{50}$'s, the concentrations needed for 50% inhibition of protein synthesis, were 0.24 and 0.75 ng/ml for IL4(38-37)-PE38Q and IL4-PE38Q, respectively.

FIG. 5 shows schematic diagrams of various IL4-toxins. The toxins used in Examples 12 and 13 include the CP-IL4-toxin IL4(38-37)-PE38KDEL and the native IL4-toxin IL4-PE38KDEL. IL4(38-37)-PE38KDEL contains an aspartate residue replacing $N^{38}$ just after the initiator methionine, labeled by the letter "D." The CP-IL4 ligand contains the peptide GGNGG (SEQ ID NO:50) joining the native C-terminus to the native N-terminus of IL4. PE38KDEL consists of PE amino acids 253–364 and 381–608, followed by the sequence KDEL (SEQ ID NO:62). IL4-PE38KDEL is the native IL4-toxin containing the toxin fused to the C-terminus of native IL4. The asparagine residue at IL4 position 38 is labeled with the letter "N." The "C3" peptide connector, of sequence ASGGPE (SEQ ID NO:57), joins the C-terminus of the ligand with the toxin. IL4(38-37)-PE38Q and IL4-PE38Q are the respective CP and native IL4-toxins from a previous study. Both of these toxins contain the K590Q and K606Q mutations and the RDEL (SEQ ID NO:61) C-terminus. Also, IL4(38-37)-PE38Q contains the native $N^{38}$ residue just after the initiator methionine.

FIG. 6 illustrates the antitumor activity of the IL4-toxins fusion proteins. Mice were injected with A431 cells subcutaneously on day 0 and on day 4, 6 and 8 received either 50 (A, ■), 100 (B, ▼) or 200 μg/Kg i.v. (C, ●) of IL4(38-37)-PE38KDEL, or 50 (D,□), 100 (E,▽) or 200 μg/Kg i.v. (C,0)) of IL4-PE38KDEL. The numbers of treated mice are 30, 30, 5, 10, 10 and 10 for A, B, C, D, E and F, respectively. Error bars as in FIG. 3. Standard deviations, which are not shown for the 30 untreated mice (Δ), were 15, 58, 43, 146, 198 and 232 $mm^3$ on days 4, 6, 8, 11, 13 and 15, respectively.

FIG. 7 illustrates the durability of complete responses. In A, groups of 10 mice were treated on days 4, 6 and 8 with 50 μg/Kg×3 (□) or 100 μg/Kg×3 (▼) of IL4(38-37)-PE38KDEL. In B, groups of 10 mice were treated on days 4, 6 and 8 with 100 μg/Kg×3 (▽) or 200 μg/Kg×3 (O) of IL4(38-37)-PE38KDEL. The plot shows both the percent of animals achieving complete responses and the durability of these responses.

Definitions

For purposes of the present invention, the following terms are defined below.

The term "circularly permuted" as used herein refers to a linear molecule in which the termini have been joined together, either directly or through a linker, to produce a circular molecule, and then the circular molecule is opened at another location to produce a new linear molecule with termini different from the termini in the original molecule. Circular permutations include those molecules whose structure is equivalent to a molecule that has been circularized and then opened. Thus, a circularly permuted molecule may be synthesized de novo as a linear molecule and never go through a circularization and opening step. The particular circular permutation of a molecule is designated by brackets containing the amino acid residues between which the peptide bond is eliminated. Thus, the designation IL4(105-104) designates a circularly permuted IL4 growth factor in which the opening site (position at which the peptide bond is eliminated) occurred between residues 105 and 104 of the unpermuted or unmodified IL4.

The term "specifically deliver" or "specifically bind" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery or specific binding, may be distinguished as mediated through specific recognition of the target molecule. Typically specific delivery results in a much stronger association between the bound or delivered molecule and cells bearing the target molecule than between the bound or delivered molecule and cells lacking the target molecule. Specific binding or delivery typically results in greater than 2 fold, more preferably greater than 5 fold, and most preferably greater than 10 fold increase in amount of bound or delivered molecule (per unit time) to a cell or tissue bearing the target molecule as compared to a cell or tissue lacking the target molecule or marker.
Figure 2B:
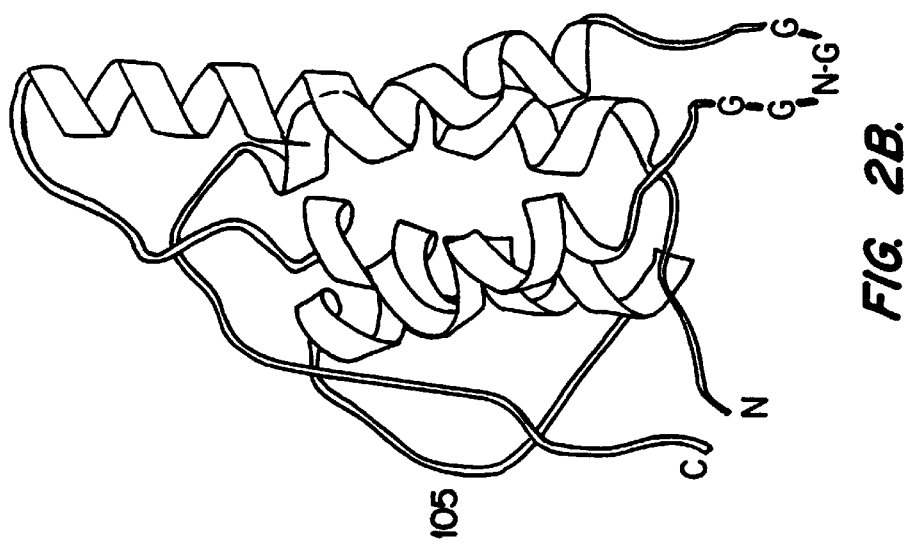
Figure 2A:
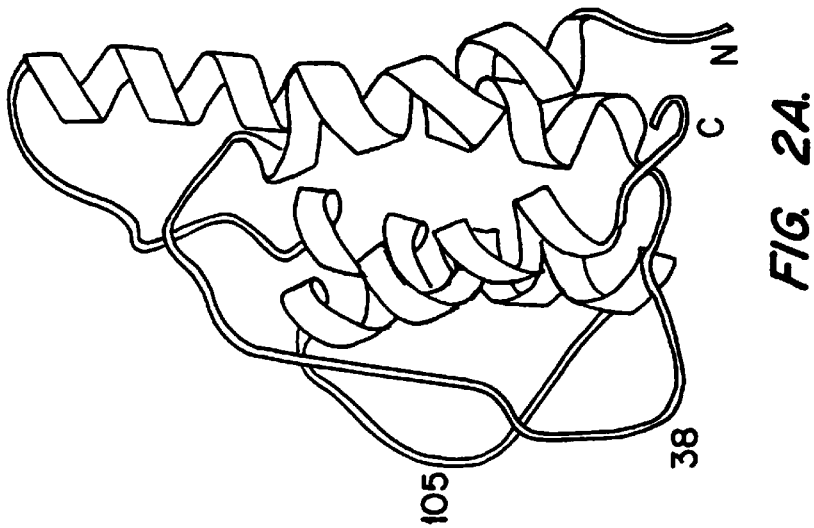

A "spacer" or connector, as used herein, refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The terms "unpermuted," "native" or "unmodified" ligand, growth factor, or protein are used herein to provide a reference point for the ligand, growth factor or protein prior to its rearrangement into a circularly permuted molecule, as described above. Typically, the unmodified ligand, growth factor or protein has amino and carboxyl termini and an amino acid sequence that correspond substantially to the amino and carboxyl termini and amino acid sequence of the ligand, growth factor, or protein as it generally occurs in vivo. The unmodified ligand, growth factor, or protein however, may have a methionine at the amino terminus if produced as a non-selected form.

The term "linker", as used herein, refers to a molecule that is used to join the amino and carboxyl termini of a protein. The linker is capable of forming covalent bonds to both the amino and carboxyl terminus. Suitable linkers are well known to those of skill in the art and include, but are not limited to, straight or branched-chain carbon linkers, heterocyclic carbon linkers, or peptide linkers. The linkers may be joined to the carboxyl and amino terminal amino acids through their side groups (e.g., through a disulfide linkage to cysteine). However, in a preferred embodiment, the linkers will be joined to the alpha carbon amino and carboxyl groups of the terminal amino acids.

A "ligand", as used herein, refers generally to all molecules capable of reacting with or otherwise recognizing or binding to a receptor, antigen, or other molecule on a target cell. Specifically, examples of ligands include, but are not limited to antibodies, lymphokines, cytokines, receptor proteins such as CD4 and CD8, solubilized receptor proteins such as soluble CD4, hormones, growth factors, and the like which specifically bind desired target cells.

A "growth factor" as used herein refers to a protein ligand that stimulates cell division or differentiation or inhibits cell division or stimulates or inhibits a biological response like motility or secretion of proteins. Growth factors are well known to those of skill in the art and include, but are not limited to, platelet-derived growth factor (PDGF), epidermal growth factor (EGF), insulin-like growth factor (IGF), transforming growth factor β (TGF-β), fibroblast growth factors (FGF), interleukin 2 (IL2), nerve growth factor (NGF), interleukin 3 (IL3), interleukin 4 (IL4), interleukin 1 (IL1), interleukin 6 (IL6), interleukin 7 (IL7), granulocyte/macrophage colony-stimulating factor (GM-CSF), granulocyte colony-stimulating factor (G-CSF), macrophage colony-stimulating factor (M-CSF), erythropoietin and the like. One of skill in the art recognizes that the term growth factor as used herein generally includes cytokines and colony stimulating factors.

The term "residue" as used herein refers to an amino acid that is incorporated into a peptide. The amino acid may be a naturally occurring amino acid and, unless otherwise limited, may encompass known analogs of natural amino acids that can function in a similar manner as naturally occurring amino acids.

The term "opening site", as used herein when referring to circular permutation, refers to the position at which a peptide bond would be eliminated to form new amino and carboxyl termini. The opening site is designated by the positions of the pair of amino acids, located between the amino and carboxyl termini of the unpermuted (native) protein, that become the new amino and carboxyl termini of the circularly permuted protein. Where the unpermuted protein is J amino acids in length and its residues are numbered 1 through J from the amino to the carboxyl terminus, the opening site will be designated as between residues n and n+1 where n is an integer from 1 through J−1.

The term "antibody", as used herein, includes various forms of modified or altered antibodies, such as an intact immunoglobulin, an Fv fragment containing only the light and heavy chain variable regions, an Fv fragment linked by a disulfide bond (Brinkmann, et al. *Proc. Natl. Acad. Sci. U.S.A.,* 90: 547–551 (1993)), an Fab or (Fab)'$_2$ fragment containing the variable regions and parts of the constant regions, a single-chain antibody and the like (Bird et al., *Science* 242: 424–426 (1988); Huston et al., *Proc. Nat. Acad. Sci. U.S.A.* 85: 5879–5883 (1988)). The antibody may be of animal (especially mouse or rat) or human origin or may be chimeric (Morrison et al., *Proc Nat. Acad. Sci. U.S.A.* 81: 6851–6855 (1984)) or humanized (Jones et al., *Nature* 321: 522–525 (1986), and published UK patent application #8707252). Methods of producing antibodies suitable for use in the present invention are well known to those skilled in the art and can be found described in such publications as Harlow & Lane, *Antibodies: A Laboratory Manual,* Cold Spring Harbor Laboratory (1988), and Asai, *Methods in Cell Biology Vol. 37. Antibodies in Cell Biology,* Academic Press, Inc. N.Y. (1993).

The term "Pseudomonas exotoxin" (PE) as used herein refers to a full-length native (naturally occurring) PE or a PE that has been modified. Such modifications may include, but are not limited to, elimination of domain Ia, various amino acid deletions in domains II and III, single amino acid substitutions (e.g., replacing Lys with Gln at positions 590 and 606), and the addition of one or more sequences at the carboxyl terminus such as KDEL (SEQ ID NO:62) and REDL (SEQ ID NO:60).

The term "Diphtheria toxin" (DT) as used herein refers to fill length native DT or to a DT that has been modified. Modifications typically include removal of the targeting domain in the B chain and, more specifically, involve truncations of the carboxyl region of the B chain.

All amino acid positions described herein use as a frame of reference sequences for native Pseudomonas exotoxin (PE) (SEQ ID NO:1), IL4 (SEQ ID NO:2), IL2 (SEQ ID NO:3), GM-CSF (SEQ ID NO:4), G-CSF (SEQ ID NO:5) as presented in the Sequence Listing. For example, a PE molecule "comprising amino acids 280 to 613" would refer to a molecule having amino acids substantially corresponding to those positions in SEQ ID NO:1. Other common references are used herein to indicate deletions or substitutions to a sequence using the respective native sequence Id. listing as a frame of reference. The use of the symbol "Δ" refers to a deletion of the amino acids following the symbol. For example, "Δ365–380", refers to the deletion from a PE molecule of amino acids 365 to 380. Amino acid substitutions may be indicated by parentheses, for example "(Ser 287)" refers to a molecule having serine at amino acid position 287. Circularly permuted molecules are designated by the native molecule followed by brackets enclosing the amino acid positions that comprise the opening site. Thus, for example, IL4(105-104) designates a circularly permuted IL4 in which the new termini are residues 105 and 104 of the unpermuted IL4. Amino acids are also sometimes referred to here by the single letter codes recommended by the IUPAC-IUB Biochemical Nomenclature commission. It is, of course, recognized that some substitutions, addition, or deletions may be made to any sequences described herein that do not alter the biological activity of the region. Indeed, some such modifications may be required to achieve expression of a particular protein. Thus, for example, a methionine may be added to a sequence to provide an initiator.

DETAILED DESCRIPTION

Circularly Permuted Ligands and Chimeric Molecules

The present invention provides for circularly permuted ligands which possess specificity and binding affinity comparable to or greater than the specificity and binding affinity of the native (unpermuted) ligand.

The present invention also provides for novel chimeric molecules comprising at least one circularly permuted ligand joined to one or more second molecule(s) of interest which may be, for example, a cytotoxin, an antibody, a ligand, a hormone, a growth factor, a drug, a liposome, a detectable label, a circularly permuted ligand, a circularly permuted hormone, or a circularly permuted growth factor. The first circularly permuted ligand acts to target and bind the chimeric molecule to particular cells or cellular components where the second molecule may exercise it; characteristic activity.

In a number of ligands (e.g. growth factors and other proteins), the carboxyl and amino termini are situated relatively close to the active site when the protein is folded into its native conformation. When chimeric molecules or fusion proteins are formed by joining a second protein to either terminus of the first protein (e.g. by fusion), specificity, binding affinity, or other activities of the joined first protein may be decreased relative to the unfused first protein presumably due to altered folding caused by the presence of the added protein component or to stearic hinderance between the second protein component and the active site of the first protein component.

Circular permutation of the molecule as described here provides a means by which the first protein may be altered to produce new carboxyl and amino termini without diminishing the specificity and binding affinity of the altered first protein relative to its native form. With new termini located away from the active site, it is possible to incorporate the circularly permuted first proteins into chimeric molecules (e.g. fusion proteins) with a smaller or no diminution of activity of the first protein.

Circular Permutation

Circularly permuted molecules, which may include DNA, RNA and protein, are single-chain molecules which have their normal termini fused, often with a linker, and contain new termini at another position. See Goldenberg, et al. *J. Mol. Biol.,* 165: 407–413 (1983) and Pan et al. *Gene* 125: 111–114 (1993), both incorporated by reference herein. Circular permutation is functionally equivalent to taking a straight-chain molecule, fusing the ends to form a circular molecule, and then cutting the circular molecule at a different location to form a new straight chain molecule with different termini. Circular permutation thus has the effect of essentially preserving the sequence and identity of the amino acids of a protein while generating new termini at different locations.

The process of circular permutation is schematically illustrated in FIG. 1. FIG. 1(A) illustrates an unpermuted linear polymeric molecule (in this case a protein) J subunits in length. The constituent amino acid residues are numbered sequentially 1 through J from the amino to the carboxyl terminus. A pair of adjacent amino acids within this protein may be numbered n and n+1 respectively where n is an integer ranging from 1 to J–1. To circularly permute the protein, the amino and carboxyl termini are first joined by a linker producing a circular molecule (FIG. 1(B)). A new linear molecule is formed by cutting or opening the circular molecule at any location between amino acid residues 1 and J. Thus, the location of the opening; site, illustrated by the arrow in FIG. 1(B) may be designated as between amino acid residues n and n+1. Elimination of the peptide bond between residue n and n+1 will produce a free alpha carbon amino group on residue n+1 and a free alpha carbon carboxy group on residue n. These residues become the new amino and carboxyl termini respectively (FIG. 1(C)). Thus, circular permutation produces a new linear protein which, proceeding from the amino to the carboxyl terminus, comprises the segment of the original protein corresponding to residues n+1 through J followed by the linker, followed by a segment of the original protein corresponding to residues 1 through n (FIG. 1(C)).

It will be appreciated that while circular permutation is described in terms of linking the two ends of a protein and then cutting the circularized protein these steps are not actually required to create the end product. A protein synthesized de novo with the sequence illustrated by FIG. 1(C) would be equivalent to a protein made by circularization and cutting. Thus, circularized permutations of a generic protein illustrated by FIG. 1(A) refers to all proteins of FIG. 1(C) structure regardless of how they are constructed.

It is important to create a permutation that will retain the biological activity of the native form of the molecule. If the new termini interrupt a critical region of the native protein, activity may be lost. Similarly, if linking the original termini destroys activity, then no permutation will retain biological activity. Thus, there are two requirements for the creation of an active circularly permuted protein: 1) The termini in the native protein must be favorably located so that creation of a linkage does not destroy biological activity; and 2) There must exist an “opening site” where new termini can be formed without disrupting a region critical for protein folding and desired biological activity.

Thus, in general, good candidates for circular permutation are proteins in which the termini of the original protein are in close proximity and favorably oriented. Where the termini are naturally situated close together, it is expected that direct fusion of the termini to each other or introduction of a linker will have relatively little effect. It has been suggested that in roughly one third of the known structures of globular proteins the termini are in relatively close proximity (Thorton et al. *J. Mol. Biol.,* 167: 443–460 (1983)). However, because the linker may be of any length, close proximity of the native termini is not an absolute requirement.

In a preferred embodiment, it is desirable to use a linker that preserves the spacing between the termini comparable to the unpermuted or native molecule. Generally linkers are either hetero- or homo-bifunctional molecules that contain two reactive sites that may each form a covalent bond with the carboxyl and the amino terminal amino acids respectively. Suitable linkers are well known to those of skill in the art and include, but are not limited to, straight or branched-chain carbon linkers, heterocyclic carbon linkers, or peptide linkers. The most common and simple example is a peptide linker that typically consists of several amino acids joined through peptide bonds to the termini of the native protein. The linkers may be joined to the terminal amino acids through their side groups (e.g., through a disulfide linkage to cysteine). However, in a preferred embodiment, the linkers will be joined through peptide bonds to the alpha carbon amino and carboxyl groups of the terminal amino acids.

Functional groups capable of forming covalent bonds with the amino and carboxyl terminal amino acids are well known to those of skill in the art. For example, functional groups capable of binding the terminal amino group include anhydrides, carbodimides, acid chlorides, activated esters and the like. Similarly, functional groups capable of forming covalent linkages with the terminal carboxyl include amines, alcohols, and the like. In a preferred embodiment, the linker will itself be a peptide and will be joined to the protein termini by peptide bonds. For example, the termini of the growth factor IL4 are normally spaced about 11.2 Å apart (Powers et al. *Biochem.*, 32: 6744–6762 (1993). A preferred linker that essentially preserves this spacing is the peptide GGNGG (SEQ ID NO:50). Similarly, a preferred linker for circularly permuted G-CSF and GM-CSF is GGGNGGG (SEQ ID NO:52).

Circular permutation requires that the protein have an opening site (i.e., between residues n and n+1) where the formation of termini will not interrupt secondary structure crucial in the folding process or critical elements of the final conformation. Even if the three-dimensional structure is compatible with joining the termini, it is conceivable that the kinetics and thermodynamics of folding would be greatly altered by circular permutation if opening the circularized protein separates residues that participate in short range interactions crucial for the folding mechanism or the stability of the native state. Goldenberg, *Protein Eng.*, 7: 493–495 (1989). Thus, the choice of an opening site is important to the protein activity.

The selection of an opening site may be determined by a number of factors. Where the three dimensional conformation of the protein is known or predicted, preferred opening sites will be located in regions that do not show a highly regular three-dimensional structure. Thus, it is preferred that opening sites be selected in regions of the protein that do not show secondary structure such as alpha helices, pleated sheets, αβ barrel structures, and the like.

Methods of identifying regions of particular secondary structure based on amino acid sequence are widely known to those of skill in the art. See, for example, Cohen et al., *Science,* 263: 488–489 (1994), incorporated by reference herein. Numerous programs exist that predict protein folding based on sequence data. Some of the more widely known software packages include MatchMaker (Tripos Associates, St. Louis, Mo., U.S.A.), FASMAN from GCG (Genetics Computer Group), PHD (European Molecular Biology Laboratory, Heidelburg, Germany) and the like.

Alternatively, where the substitution of certain amino acids or the modification of the side chains of certain amino acids does not change the activity of a protein, it is expected that the modified amino acids are not critical to the protein's activity. Thus, amino acids that are either known to be susceptible ti) modification or are actually modified in vivo are potentially good candidates for opening sites. For example, residues 38 and 105 of IL4 are potential glycosylation sites (Carr et al., *Biochem.*, 80: 1515–111523 (1991), Powers et al., *Science* 256: 1673–1677 (1992)). Glycosylation of residue 38 in IL4 does not change the binding specificity or affinity of IL4 for its target receptors. Thus residues 38 and 105 are potentially good candidates for opening sites.

Where the protein is a member of a family of related proteins, one may infer that the highly conserved sequences are critical for biological activity, while the variable regions are not. Preferred opening sites are then selected in regions of the protein that do not show highly conserved sequence identity between various members of the protein family. Alternatively, if an opening site is identified in a (conserved region of a protein, that same region provides a good candidate for opening sites in a homologous protein.

Methods of determining sequence identity are well known to those of skill in the art. Sequence comparisons between two (or more) polynucleotides or polypeptides are typically performed by comparing regions of the two sequences over a "comparison window" to identify and compare local regions of sequence similarity. Since the goal is to identify very local sequence regions that are not conserved, the comparison window will be selected to be rather small. A "comparison window", as used herein, refers to a segment of at least about 5 contiguous positions, usually about 10 to about 50, more usually about 15 to about 40 in which a sequence may be compared to a reference sequence of the same number of contiguous positions after the two sequences are optimally aligned.

Optimal alignment of sequences for comparison may be conducted by the local homology algorithm of Smith et al. *Adv. Appl. Math.* 2: 482 (1981), by the homology alignment algorithm of Needleman et al., *J. Mol. Biol.* 48:443 (1970), by the search for similarity method of Pearson et al., *Proc. Natl. Acad. Sci. U.S.A.*, 85: 2444 (1988), by computerized implementations of these algorithms (GAP, BESTFIT, FASTA, and TFASTA in the Wisconsin Genetics Software Package, Genetics Computer Group (GCG), 575 Science Dr., Madison, Wis., U.S.A.), or by inspection.

Preferred opening sites in IL4 are between residues 37 and 38 and between residues 104 and 105. A preferred opening site in IL2 is between residues 39 and 38, while preferred opening sites in GM-CSF and G-CSF are between residues 36 and 35 and between residues 69 and 68 respectively.

Preparation of Circularly Permuted Proteins

Circularly permuted proteins may be made by a number of means known to those of skill in the art. These include chemical synthesis, modification of existing proteins, and expression of circularly permuted proteins using recombinant DNA methodology.

Where the protein is relatively short (i.e., less than about 50 amino acids) the circularly permuted protein may be synthesized using standard chemical peptide synthesis techniques. If the linker is a peptide it may be incorporated during the synthesis. If the linker is not a peptide it may be coupled to the peptide after synthesis. Solid phase synthesis in which the C-terminal amino acid of the sequence is attached to an insoluble support followed by sequential addition of the remaining amino acids in the sequence is the preferred method for the chemical synthesis of the circularly permuted ligands and fusion proteins of this invention. Techniques for solid phase, synthesis are described by Barany and Merrifield, *Solid-Phase Peptide Synthesis;* pp. 3–284 in *The Peptides: Analysis, Synthesis, Biology. Vol.* 2: *Special Methods in Peptide Synthesis, Part A.*, Merrifield, et al. *J. Am. Chem. Soc.*, 85: 2149–2156 (1963), and Stewart et al., *Solid Phase Peptide Synthesis, 2nd ed.* Pierce Chem. Co., Rockford, Ill. (1984) which are incorporated herein by reference.

Alternatively, the circularly permuted protein may be made by chemically modifying a native protein. Generally, this requires reacting the native protein in the presence of the linker to form covalent bonds between the linker and the carboxyl and amino termini of the protein, thus forming a circular protein. New termini are then formed by opening the peptide bond joining amino acids at another location. This may be accomplished chemically or enzymatically using, for example, a peptidase.

If the opening reaction tends to hydrolyze more than one peptide bond, the reaction may be run briefly. Those molecules having more than one peptide bond opened will be shorter than the full length circularly permuted molecule and the latter may be isolated by any protein purification technique that selects by size (e.g., by size exclusion chromatography or electrophoresis). Alternatively, various sites in the circular protein may be protected from hydrolysis by chemical modification of the amino acid side chains which may interfere with enzyme binding, or by chemical blocking of the vulnerable groups participating in the peptide bond.

In a preferred embodiment, the circularly permuted protein, or fusion proteins comprising the circularly permuted protein will be synthesized using recombinant DNA methodology. Generally this involves creating a DNA sequence that encodes the circularly permuted ligand (or entire fusion protein containing the ligand), placing the DNA in an expression cassette under the control of a particular promoter, expressing the protein in a host, isolating the expressed protein and, if required, renaturing the protein.

DNA encoding circularly permuted ligands or fusion proteins comprising circularly permuted ligands may be prepared by any suitable method, including, for example, cloning and restriction of appropriate sequences or direct chemical synthesis by methods such as the phosphotriester method of Narang et al. *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.,* 22: 1859–1862 (1981); and the solid support method of U.S. Pat. No. 4,458,066, all incorporated by reference herein.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In a preferred embodiment, DNA encoding the circularly permuted ligand may be produced using DNA amplification methods, for example polymerase chain reaction (PCR). First, the segments of the native DNA on either side of the new terminus are amplified separately. For example, since the native protein sequence of IL4 is 129 amino acids long and the opening site is between amino acids 37 and 38 respectively, the sequences representing codons 1 through 37 and 38 through 129 are amplified separately. The 5' end of the first amplified sequence encodes the peptide linker, while the 3' end of the second amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons 38–129, the linker, and codons 1–37. The circularly permuted molecule may then be ligated into a plasmid.

CP Ligand-Containing Chimeric Molecules

One of skill will appreciate that the circularly permuted ligand and the other molecule comprising the chimeric molecules may be joined together in any order. Thus, the second molecule is preferably joined to either the amino or carboxy termini of the circularly permuted ligand.

The chimeric molecules of the present invention may be produced by joining the circularly permuted ligand to a second molecule by any of a number of means well known to those of skill in the art. Typically the molecules will either be chemically linked together (chemical conjugation) or, where both molecules comprising the chimeric molecule are polypeptides the molecules may be fused together to form a polypeptide having a single continuous peptide backbone. Where possible, recombinant fusion is preferred.

A) Chemical Conjugation

Means of chemically conjugating molecules are well known to those of skill. The procedure for attaching an agent (e.g. a cytotoxin) to a circularly permuted ligand may vary according to the chemical structure of the agent. Preferable linkages, however, are to the free amino or carboxyl termini which are available for reaction with a suitable functional group on a linker to bind the two molecules together.

A "connector" or "spacer", as used herein, is a molecule that is used to join the targeting molecule to the effector molecule. The connector is capable of forming covalent bonds to both the targeting molecule and to the effector molecule. Suitable connectors are well known to those of skill in the art and include, but are not limited to, straight or branched-chain carbon linkers, heterocyclic carbon linkers, or peptide connectors. Where the targeting molecule and the effector molecule are polypeptides, the connectors may be joined to the constituent amino acids through their side groups (e.g., through a disulfide linkage to cysteine). However, in a preferred embodiment, the connectors will be joined to the alpha carbon amino and carboxyl groups of the terminal amino acids.

A bifunctional connector having one functional group reactive with a group on a circularly permuted ligand and another group reactive with an antibody, cytotoxin, or the like, may be used to form the desired chimeric molecule. Alternatively, derivatization may involve chemical treatment of the second molecule e.g., glycol cleavage of the sugar moiety of a glycoprotein antibody with periodate to generate free aldehyde groups. The free aldehyde groups on the antibody may be reacted with free amine or hydrazine groups on a circularly permuted ligand to bind the ligand thereto. (See U.S. Pat. No. 4,671,958). Procedures for generation of free sulfydryl groups on polypeptides, such as antibodies, antibody fragments, ligands, and cytotoxins, are also known (See U.S. Pat. No. 4,659,839).

Many procedures and connector molecules for attachment of various compounds including radionuclide metal chelates, toxins and drugs to proteins such as circularly permuted ligands are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. *Cancer Res.* 47: 4071–4075 (1987) which are incorporated herein by reference. In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine,* Academic Press, pp. 168–190 (1982), Waldmann, *Science,* 252: 1657 (1991), U.S. Pat. Nos. 4,545, 985 and 4,894,443 which are incorporated herein by reference.

In some circumstances, it is desirable to separate the constituent molecules of comprising the chimeric molecule when the chimeric molecule has reached its target site. Therefore, chimeric conjugates comprising connectors which are cleavable in the vicinity of the target site may be used when the second molecule is to be released at the target site. Cleaving of the connector to release the agent from the circularly permuted ligand may be prompted by enzymatic activity or conditions to which the chimeric molecule is subjected either inside the target cell or in the vicinity of the target site. When the target site is a tumor, a connector which is cleavable under conditions present at the tumor site (e.g. when exposed to tumor-associated enzymes or acidic pH) may be used.

A number of different cleavable connectors are known to those of skill in the art. See U.S. Pat. Nos. 4,618,492; 4,542,225, and 4,625,014. The mechanisms for release of an agent from these connector groups include, for example, irradiation of a photolabile bond and acid-catalyzed hydrolysis. U.S. Pat. No. 4,671,958, for example, includes a description of immunoconjugates comprising connectors which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to a circularly permuted ligand.

B) Fusion Proteins

In a particularly preferred embodiment, the chimeric molecules are fusion proteins. The fusion proteins may be produced using chemical methods to form a peptide bond joining the two molecules.

In a preferred embodiment however, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins (e.g. CP IL4-PE38Q) of this invention may be prepared by any suitable method, including, for example, cloning and restriction of appropriate sequences or direct chemical synthesis by methods such as the phosphotriester method of Narang et al. *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.*, 22: 1859–1862 (1981); and the solid support method of U.S. Pat. No. 4,458,066, all incorporated by reference herein.

Expression of CP Ligands and Fusion Proteins

The circularly permuted ligands and their fusion proteins may be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes, *Protein Purification,* Springer-Verlag, N.Y. (1982), Deutscher, *Methods in Enzymology Vol.* 182: *Guide to Protein Purification.*, Academic Press, Inc. N.Y. (1990)). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

Modifications of CP Ligands and Chimeric Molecules

One of skill in the art would recognize that after chemical synthesis, biological expression, or purification, the circularly permuted growth-factor or a fusion protein comprising a circularly permuted growth-factor may possess a conformation substantially different than the native protein. In this case, it may be necessary to denature and reduce the protein and then to cause the protein to re-fold into the preferred conformation. Methods of reducing and denaturing the protein and inducing re-folding are well known to those of skill in the art. (See, Debinski et al. *J. Biol. Chem.,* 268: 14065–14070 (1993); Kreitman and Pastan, *Bioconjug. Chem.,* 4: 581–585 (1993); and Buchner, et al., *Anal. Biochem.,* 205: 263–270 (1992) which are incorporated herein by reference.) Debinski et al., for example, describe the denaturation and reduction of inclusion body proteins in guanidine-DTE. The protein is then refolded in a redox buffer containing oxidized glutathione and L-arginine.

One of skill would recognize that modifications can be made to the circularized protein without diminishing its biological activity. Some modifications may be made to facilitate the cloning, expression, or incorporation of the circularly permuted ligand into a fusion protein. Such modifications are well known to those of skill in the art and include, for example, a methionine added at the amino terminus to provide an initiation site, or additional amino acids placed on either terminus to create conveniently located restriction sites or termination codons. For example, in a preferred embodiment, circularly permuted IL4 will have an additional methionine (Met) at the amino terminus to provide an initiation site. For cloning purposes, each IL4 mutant will contain alanine at the new C-terminus. This alanine is residue 104 for IL4(105-104) and constitutes an additional residue for IL4(38-37).

It was a surprising discovery in one embodiment of the present invention that modification of the amino terminus of the circularly permuted ligand increased growth of the bacteria expressing the modified ligand. In particular it was noted that expression bacteria encoding the circularly permuted IL4-toxin (IL4(38-37)-PE38Q) grew only 2% as well as the expression bacteria transformed with a plasmid encoding the native IL4-toxin (IL4-PE38Q or IL4-PE38KDEL). However, when the asparagine at the amino terminus of IL4(38-37)-PE38KDEL was changed to aspartate so that the amino terminal sequence was changed from MNTTE . . . (SEQ ID NO:63) to MDTTE . . . (SEQ ID NO:64), bacterial growth was very good, reaching a level that was 40% that of native IL4-toxin.

One of skill will recognize that other modifications may be made. Thus, for example, amino acid substitutions may be made that increase specificity or binding affinity of the circularly permuted protein, etc. Alternatively, non-essential regions of the molecule may be shortened or eliminated entirely. Thus, where there are regions of the molecule that are not themselves involved in the activity of the molecule, they may be eliminated or replaced with shorter segments that merely serve to maintain the correct spatial relationships between the active components of the molecule.

This invention provides for chimeric molecules including fusion proteins comprising a circularly permuted ligand joined to another protein such as an antibody, an antibody fragment (e.g. anti-Tac(Fv)), a hormone, an enzyme, a releasing factor, a ligand, a growth factor, a circularly permuted growth factor, or another circularly permuted ligand. The two proteins may be fused together directly or joined by means of a peptide spacer. The peptide spacer may range from about 1 to 40 residues in length. In one preferred embodiment, the circularly permuted ligand is a growth factor.

Generally, the spacer has no biological activity itself and functions only to link and provide some distance between the two active proteins comprising the fusion protein. However, one of skill will recognize that the residues of the spacer may be chosen to optimize a property of the fusion protein. For example, a spacer containing hydrophobic amino acids may enhance the solubility of the fusion protein in various lipids, while polar or charged residues in the spacer may enhance solubility in aqueous solutions. Similarly, the spacer residues may be chosen for their effect on the folding of the fusion protein. Where the fusion protein comprises a circularly permuted IL4, IL2, GM-CSF, or G-CSF joined to a Pseudomonas exotoxin a preferred peptide spacer is ASGGPE (SEQ ID NO:57). Where the last amino acid of the protein is alanine (as in IL4(105-104)), the protein and spacer may share the alanine. Where the fusion protein comprises a circularly permuted IL4 joined to Diptheria toxin DT388 preferred spacers are HM or RPHMAD (SEQ ID NO:53). Where the fusion protein comprises circularly permuted IL4 joined to an B3(Fv), a preferred spacer is ASGGPE (SEQ ID NO:57).

Chimeric CP Ligand-Toxin Molecules

Chimeric ligand-toxin molecules are of particular interest and comprise a circularly permuted ligand joined to a toxin. Particularly preferred are chimeric toxin fusion proteins. One of skill in the art would recognize that many toxins are suitable including Pseudomonas exotoxin, Diphtheria toxin, other bacterial toxins, and derivatives of plant or animal toxins. In a preferred embodiment, the fusion protein comprises a circularly permuted growth-factor fused to either a Pseudomonas exotoxin or a Diphtheria toxin.

Pseudomonas exotoxin A (PE) is an extremely active monomeric protein (molecular weight 66 kD), secreted by *Pseudomonas aeruginosa,* which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1–252) mediates cell binding. Domain II (amino acids 253–364) is responsible for translocation into the cytosol and domain III (amino acids 400–613) mediates ADP ribosylation of elongation factor 2, which inactivates the protein and causes cell death. The function of domain Ib (amino acids 365–399) remains undefined, although a large part of it, amino acids 365–380, can be deleted without loss of cytotoxicity. See Siegall et al., *J. Biol. Chem.* 264: 14256–14261 (1989), incorporated by reference herein. For example, in the case of B3(Fv)PE38 (described below), residues 350 to 394 can be deleted and if replaced with GGGGS SEQ ID NO:54) are fully active.

Where the circularly permuted ligand is fused to PE, i preferred PE molecule is one in which domain Ia (amino acids 1 through 252) is deleted and amino acids 365 to 380 have been deleted from domain lb. However all of domain Ib and a portion of domain II (amino acids 350 to 394) can be deleted, particularly if the deleted sequences are replaced with a linking peptide such as GGGGS (SEQ ID NO:54).

In addition, the PE molecules can be further modified using site-directed mutagenesis or other techniques known in the art, to alter the molecule for a particular desired application. Means to alter the PE molecule in a manner that does not substantially affect the functional advantages provided by the PE molecules described here can also be used and such resulting molecules are intended to be covered herein.

For maximum cytotoxic properties of a preferred PE molecule, several modifications to the molecule are recommended. An appropriate carboxyl terminal sequence to the recombinant molecule is preferred to translocate the molecule into the cytosol of target cells. Amino acid sequences which have been found to be effective include, REDLK (SEQ ID NO:59) (as in native PE), REDL (SEQ ID NO:60), RDEL (SEQ ID NO:61), or KDEL (SEQ ID NO:62), repeats of those, or other sequences that function to maintain or recycle proteins into the endoplasmic reticulum, referred to here as "endoplasmic retention sequences". See, for example, Chaudhary et al, *Proc. Natl. Acad. Sci. U.S.A.* 87:308–312 and Seetharam et al, *J. Biol. Chem.* 266: 17376–17381 (1991) and commonly assigned, U.S. Ser. No. 07/459,635 filed Jan. 2, 1990, all of which are incorporated by reference herein.

Deletions of amino acids 365–380 of domain Ib can be made without loss of activity. Further, a substitution of methionine at amino acid position 280 in place of glycine to allow the synthesis of the protein to begin and of serine at amino acid position 287 in place of cysteine to prevent formation of improper disulfide bonds is beneficial. In a preferred embodiment, the circularly permuted ligand is inserted in replacement for domain Ia. A similar insertion has been accomplished in what is known as the TGFα/PE40 molecule (also referred to as TP40) described in Heimbrook et al., *Proc. Natl. Acad. Sci., U.S.A.,* 87: 4697–4701 (1990) and in commonly assigned U.S. Ser. No. 07/865,722 filed Apr. 8, 1992 now abandoned and in U.S. Ser. No. 07/522, 563 filed May 14, 1990 now U.S. Pat. No. 5,458,878, all of which are incorporated by reference.

Preferred forms of PE contain amino acids 253–364 and 381–608, and are followed by the native sequences REDLK (SEQ ID NO:59) or the mutant sequences KDEL (SEQ ID NO:62) or RDEL (SEQ ID NO:61). Lysines at positions 590 and 606 may or may not be mutated to glutamine.

In a particularly preferred embodiment, the circularly permuted ligand-PE fusion proteins of this invention comprise the PE molecule designated PE38Q. This PE molecule is a truncated form of PE composed of amino acids 253–364 and 381–608. The native C-terminus of PE, REDLK (SEQ ID NO:59) (residues 609–613), is replaced with the sequence RDEL (SEQ ID NO:61), and Lys-590 and Lys-606 are each mutated to Gln (mutations K590Q and K606Q, respectively). IL4-PE38Q contains the toxin fused, through a linker, to the C-terminus of IL4, and IL4(38-37)-PE38Q contains the toxin fused, through a linker, to the C-terminus of IL4(38-37). The production of IL4(38-37)-PE38Q is described in detail in Example 2.

In another particularly preferred embodiment, the circularly permuted ligand-PE fusion proteins of this invention comprise the PE molecule designated PE38KDEL. PE38KDEL consists of amino acids 253–364 and 381–608 of PE with the native lysine residues at positions 590 and 606, and it ends with KDEL (SEQ ID NO:62) instead of RDEL (SEQ ID NO:61).

The circularly permuted ligand may also be inserted at a point within domain III of the PE molecule. Most preferably the circularly permuted ligand is fused between about amino acid positions 607 and 609 of the PE molecule. This means that the circularly permuted ligand is inserted after about amino acid 607 of the molecule and an appropriate carboxyl end of PE is recreated by placing amino acids about 604–613 of PE after the circularly permuted ligand. Thus, the circularly permuted ligand is inserted within the recombinant PE molecule after about amino acid 607 and is followed by amino acids 604–613 of domain III. The circularly permuted ligand may also be inserted into domain Ib to replace sequences not necessary for toxicity. Debinski, et al. *Mol. Cell. Biol.*, 11: 1751–1753 (1991).

In a preferred embodiment, the PE molecules will be fused to the circularly permuted ligand by recombinant means. The genes encoding, protein chains may be cloned in cDNA or in genomic form by any cloning procedure known to those skilled in the art. See for example Sambrook et al., *Molecular Cloning: A Laboratory Manual*, Cold Spring Harbor laboratory, (1989), incorporated by reference herein. Methods of cloning genes encoding PE fused to various ligands are well known to those of skill in the art. See, for example, Siegall et al., *FASEB J.*, 3: 2647–2652 (1989); Chaudhary et al. *Proc. Natl. Acad. Sci. U.S.A.*, 84: 4538–4542 (1987), which are incorporated herein by reference.

Those skilled in the art will realize that additional modifications, deletions, insertions and the like may be made to the circularly permuted ligand and PE genes. Especially, deletions or changes may be made in PE or in a linker connecting an antibody gene to PE, in order to increase cytotoxicity of the fusion protein toward target cells or to decrease nonspecific cytotoxicity toward cells without antigen for the antibody. All such constructions may be made by methods of genetic engineering well known to those skilled in the art (see, generally, Sambrook et al., supra) and may produce proteins that have differing properties of affinity, specificity, stability and toxicity that make them particularly suitable for various clinical or biological applications.

In a particularly preferred embodiment, the aspartate replaces asparagine at position 38, the position immediately following the initiator methionine in IL4(38-37)-PE38KDEL. It was a discovery of the present invention that changing the amino terminus such that the first asparagine was replaced with an aspartate (e.g. a change of the amino terminus from MNTTE (SEQ ID NO:63) to MDTTE (SEQ ID NO:61)) results in greatly increased growth of the expression bacteria.

Like PE, diphtheria toxin (DT) kills cells by ADP-ribosylating elongation factor 2 thereby inhibiting protein synthesis. Diphtheria toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al., *Science*, 175: 901–903 (1972); Uchida et al. *J. Biol. Chem.*, 248: 3838–3844 (1973)).

In a preferred embodiment, the circularly permuted ligand-Diphtheria toxin fusion proteins of this invention have the native receptor-binding domain removed by truncation of the Diphtheria toxin B chain. Particularly preferred is DT388, a DT in which the carboxyl terminal sequence beginning at residue 389 is removed. Chaudhary, et al., *Bioch. Biophys. Res. Comm.*, 180: 545–551 (1991).

Like the PE fusion proteins, the DT molecules will be fused to the circularly permuted ligand by recombinant means. The genes encoding protein chains may be cloned in cDNA or in genomic form by any cloning procedure known to those skilled in the art. Methods of cloning genes encoding DT fused to various ligands are also well known to those of skill in the art. See, for example, Williams et al. *J. Biol. Chem.* 265: 11885–11889 (1990) and copending patent application (U.S. Ser. No. 07/620,939) which describe the expression of a number of growth-factor-DT fusion proteins.

The present invention also provides for "dual targeted" immunotoxins in which a circularly permuted ligand is joined (preferably fused) to one terminus of the immunotoxin while another targeting ligand (e.g. an antibody, a circularly permuted growth factor, or another circularly permuted ligand) is inserted in the other terminus of the toxin. Thus, for example, a dual targeted PE might comprise a circularly permuted IL4 substituted for domain Ia at the amino terminus of the PE and anti-Tac(Fv) inserted in domain III, between amino acid 604 and 609. Other antibodies may also be suitable. A number of other antibodies have been converted to single-chain immunotoxins, including anti-erbB2, B3, BR96, OVB3, anti-transferrin, Mik-β1 and PR1 (Batra et al., *Mol. Cell. Biol.*, 11: 2200–2205 (1991); Batra et al., *Proc. Natl. Acad. Sci. U.S.A.*, 89: 5867–5871 (1992); Brinkmann, et al. *Proc. Natl. Acad. Sci. U.S.A.*, 88: 8616–8620 (1991); Brinkmann et al., *Proc. Natl. Acad. Sci. U.S.A.*, 90: 547–551 (1993); Chaudhary et al., *Proc. Natl. Acad. Sci. U.S.A.*, 87: 1066–1070 (1990); Friedman et al., *Cancer Res.* 53: 334–339 (1993); Kreitman et al., *J. Immunol.*, 149: 2810–2815 (1992); Nicholls et al., *J. Biol. Chem.*, 268: 5302–5308 (1993); and Wels, et al., *Cancer Res.*, 52: (6310–6317 (1992)).

Chimeric CP Ligand-Antibody Molecules

This invention also provides chimeric proteins comprising circularly permuted ligands joined (preferably by fusion) to an antibody. The antibody component of the fusion protein may specifically bind antigens characteristic of certain antigen-positive cancer cells (e.g., the Le$^y$ related antigen recognized by monoclonal antibodies B3, BR96, or the erb2 protein recognized by the e23 and other antibodies (Id.) while the circularly permuted ligand specifically binds immune cells bearing the particular receptor for the ligand (e.g. cells bearing IL2 or IL4 receptors). The circularly permuted bifunctional fusion protein thus acts to enhance the interaction between cancer cells and components of the immune systems and binds with higher affinity compared to the bifunctional fusion protein containing the native (unpermuted) ligand.

The antibodies used in the chimeric molecule include various forms of modified or altered antibodies, such as an intact immunoglobulin, an Fv fragment containing only the light and heavy chain variable regions, an Fv fragment linked by a disulfide bond, an Fab or (Fab)'$_2$ fragment containing the variable regions and parts of the constant regions, a single-chain antibody, a single domain of an antibody, and the like (Bird et al., *Science* 242: 424–426 (1988); Huston et al., *Proc. Nat. Acad. Sci. U.S.A.* 85:

5879–5883 (1988); Brinkmann, et al. *Proc. Nat. Acad. Sci. U.S.A.,* 90: 7538–7542 (1993). The antibody may be of animal (especially mouse or rat) or human origin or may be chimeric (Morrison et al., *Proc Nat. Acad. Sci. U.S.A.* 81: 6851–6855 (1984)) or humanized (Jones et al., *Nature* 321: 522–525 (1986), and published UK patent application #8707252). Methods of producing antibodies suitable for use in the present invention are well known to those skilled in the art and can be found described in such publications as Harlow & Lane, *Antibodies: A Laboratory Manual,* Cold Spring Harbor Laboratory (1988), and Asai, *Methods in Cell Biology Vol. 37. Antibodies in Cell Biology,* Academic Press, Inc. N.Y. (1993). region.

An exemplary single chain antibody is B3(Fv), the Fv fragment of antibody B3. This antibody binds a carbohydrate antigen in the Le$^y$ family which is found on the surface of many carcinomas of the colon, stomach, prostate, bladder, ovaries, breast and lung as well as some epidermoid carcinomas. Other antibodies of interest include BR96 (Friedman et al., *Cancer Res.,* 53: 334–339 (1993), e23 to erbB2 (Batra et al, *Proc. Natl. Acad. Sci. U.S.A.,* 89: 5867–5871 (1992)), PR1 in prostate cancer (Brinkmann et al., *Proc. Natl. Acad. Sci. U.S.A.,* 90: 547–551 (1993)), and K1 in ovarian cancer (Chang et al. *Int. J. Cancer,* 50: 373–381 (1992).

Means of joining (in particular fusing) antibodies to the circularly permuted ligands are well known to those of skill in the art. See, for example, Batra et al., *Mol. Cell. Biol.,* 11: 2200–2205 (1991), Chaudhary et al., *Nature,* 339: 394–397 (1989); Chaudhary et al. *Proc. Natl. Acad. Sci. U.S.A.,* 87: 1066–1070 (1990); and Brinkmann et al. *Proc. Natl. Acad. Sci. U.S.A.,* 88: 8616–8620 (1991) which are incorporated herein by reference.

Chimeric CP Ligand-Binding Protein Molecules

Other binding proteins besides antibodies may serve a similar function. Thus, this invention includes chimeric molecules comprising a circularly permuted ligand joined (preferably fused) to one or more binding proteins. These binding proteins may include antibodies, ligands, hormones, growth factors, circularly permuted ligands, circularly permuted hormones, circularly permuted growth factors, and other circularly permuted ligands.

To determine which circularly permuted ligands or chimeric molecules containing these factors are preferred, the proteins should be assayed for biological activity. Such assays, well known to those of skill in the art, generally fall into two categories; those that measure the binding affinity of the protein to a particular target, and those that measure the biological activity of the protein.

Binding affinity may be assayed by measuring the ability of the circularly permuted molecule to displace a native (unpermuted) ligand from its target substrate. This may be accomplished by labeling the native ligand and then incubating cells bearing the target receptor with a fixed amount of the labeled ligand and various concentrations of circularly permuted ligand. The amount of bound native ligand can be determined by detecting the amount of label bound to the target cell. Unlabeled native ligand can be run as a control. One of skill will recognize that selection of the target cell is determined by the particular ligand. The particular label is chosen to minimally interfere with the binding of the labeled native ligand. Suitable labels are well known to those of skill in the art and include, but are not limited to radioactive labels (e.g., $^{125}$I, $^{32}$P), fluorescent labels (e.g., fluorescein or rhodamine), and enzymatic labels (e.g., horseradish peroxidase). Examples of competitive binding assays may be found in Examples 1(c) and 2(c).

Biological Activity of CP Ligands and Chimeric Molecules

It is possible that the circularly permuted ligand might specifically bind the target receptor and yet fail to show any other biological activity (e.g., internalization within the cell). Therefore, it is often desirable to assay the biological activity of the protein as well as its binding specificity and affinity. Assays for biological activities of various kinds are well known to those of skill in the art. The particular assay depends on the particular activity of the molecule.

For example, where the protein is solely a circularized growth factor, the expected biological activity usually is an increase in growth or proliferation of cells bearing the protein's target receptors, but may be growth inhibition or cell differentiation. Conversely, where the circularized growth factor is fused to a cytotoxin, the expected biological activity would be a decrease in cell metabolic rate or possibly cell death. Changes in metabolic rate are easily measured as changes in the rate of uptake of a labelled metabolic substrate in the cells exposed to the test protein as compared to unexposed control cells. Generally, [$^3$H]-thymidine or [$^3$H]-leucine are used as labeled metabolic substrates although other labeled substrates are well known to those of skill in the art. Examples 1(d) and 2(d) detail assays for biological activity for circularly permuted IL4 and the IL4(38-37)-PE38Q fusion protein respectively.

Pharmaceutical Compositions and Diagnostics

The CP ligand and chimeric CP ligand compositions described herein are particularly well suited for targeting therapeutic agents or diagnostic agents to cells of interrest in vivo (i.e., target cells) since they exhibit, among other properties, high binding affinity for target cells. (As used herein, target cells are cells that bear on their surface molecules that specifically bind the circularly permuted ligand.) Thus, the compositions containing the present chimeric molecules or a cocktail thereof (i.e., with other proteins) can be administered in vivo for diagnostic applications or for therapeutic treatments.

A) Diagnostics

In one embodiment, this invention this invention provides for a method of detecting the presence or absence of a target cell (e.g. a tumor cell) or molecule (e.g. a ligand or ligand receptor). The method involves contacting the target cell or molecule with a chimeric molecule comprising a detectable label attached to a circularly permuted ligand that specifically binds to the target cell or molecule and detecting the presence or absence of the label.

The chimeric molecule may be administered in vivo or ex vivo. Thus, for example, a chimeric molecule comprising a circularly permuted ligand (e.g. IL4) attached to a detectable label may be administered to an organism (e.g. by intravenous injection). The chimeric CP ligand-label molecule preferentially associates with target cells bearing the a molecule to which the circularly permuted ligand specifically binds. The bound molecule may then be detected by a variety of non-invasive means. These include, but are not limited to tomography employing radio-opaque labels, NMR scanning employing paramagnetic labels, and scintillography employing radionuclides with scintillography being the particularly preferred method.

The chimeric molecule may be administered ex vivo to detect a target cell or molecule in a biological sample. The biological sample is contacted with the CP ligand-label chimeric molecule and bound chimeric molecules are detected. Means of detecting bound label molecules are well known by those of skill in the art. For example, in one approach, the biological sample is immobilized and contacted with the chimeric molecule. Immobilized chimeric molecule is detected by detesting the immobilized detectable label.

The biological sample may be any biological fluid or tissue isolated from an organism. Typical biological samples, include, but are not limited to urine, saliva, cerebrospinal fluid, semen, blood, plasma, soft tissue biopsies, bone marrow biopsies and the like. The sample is typically taken from a human patient, but the chimeric CP ligand-label molecules may be used to detect target cells or molecules in samples from any mammal, such as mice, dogs, cats, sheep, cattle, pigs, rabbits, and the like. The sample may be pretreated as necessary by dilution in an appropriate buffer solution or concentration if desired. Any of a number of standard aqueous buffer solutions, employing one of a variety of buffers, such as phosphate, Tris, or the like, at physiological pH can be used.

Detectable labels suitable for use in the chimeric molecules of this invention include any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, green fluorescent protein, and the like), radiolabels (e.g., $^3$H, $^{125}$I, $^{35}$S, $^{14}$C, or $^{32}$P), enzymes (e.g., horse radish, peroxidase, alkaline phosphatase and others commonly used in an ELISA), and colorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing; the colored label.

B) Pharmaceutical Compositions

In therapeutic applications, circularly permuted ligands, chimeric molecules comprising circularly permuted ligands, and various compositions containing these molecules are administered to a patient suffering from a disease, in an amount sufficient to cure or at least partially arrest the disease, or ameliorate its complications. An amount adequate to accomplish this is defined as a "therapeutically effective dose." Amounts effective for this use will depend upon the severity of the disease and the general state of the patient's health.

Among various uses of the cytotoxic chimeric molecules of the present invention are included a variety of disease conditions caused by specific human cells that may be eliminated by the toxic action of the protein. One preferred application is the treatment of cancer, such as by the use of TGFα or IL4 or IL6 or IGF1 as the circularly permuted ligand or of autoimmune conditions such as graft-versus-host disease, organ transplant rejection, type I diabetes, multiple sclerosis, rheumatoid arthritis, systemic lupus erythematosus, myasthenia gravis and the like caused by T and B cells. The fusion proteins may also be used in vitro, for example, in the elimination of harmful cells from bone marrow before transplant.

The circularly permuted ligand-toxin chimeric molecules of the present invention are particularly well suited for use in the inhibition of the growth of tumor cells in vivo. As described in Example 10, the circularly permuted ligand-toxin fusion proteins of the present invention show greater specific binding affinity and target cell toxicity as compared to native ligand-toxin fusion proteins. The increased binding affinity and toxicity allow the circularly permuted ligand-toxin fusion proteins to be administered at lower dosages while achieving the same therapeutic efficacy as the native ligand-toxin fusion proteins. Alternatively, administration at the same dosages results in prolonged therapeutic efficacy as the fusion proteins must be cleared from the circulation to a lower concentration before they cease to show significant efficacy. In addition, since the increased binding affinity and cytotoxicity is mediated by specific binding to the target cell, the increased therapeutic efficacy is not accompanied by an increase in undesired side effects due to non-specific binding and cytotoxicity.

The circularly permuted ligand portion of the chimeric molecule is chosen according to the intended use. Proteins on the membranes of T cells that may serve as targets for the circularly permuted ligands include CD2 (T11), CD3, CD4 and CD8. Proteins found predominantly on B cells that might serve as targets include CD10 (CALLA antigen), CD19 and CD20. CD45 is a possible target that occurs broadly on lymphoid cells. These and other possible target lymphocyte target molecules for the circularly permuted ligand proteins are described in *Leucocyte Typing III*, A. J. McMichael, ed., Oxford University Press (1987). Antigens found on cancer cells that may serve as targets for the circularly permuted ligand proteins include carcinoembryonic antigen (CEA), the transferrin receptor, P-glycoprotein, c-erbB2, Le$^y$ and antigens described in the Abstracts of the Third International Conference on Monoclonal Antibody Immunoconjugates for Cancer, San Diego, Calif. (1988). Those skilled in the art will realize that circularly permuted ligands may be chosen that bind to receptors expressed on still other types of cells as described above, for example, membrane glycoproteins or ligand or hormone receptors such as epidermal growth factor receptor and the like.

The chimeric molecules and pharmaceutical compositions of this invention are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is, recognized that the fusion proteins and pharmaceutical compositions of this invention, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The chimeric molecules and pharmaceutical compositions of this invention are particularly useful for parenteral administration, such as intravenous administration or administration into a body cavity or lumen of an organ. The compositions for administration will commonly comprise a solution of the circularly permuted ligand fusion protein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 100 mg per patient per day. Dosages from 0.1 up to about 1000 mg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980).

Single or multiple administrations of the compositions may be administered depending on the dosage and frequency as required and tolerated by the patient. In any event, the composition should provide a sufficient quantity of the proteins of this invention to effectively treat the patient.

Diagnostic Kits

In another embodiment, this invention provides for kits for the treatment of tumors or for the detection of target cells or target molecules in vivo or ex vivo. Kits will typically comprise a circularly permuted ligand and/or a chimeric molecule comprising a circularly permuted ligand of the present invention (e.g. CP IL4, CP IL4-label, CP IL4-cytotoxin, CP IL4-antibody, etc.). In addition the kits will typically include instructional materials disclosing means of use of the circularly permuted ligand or chimeric molecule (e.g. as a cytotoxin, for detection of tumor cells, to augment an immune response, etc.). The kits may also include additional components to facilitate the particular application for which the kit is designed. Thus, for example, where a kit contains a chimeric molecule in which the effector molecule is a detectable label, the kit may additionally contain means of detecting the label (e.g. enzyme substrates for enzymatic labels, filter sets to detect fluorescent labels, appropriate secondary labels such as a sheep anti- mouse-HRP, or the like). The kits may additionally include buffers and other reagents routinely used for the practice of a particular method. Such kits and appropriate contents are well known to those of skill in the art.

The following examples are offered by way of illustration and are not to be construed as limiting the invention as claimed in any way.

EXAMPLES

The oligonucleotide primers used in the following examples are listed in Table 1 and in SEQ ID NO:6 through SEQ ID NO:49, respectively.

TABLE I

Sequence of oligonucleotide primers used in Examples 1 through 6. The sequences are listed in the 5' to 3' direction from left to right.

| Primer | Sequence |
|---|---|
| BK24 | A-ATA-CGA-CTC-ACT-ATA-G |
| BK50 | GGC-ACC-GTT-GCG-AAT-CCG-GCC-GCG |
| BK54 | TGC-TTT-ACG-GGC-TAC-GCC-CAG-GAC-CAG |
| BK55 | GGG-ACC-TCC-GGA-CGA-TTT-GCC-TGA-GGA-GAC-GGT-GAC-CTC-GGT-ACC-TTG-GCC-CCA-GTA |
| BK56 | GGG-ACC-TCC-AGC-TTT-ACT-CTC-GAG-CTT-TGT-CCC-CGA |
| BK63 | CAC-CGT-CCA-GTT-CTG-CGT-GCC |
| BK78 | ATA-CGA-CTC-ACT-ATA-GGG-AGA |
| BK83 | GGG-CAT-AAA-CCC-GGG-CAT-AAA-ACG-CAT-GCA-CCT-ACT-TCA-AGT-TCT-ACA-AAG |
| BK84 | TCA-AGC-TGA-ATT-CTA-GGT-GAG-TGT-TGA-GAT-GAT-GCT-TTG-ACA |
| BK87 | CGG-CCA-CGA-TGC-GTC-CGG-CGT |
| BK96 | GGG-CTT-GGA-TCC-CCC-CCC-ACC-TGA-ACC-TCC-TCC-CCC-GCT-CGA-ACA-CTT-TGA-ATA-TTT |
| BK97 | GAG-GTC-GGA-TCC-GGC-GGA-GGC-GGA-TCT-GGC-GGA-GGT-GGC-TCG-GGC-GGC-AGC-CTG-GCC-GCG |
| BK-110 | TGT-TGC-TCC-GGA-GGT-AAC-GGT-GGG-CAC-AAG-TGC-GAT-ATC-ACC |
| BK-111 | CTT-GTG-CCC-ACC-GTT-ACC-TCC-GGA-CGA-ACA-CTT-TGA-ATA-TTT-CTC |
| BK-112 | CTC-AGT-TGA-AGC-TTT-GGA-GGC-AGC-AAA-GAT-GTC |
| BK-113 | TTT-GCT-GCC-CAT-ATG-AAC-ACA-ACT-GAG-AAG-GAA |

TABLE I-continued

Sequence of oligonucleotide primers used in Examples 1 through 6. The sequences are listed in the 5' to 3' direction from left to right.

| Primer | Sequence |
|---|---|
| BK-114 | ACT-CTG-GTA-AGC-TTC-CTT-CAC-AGG-ACA-GGA |
| BK-115 | CCT-GTG-AAG-CAT-ATG-AAC-CAG-AGT-ACG-TTG-GAA-AAC |
| BK-116 | TAT-TCA-AAG-TAA-GCT-TCC-GGG-GGA-GGA-GGT-TCA |
| BK-117 | GGA-GAT-ATA-CAT-ATG-GAC-ACA-ACT-GAG-AAG-GAA |
| BK-132 | GTT-TAA-CTT-TAA-GCT-TCC-GGA-GGT-CCC-GAG-GAC-ACA-ACT-GAG-AAG-GAA |
| BK-133 | CTC-GGG-ACC-TCG-AGC-TCA-TTT-GGA-GGC-AGC-AAA-GAT |
| BK-135 | ACA-CTC-ACC-GGA-GGT-AAC-GGT-GGG-GCA-CCT-ACT-TCA-AGT-TCT |
| BK-136 | AAA-CTG-AAT-TCA-AGC-TTA-CCT-GGT-GAG-TTT-GGG-ATT |
| BK-137 | AAA-CTC-ACC-CAT-ATG-CTC-ACA-TTT-AAG-TTT |
| BK-138 | AGG-TGC-CCC-ACC-GTT-ACC-TCC-GGT-GAG-TGT-TGA-GAT-GAT |
| BK-139 | GAG-GGC-GGA-GGA-AAC-GGA-GGT-GGG-GCA-CCC-GCC-CGC-TCG-CCC |
| BK-140 | TTC-TAG-AAT-TCA-AGC-TTA-CTC-AGC-AGC-AGT-GTC-TCT |
| BK-141 | ACT-GCT-GCT-CAT-ATG-GAT-GAA-ACA-GTA-GAA-GTC |
| BK-142 | GGG-TGC-CCC-ACC-TCC-GTT-TCC-TCC-GCC-CTC-CTG-GAC-TGG-CTC-CCA |
| BK-143 | GCC-TGC-AGC-CAT-ATG-GCA-CCC-GCC-CGC-TCG-CCC-AGC-CCC |
| BK-144 | CTC-ATG-AAT-TCA-AGC-TTA-CTC-CTG-GAC-TGG-CTC-CCA-GCA-GTC |
| BK-149 | AAT-TCA-AGC-TTC-ACG-TGT-GAG-TTT-GGG-ATT-CTT |
| BK-150 | AAT-TCA-AGA-AGC-TTC-TGC-AGC-AGT-GTC-TCT-ACT |
| BK-151 | CTG-TGC-ACC-CAT-ATG-ACC-GTA-ACA-GAC-ATC |
| BK-152 | GAT-GTC-GTA-AGC-TTT-CAA-CTC-GGT-GCA-CAG |
| BK-153 | ACA-GTG-CAG-CAT-ATG-ACC-CCC-CTG-GGC-CCT-GCC-AGC |
| BK-154 | AAT-CTA-AGC-TTG-GGG-CTG-GGC-AAG-GTG-GCG-TAG |
| BK-155 | GGG-GGC-GGA-GGA-AAC-GGA-GGT-GGG-ACC-CCC-CTG-GGC-CCT-GCC |
| BK-156 | CTG-CAA-AGC-TTG-GCT-GGG-GCA-GCT-GCT |
| BK-157 | TGC-CCC-AGC-CAT-ATG-CTG-CAG-CTG-GCA-GGC-TGC |
| BK-158 | GGT-CCC-ACC-TCC-GTT-TCC-TCC-GCC-GGG-CTG-GGC-AAG-GTG-GCG |
| VK116 | TGG-CGC-GGT-TTC-TAT-ATC-GCC |
| VK281 | GGC-CGG-TCG-CGG-GAA-TTC-TTA-GAG-CTC-GTC-TTT-CGG-CGG-TTT-GCC-GGG |

Example 1

Circularly Permuted IL4: Preparation and Biological Activity a) Construction of mutant plasmids pRKL4038 and pRKL4105

To make the mutant plasmids pRKL4038 and pRKL4105 encoding IL4(38-37) and IL4(105-104) respectively, the DNA sequence encoding recombinant IL4 was circularly permuted by polymerase chain reaction (PCR). The plasmid pGEM-7f (J. Biol. Chem. 268: 14065–14070 (1993)), designated herein as pRKL4, encoding native IL4 was used for a template. All amplification primers are listed in Table 1. The primers were made using a synthetic oligonucleotide synthesizer by Bioserv (Gaithersburg, Md., U.S.A.).

PCR was performed using the Gene-Amp kit (Perkin Elmer, USB, Cleveland Ohio, U.S.A.) according to the protocol supplied with the kit. Plasmids were purified using the Qiagen TIP-500 kit (Qiagen, Chatsworth, Calif., U.S.A.) and Promega magic minipreps (Promega, Madison, Wis., U.S.A.) according to the protocols supplied with the kits.

IL4 codons 1–37 were amplified using primers BK-110 and BK-112. The 5' end of the fragment encoded a GGNGG linker (SEQ ID NO:50) and the 3' end contained a HindIII site. IL4 codons 38–129 were amplified using BK-113 and BK-111. The 5' end contained an NdeI site and the 3' end encoded the GGNGG linker (SEQ ID NO:50). Since the 5' end of the first fragment is complementary to the 3' end of the second fragment, the 2 fragments (after partial purification on LMP agarose) could be used as an overlapping template in a 3rd PCR reaction using primers BK-113 and BK-112. The amplified fragment, cut with NdeI and HindIII, encodes IL4 codons 38–129, GGNGG (SEQ ID NO:50), and IL4 codons 1–37.

Figure 3A:
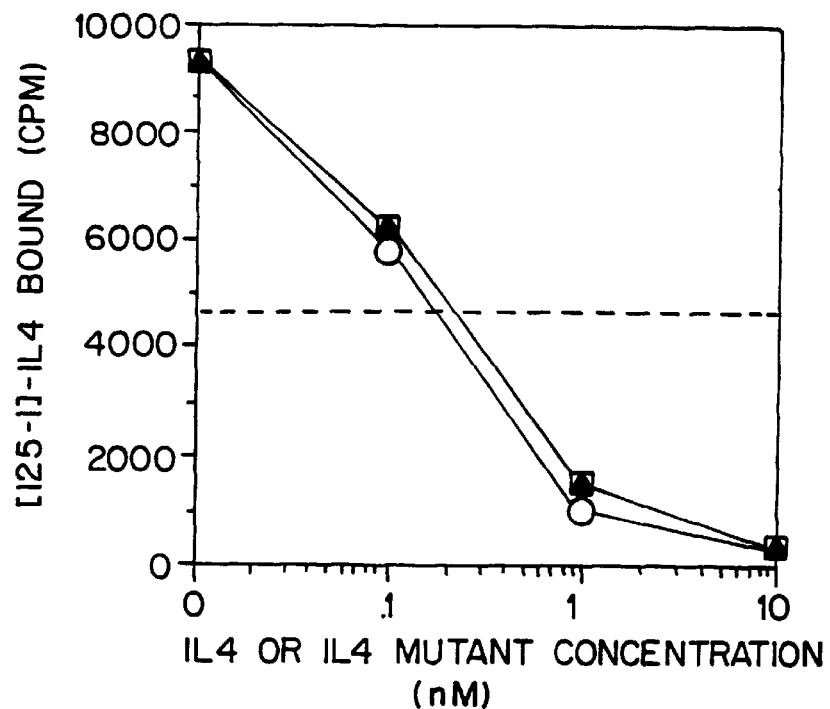

IL4 can also be circularly permuted at other residues. IL4 codons 1–104 of pRKL4 were amplified using BK-110 and BK-114, while codons 105–129 were amplified using BK-115 and BK-111. Regions encoding the GGNGG linker (SEQ ID NO:50) are the same as above. In the 3rd PCR reaction the overlapping template was amplified using BK115 and BK114. The amplified fragment, cut with NdeI and HindIII, produces a fragment encoding IL4 codons 105–129, GGNGG (SEQ ID NO:50), and IL4 codons 1–104.

The NdeI-HindIII fragments were subcloned into pRKL4 to produce the plasmids pRKL4038 and pRKL4105 encoding IL4(38-37) and IL4(105-104) respectively. These plasmids which encode the circularly permuted growth-factor carry a T7 promoter, a transcription terminator at the end of the open reading frame of the protein, an f1 origin of replication, and a gene for ampicillin resistance.

The entire coding region of each plasmid was sequenced using the Taq Dyedeoxy terminator cycle sequencing kit in conjunction with an automated sequencer (Applied Biosystems, Inc., Foster City, Calif., U.S.A.).

b) Protein expression and purification

To produce the circularly permuted molecules, *E. coli* BL21 (λDE3) cells were transformed (2 ng/100 μl of cells) with plasmid pRKL4038 or plasmid pRKL4105, incubated on ice 30 minutes, incubated at 42° C. for 1 minute, mixed with SOC media (900 μl/100 μl cells), shaken at 37° C. for 1 hour and then spread or L8-AMP plates.

The cells were cultured in superbroth containing ampicillin (100 μg/ml), glucose (5 mg/ml) and extra $MgSO_4$ (1.6 mM). At an $OD_{650nm}$ of about 3, isopropyl-β-D-thiogalactopyranoside (IPTG, USB, Cleveland, Ohio, U.S.A.) was added to a final concentration of 1 mM, and protein expression induced for 90–120 minutes. The harvested cell paste from 1L of culture was resuspended in 360 ml TES (50 mM Tris-HCl, pH 8.0, 20 mM EDTA, and 0.1 M NaCl) and lysozyme (13 ml of 5 mg/ml). After incubating for 30 minutes at 22° C., DNAse (0.8 mg in 0.8 ml $H_2O$) was added and, after shaking and allowing to stand at 22° C. for 30 minutes, the mixture was resuspended and centrifuged. The pellet was resuspended in 360 ml TES+40 ml 25% Triton X-100, incubated at 22° C. for 10 minutes and centrifuged. The pellet was washed two or three more times by resuspension in 360 ml TES+40 ml 25% Triton X-100 and centrifugation, then washed four times by resuspension in 360 ml TES and centrifugation. All resuspensions were performed using a tissuemizer (Thomas Scientific, Swedesboro, N.J., U.S.A.) at 22° C. and centrifugations were performed at 4° C. in a GSA rotor (Sorvall, Wilmington, Del., U.S.A.) at 13,000 RPM for 30–50 minutes.

The purified inclusion body protein (~120 mg) was resuspended by sonication in 12 ml of 7M guanidine:HCl containing 0.1 M Tris, pH 8, 2 mM EDTA, and 65 mM dithioerythritol (DTE) (Sigma, St. Louis, Mo., U.S.A.) and incubated 8–24 hr at 22° C. The denatured-reduced protein was clarified by centrifugation and diluted 100-fold into cold refolding buffer containing 0.1 M Tris, pH 8.0, 0.5 M L-arginine, 2 mM EDTA, and 0.9 mM oxidized glutathione (GSSG) (Sigma, St. Louis, Mo., U.S.A.).

After incubation at 10° C. for 36–48 hours, the clear solution was dialyzed against 0.02 M NaOAc (pH ~4.8) to a conductivity <5.0 mM NaCl. The refolded dialyzed protein was clarified by filtration through a 0.45 μ filter and loaded onto ~10 ml of CM fast flow cation exchange resin (Pharmacia-LKB, Piscataway, N.J., U.S.A.). The column was washed with equilibration buffer (0.02 M NaOAc, pH 4.8) and eluted with equilibration buffer containing 0.5 M NaCl.

The IL4 mutants were further purified by elution from an anion exchange column (Mono-Q, Pharmacia-LKB, Piscataway, N.J., U.S.A.) using a linear NaCl gradient in equilibration buffer. Finally, the protein containing fractions were subjected to size exclusion chromatography using a TSKG2000SW column (60×0.75 cm), Tosohaas, Montgomeryville, Pa., U.S.A.) equilibrated with phosphate buffered saline (PBS) Protein concentration was determined by the Bradford Coomassie plus assay (Pierce Chemical Co., Rockford, Ill., U.S.A.) using bovine serum albumin as a standard. Fractions were selected based on their purity by SDS-PAGE.

Purity of the mutant circularly permuted IL4 molecules was ascertained by SDS-PAGE. Each sample was run on 10–20% tricine gels (Novex, San Diego, Calif.) under reducing and non-reducing conditions. The purified proteins were shown to be greater than 95% pure. Under reducing conditions the gel retention of IL4, IL4(38-37), and IL4(105-104), which are 130, 136, and 135 amino acids in length, respectively was as expected. Under non-reducing conditions the band corresponding to IL4(105-104) migrated at a slightly slower rate than expected.

The amino terminal sequence of each circularly permuted protein, including the initiator methionine, was confirmed by amino acid sequence analysis (M. Lively, Wake Forest University, Winston-Salem, N.C., U.S.A.).

FIG. 2 shows a schematic three dimensional diagram of IL4 and circularly permuted mutants IL4(38-38) and IL4 (105-104). The three dimensional structure of IL4, based on the NMR coordinates (Powers et al. *Science,* 256: 1673–1677 (1992); Powers et al. *Biochem.,* 32: 6744: 6762 (1993)) kindly provided by M. Clore was converted to the schematic form shown in FIG. 2(A) by the Molscript Program (Luger et al. *Science,* 243: 206–210 (1989), kindly provided by Dr. P. Kraulis. The numbering system used here is based on the 129 amino acid mature IL4 protein, of SEQ ID NO:2 which, in recombinant form, is preceded by Met (Redfield, et al., *Biochemistry,* 30: 11029-11-35(1991)).

The structures of IL4(38-37) in FIG. 2(B) and IL4(105-104) in FIG. 2(C) were based on that of IL4. IL4(38-37) consisted of Met followed by amino acids 38–129, GGNGG (SEQ ID NO:50), amino acids 1–37 and a C-terminal alanine. IL4(105-104) consisted of Met followed by amino acids 105–129, GGNGG (Seq. Id. No. 50) and 1–104. For cloning purposes, each IL4 mutant contained alanine at the new C-terminus. This alanine was residue 104 for IL4(105-104) and constituted an extra residue for IL4(38-37).

c) Binding Affinity of Circularly Permuted IL4

The binding affinity of the circularly permuted IL4 is a measure of the ability of the protein to assume the conformation of native IL4 since it is expected that an incorrectly folded protein will have lost some measure of its binding affinity. To assess their binding affinity, the circularly permuted IL4 molecules were compared to native IL4 in their ability to displace labeled native IL4 ([$^{125}$I]-IL4) from IL4 receptor-bearing cells (FIG. 3(A)).

IL4 was iodinated using the method described by Debinski et al. *J. Biol. Chem.,* 268: 14065–14070 (1993). Then different concentrations of IL4 (O), IL4(38-37) (▲) or IL4(105-104) (□) were incubated with 0.5 nM [$^{125}$I]-IL4 and 2.5×10⁶ H9 cells in 126λ of media (RPMI containing 10% FBS). After 1–2 hours at 4° C., the cells were centrifuged through phthalate oil and the pellet analyzed in a gamma counter (FIG. 3(A)). The $EC_{50}$, the calculated concentration of protein necessary for 50% displacement of IL4, was 0.19 nM for IL4, 0.22 nM for IL4(38-37), and 0.21 nM for IL4 (105-104). Thus the binding activity of the circularly permuted IL4 mutants was similar to that of IL4. Similar results were found in the displacement of [$^{125}$I]-IL4 from the B-cell line DAUDI.

To determine if the circularly permuted IL4 mutants world bind well if exposed to IL4 receptor-bearing cells at 4° C., but not at 37° C. the mutants were compared in competition with the cytotoxic activity of the IL4-toxin IL4-PE$^{4B}$ (see Debinski et al. *J. Biol Chem.*, 268: 14065–14070 (1993)).

On A431 based IL4 receptor-bearing epidermoid cells, 1.2 nM IL4-PE$^{4B}$ inhibited protein synthesis 98%; 50% of this inhibition was eliminated (binding was out competed) by 1.3 nM, 1.2 nM, and 1.4 nM of IL4, IL4(38-37), IL4(105-104) respectively. Thus, the circularly permuted variants bound well at 4° C. and 37° C. and also compete for IL4 internalization. These data strongly suggest that the secondary and tertiary structures of the circularly permuted IL4 proteins, particularly with regard to cysteine pairing, were very similar to that of IL4. This is in dramatic contrast to murine IL4 which does not bind at all to human IL4 receptors and yet differs only slightly in disulfide bond pairing (Carr et al., *Biochem.*, 30: 1515–1523 (1991)).

d) Proliferative Activity of Circularly Permuted IL4

It has previously been shown that mutations in human IL4 which prevent its proliferative activity often affect binding to a greatly diminished extent. Kruse et al., *EMBO J.*, 11: 3237–3244 (1992). It is therefore possible that circularly permuted IL4 mutants might bind to the IL4 receptor with full affinity, but be unable to transduce the signal which leads to proliferation. Thus it was desirable to determine the proliferative potential of circularly permuted IL4.

To determine the proliferative activity of the circularly permuted mutants, different concentrations of IL4, IL4(38-37), or IL4(105-105) were incubated with 6×10⁴ CTLL$^{hIL4R}$ cells in 200 μl of DMEM with 10% FBS for 6 hours and then incubated for 18 hours with [³H]-thymidine (0.5 μCi/well). These murine cells which are transfected with a human IL4 receptor cDNA proliferate in a specific manner when exposed to human IL4. Idzerda et al. *J. Exp. Med.*, 171: 861–873 (1993).

Figure 3B:
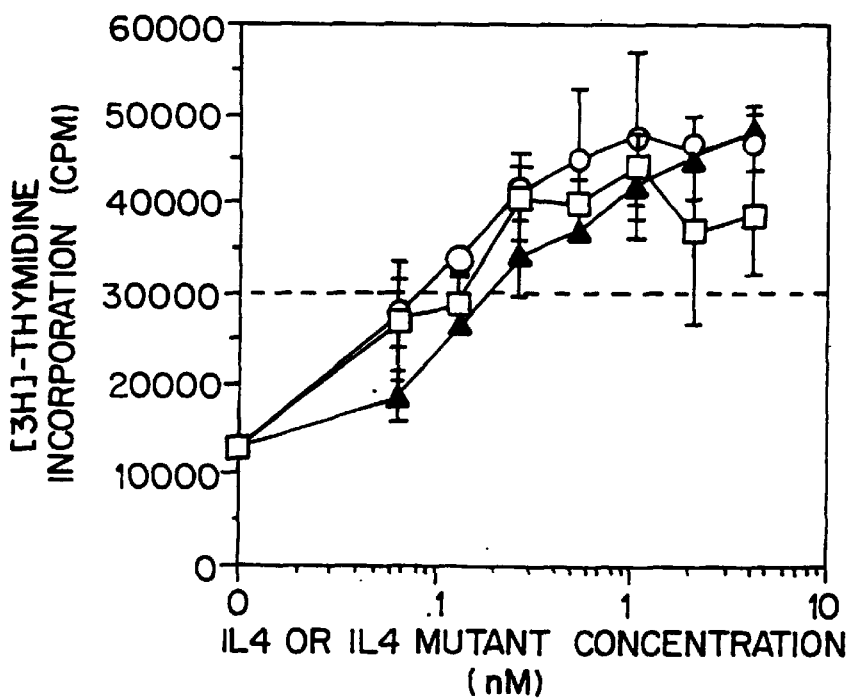

FIG. 3(B) shows [³H]-thymidine incorporation after 24 hours of exposure of the cell to different concentrations of IL4, IL4(38-37), and IL4(105-104). The concentration required for increasing the [³H]-thymidine incorporation to 30,000 counts per minute (cpm), which is approximately half-maximal, was 0.12 nM for IL4, 0.2 nM for IL4(105-104), and 0.24 nM for IL4(38-37). Thus the proliferative activity of the circularly permuted IL4 molecules was 50% to 100% of that of IL4, confirming that the three dimensional structure of the circularly permuted mutants was similar to that of IL4.

Example 2

Circularly Permuted IL4-Pseudomonas Exotoxin Fusion Protein: Preparation and Biological Activity.

a) Construction of plasmids pRKL4QRD and pRKL438QRD

DNA sequences encoding IL4(38-37) were prepared is described in Example 1. Plasmids pRKL4QRD and pRKL438QRD, encoding IL4-PE38QQRDSL and IL4(38-37)-PE38Q, respectively, were constructed by ligating the 0.4 Kb NdeI-HindIII fragment of pRKL4 or pRKL4038, encoding IL4 or IL4(38-37), respectively, to the 4.0 Kb HindIII-NdeI fragment of pRK79QRDE encoding anti-Tac (Fv)-PE38Q. PRK79QRDE was constructed by site directed mutagenesis and PCR mutagenesis at the C-terminus of PE. The resulting plasmids, pRKL4QRD and pRKL438QRD, encode IL4-PE38Q and IL4(38-37)-PE38Q respectively. IL4-PE38Q contains the toxin fused to the C-terminus of IL4, and IL4(38-37)-PE38Q contains the toxin fused to the C-terminus of IL4(38-37). In each case, the 6 amino acids ASGGPE (SEQ ID NO:57) connect the ligand to the toxin.

b) Plasmid expression and purification

Expression and purification of the plasmids pRKL4QRD and pRKL438QRD was performed as in Example 1.

c) Binding Affinity of Circularly Permuted IL4-toxin

Figure 4A:
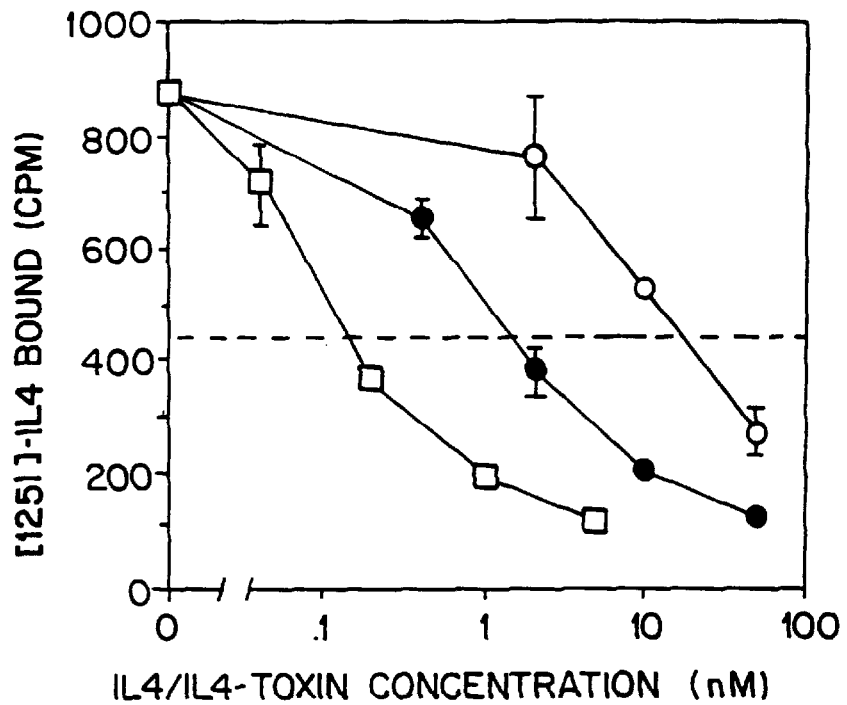

FIG. 4(A) shows the binding activity of circularly permuted IL4-PE fusion protein compared to the native IL4-PE fusion protein. DAUDI cells (1×10⁶ cells) in 200 μl aliquots of media (RPMI containing 10% FBS) were incubated at 4° C. for 1–2 hours with [$^{125}$I]-IL4 (0.1 nM) and different concentrations of IL4(□), IL4(38-37)-PE38Q (●) or IL4-PE38Q (○). Each cell aliquot was centrifuged over 150 μl of n-butylphthalate and the cell pellet counted in a τ counter. The $EC_{50}$, the concentration of protein needed for 50% displacement of [$^{125}$I]-IL4, was 0.14, 1.4 and 18 for IL4, IL4(38-37)-PE38Q, and IL4-PE38Q, respectively. FIG. 4(A) shows that the recombinant fusion toxin IL4(38-37) PE38Q was greater than 10 fold more potent than IL4-PE38Q in displacing [$^{125}$I]-IL4 from IL4 receptor bearing DAUDI cells.

d) Cytotoxicity of Circularly Permuted IL4-toxin

Figure 4B:
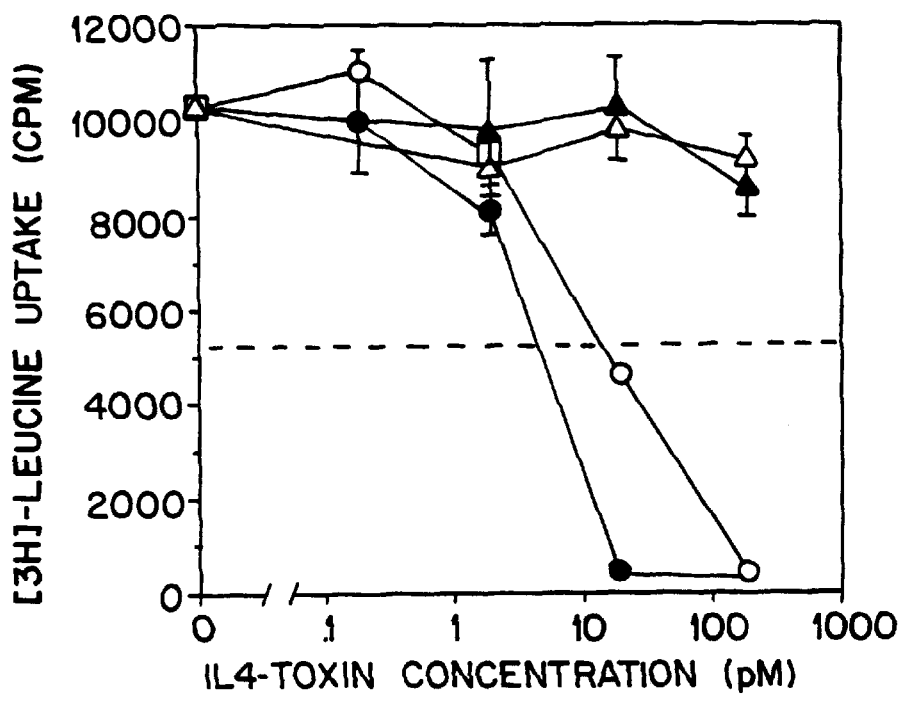

FIG. 4(B) shows the cytotoxic activity of IL4-PE. IL4 receptor-bearing ATAC-4 cells (Kreitman, et al. *Blood*, 83: 426–434 (1994)) were plated at 1–1.5×10⁴/well for 24 hours, and then incubated in 200 μl aliquots in DMEM containing 5% FBS for 24 hours at 37° C. with different concentrations of IL4(38-37)-PE38QQREL (●) or IL4-PE38Q (○). Cells were also incubated with IL4(38-37)-PE38Q (▲) or IL4-PE38Q (Δ) each combined with an excess (10 μg/ml) of IL4. The cells were then pulsed with [³H]-leucine 1 μCi/well for 3–6 hours, harvested and counted. The $IC_{50}$'s, the concentrations needed for 50% inhibition of protein synthesis, were 0.24 and 0.75 ng/ml for IL4(38-37)-PE38Q and IL4-PE38Q, respectively.

As shown in FIG. 4(B), the cytotoxic activity was specific for the IL4 receptor and was reversed by an excess of IL4. Toxins fused to circularly permuted forms of IL4 appear to constitute improved reagents for the in vivo treatment of IL4 receptor bearing tumors.

Example 3

Preparation of Circularly Permuted Ligand-Antibody Fusion Proteins.

Plasmid pULI9, encoding B3(Fv)-PE38KDEL (Brinkmann et al., *Proc. Natl. Acad. Sci. U.S.A.*, 89:3075–3079 (1992)) was separately amplified with VK116 and BK50, and then BK54 and VK281. The 2 amplified fragments were used as an overlapping template in a 3rd PCR reaction, using VK116 and VK281 as primers. The amplified fragment encodes PE amino acids 466–608 and the C-terminus KDEL (SEQ ID NO:62). The fragment was cut with EagI and EcoRI, and the 0.37 Kb fragment ligated to the 4.5 KB fragment of pULI9. The resulting plasmid, pRKB3F, was identical to pULI9 except codon 493 of PE, ATC, was replaced with ATT which eliminated a BamHI site.

Figure 5:
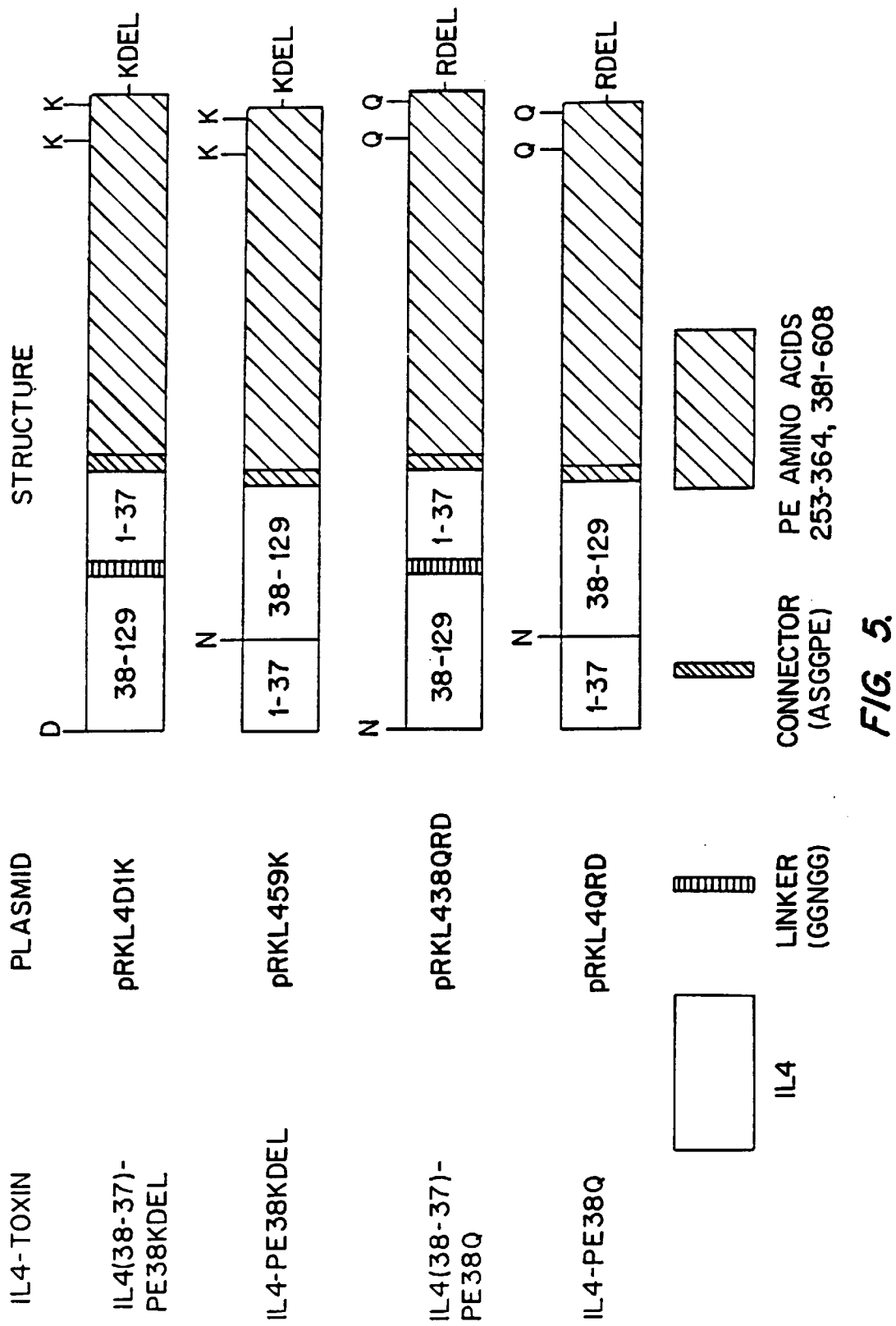
Figure 6A:
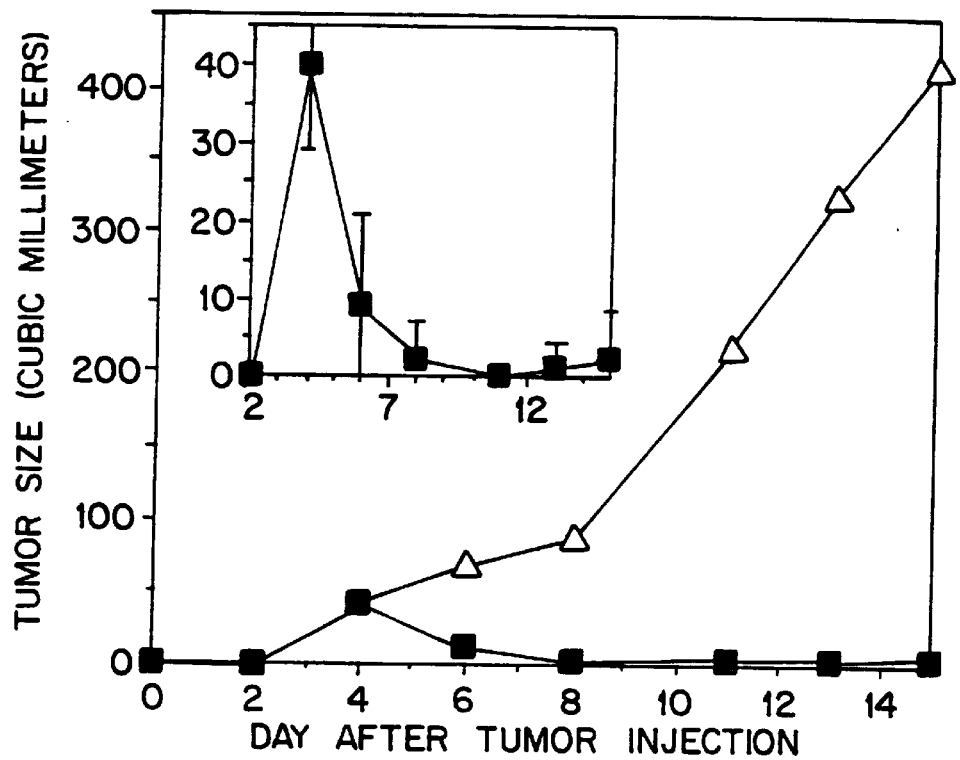
Figure 6B:
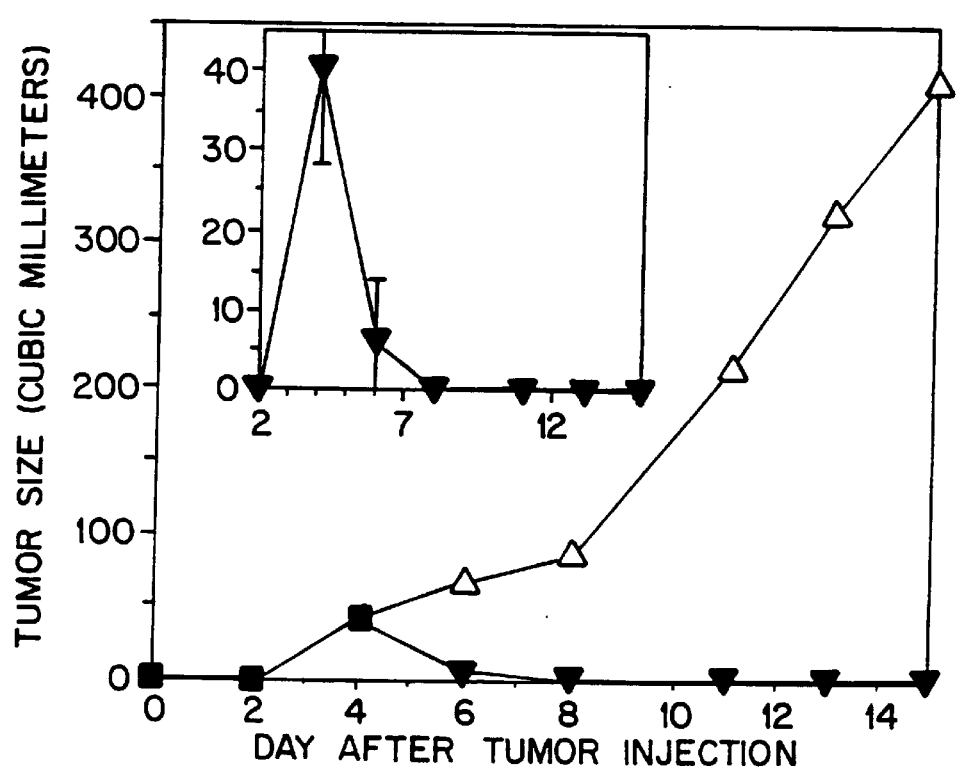
Figure 6C:
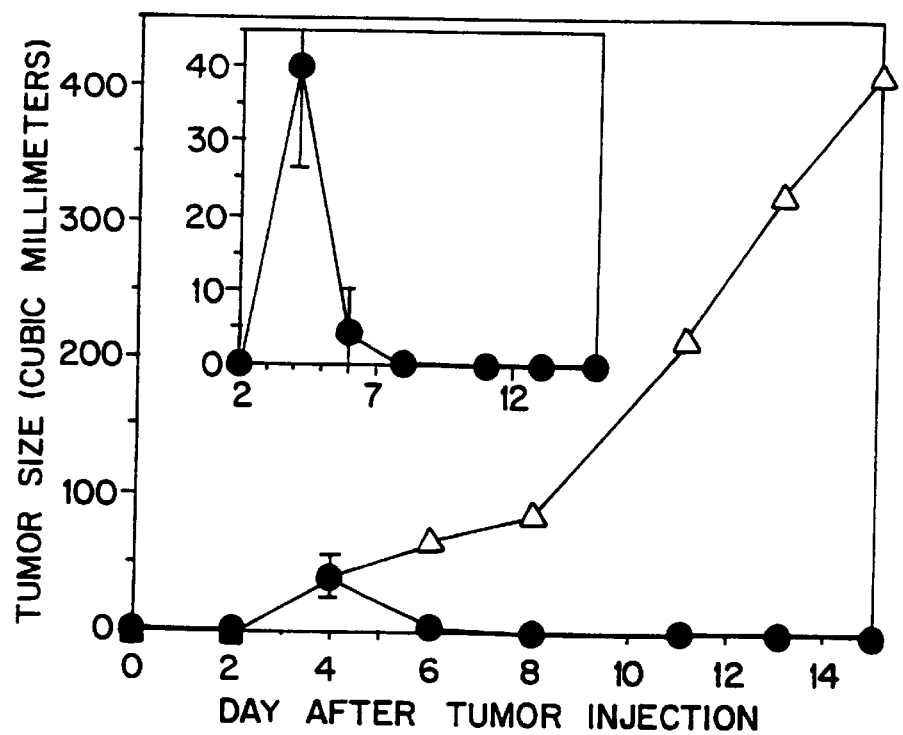
Figure 6D:
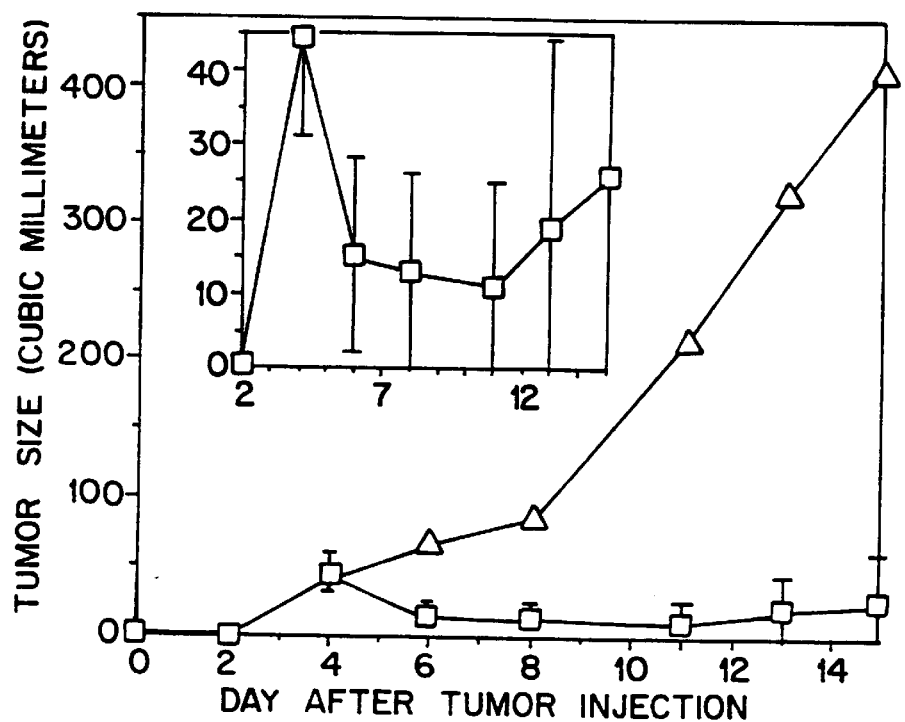
Figure 6E:
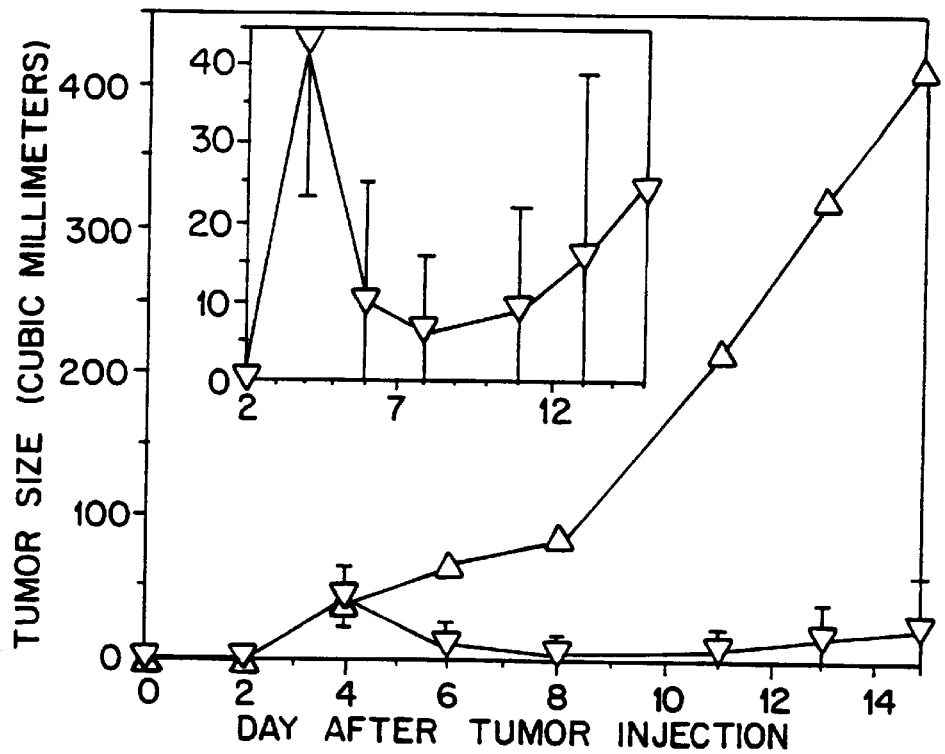
Figure 6F:
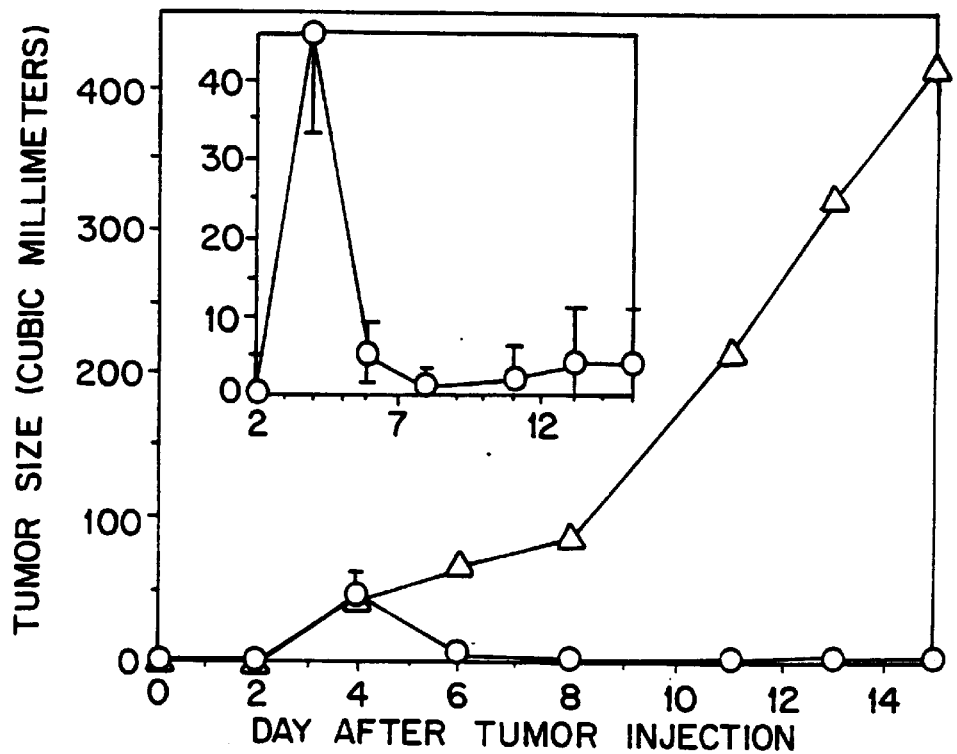

Plasmid pUL120, encoding B3(V$_H$)-PE38KDEL (Brinkmann et al., *J. Immunol.* 150:2774–2782 (1993)) was amplified with primers BK24 and BK55. The 0.41KB XBAI-HindIII fragment of the amplified DNA is ligated into the 4.0 KB HindIII-XbaI fragment of pRKB3F. The resulting plasmid, pRKB3H2, was identical to pUL120, except that codon 114 of B3($V_H$) (CTG) was replaced with GAG, resulting in a L114E mutation. Codons 112–113 were also changed from GGG-ACT to GGT-ACC, resulting in a new unique KpnI site. Plasmid pRKB3H2 was amplified with the primers BK97 and BK64, and the amplified DNA cut with BamHI and EcoRI. pRKL4EL, encoding IL4-ELKA was amplified using primers BK87 and BK96, and the amplified DNA cut with BglII and BamHI. The 0.51 KB BglII-BamHI fragment and the 1.1 KB BamHI-EcoRI fragment were then ligated to the 2.9 Kb BglII-EcoRI fragment of pRK79, which encodes anti-Tac (Fv)-PE38 (Kreitman et al., *Blood* 83:426–434 (1994)). The resulting plasmid, pRKL49K, encodes IL4, followed by the spacer $(GGGGS)_4$ (SEQ ID NO:55), and PE38KDEL.

Plasmid pRKL4038, encoding IL4 (38-37), was amplified using primers BK117 and BK64, and the DNA cut with NdeI and HindIII.

Plasmid pRKL49K was amplified by primers BK116 and BK63, and the DNA cut with HindIII and SacII. The 0.39 KB NdeI-HindIII fragment and the 0.45 Kb HindIII-SacII fragment were ligated to the 3.6 Kb NdeI-SacII fragment of pRK749K (Spence et al., *Bioconjugate Chem.* 4:63–68 (1993)). The resulting plasmid, pRKDG1K, encodes MD, amino acids 39–129 of IL4, GGNGG (SEQ ID NO:50), amino acids 1–37 of IL4, the spacer $AS(GGGGS)_4$ (SEQ ID NO:56), and PE38KDEL. Finally, pRKL4D1K was obtained by ligating the 0.45 KB XbaI-HindIII fragment of pRKL4DG1K to the 4.0 KB XbaI-HindIII fragment of PRK749K. The resulting plasmid pL4D1K differs from pRKL4DG1K in that it encodes the spacer ASGGPE (SEQ ID NO:57) instead of $AS(GGGGS)_4$ (SEQ ID NO:56).

Circularly permuted IL4 was connected to a single-chain Fv, in order to target IL4 receptor-bearing immune cells to antigen-positive cancer cells. Plasmid pRKL4D1K, which encodes IL4(38-37)-PE38KDEL, was amplified with primers BK-132 and BK-133. The amplified fragment encoded IL4(38-37) and contained a HindIII site at the 5' end and a SacI site at the 3' end. The 0.4 Kb HindIII-SacI fragment was then ligated to the 3.8 Kb SacI-HindIII fragment of pRKB3F. The resulting plasmid, pRKB3L438, encodes B3(Fv)-IL4(38-37).

The plasmid is introduced into *E. coli* BL21 (λDE3), expressed by induction with isopropythiogalactoside (IPTG), isolated and purified as described in Example 1.

Example 4

Preparation of Circularly Permuted IL4 Diphtheria Toxin Fusion Proteins

To make a diphtheria toxin molecule targeted by circularly permuted IL4, the 0.4 Kb NdeI-HindIII fragment of pRKL4D1K (see Example 3) was ligated to the 4.2 Kb HindIII-NdeI fragment of pVCDT1-IL2, which encodes DT388-IL2. Chaudhary, et al., *Bioch. Biophys. Res. Comm.,* 180: 545–551 (1991). The resulting plasmid pRKDTL438, encodes DT388-IL4(38-37).

The plasmid was introduced into *E. coli* BL21 (λDE3), expressed by induction with isopropythiogalactoside (IPTG), isolated and purified as described in Example 1.

Example 5

Preparation of Circularly Permuted IL2.

Plasmid pVCDT1-IL2, encoding DT388-IL2 (Chaudhary et al., *Biochem. Biophys. Res. Comm.* 180:545–551 (1991)), was amplified with BK-83 and BK-84, and cut with XmaI and EcoRI. The 0.42 Kb XmaI-EcoRI fragment was ligated to the 4.2 Kb XmaI-EcoRI fragment of pVCDT1-IL2. The resulting plasmid, pRKDL2, encodes a protein of sequence identical to that of $DAB_{389}IL2$ (Williams et al., *J. Biol. Chem.* 265:11885–11889 (1990)).

To make circularly permuted IL2, pRKDL2, encoding $DAB_{389}IL2$, was used as a template. IL2 codons 1–38 were amplified using primers BK-135 and BK-136. The 5' end of the amplified fragment encodes the GGNGG linker (Seq. Id. No. 50) and the 3' end contains a HindIII site. IL2 codons 39–127 were amplified using primers BK-137 and BK-138. The 5' end of this fragment contains an NdeI site and the 3' end encodes the GGNGG linker (SEQ ID NO:50). The overlapping fragments were then amplified in the 3rd PCR reaction using primers BK-137 and BK-136. The 0.4 Kb NdeI-HindIII fragment of this PCR product was ligated to the 3 Kb HindIII-NdeI fragment of pRKL4, which encodes IL4. The resulting plasmid, pRKL2039, encodes IL2(39-38), and contains a stop codon within the HindIII site. Plasmid pRKL2039 was then amplified with the T7 promotor primer BK-78 and BK-149. The 0.4 Kb NdeI-HindIII fragment, which does not contain a stop codon within the HindIII site, was ligated to the 4 Kb HindIII-NdeI fragment of pRKB3F. The resulting plasmid, pRKL2399K, encodes IL2(39-38)-PE38KDEL. The plasmid was introduced into *E. coli* BL21 (λDE3), expressed by induction with isopropythiogalactoside (IPTG), isolated and purified as described in Example 1.

Example 6

Preparation of Circularly Permuted GM-CSF and G-CSF.

To make circularly permuted GM-CSF or G-CSF, templates encoding the native forms of these molecules were first cloned from a spleen cDNA library using either primers BK-143 and BK-144 or BK-153 and BK-154, respectively. GM-CSF codons 1–35 were amplified using BK-139 and BK-140, while GM-CSF codons 36–127 were amplified using primers BK-141 and BK-142. The 5' end of the first fragment and the 3' end of the second fragment both encode for a GGGNGGG linker (SEQ ID NO:52). The overlapping products were amplified in the 3rd PCR reaction using primers BK-141 and BK-140. The 0.4 Kb NdeI-HindIII fragment, which contains a stop codon within the HindIII site, was then ligated to the 3 KB HindIII-NdeI fragment of PRKL4, resulting in pRKGM036, which encodes GM-CSF (36-35). Plasmid pRKGM036 were then amplified with primers BK-78 and BK-150, and the 0.4 Kb NdeI-HindIII fragment, which does not contain a stop codon within the HindIII site, was ligated to the 4 Kb HindIII-NdeI fragment of pRKB3F. The resulting plasmid, pRKGM369K, encodes GM-CSF(36-35)-PE38KDEL.

G-CSF codons 1–68 were amplified using primers BK-155 and BK-156, and codons 69–173 amplified using primers BK-157 and BK-158. The 5' end of the first fragment and the 3' end of the second fragment both encode the GGGNGGG linker (SEQ ID NO:52). The overlapping products were amplified in the third PCR, reaction using primers BK-157 and BK-156, and the 0.5 Kb NdeI-HindIII fragment ligated to the 4 Kb HindIII-NdeI fragment of pRKB3F. The resulting plasmid, pRKG699K, encodes G-CSF(69-68)-PE38KDEL.

The plasmid is introduced into *E. coli* BL21 (λDE3), expressed by induction with isopropythiogalactoside (IPTG), isolated and purified as described in Example 1.

Example 7

Synthesis of IL4(38-37)-PE38KDEL

The CP-IL4-toxin described in Example 2, IL4(38-37)-PE38Q is composed of IL4 amino acids 38–129, the linker GGNGG (SEQ ID NO:50), IL4 amino acids 1–37, the connector ASGGPE (SEQ ID NO:51), PE amino acids 253–364 and 381–608 with the K590Q and K606Q mutations, and the RDEL (SEQ ID NO:61) C-terminus (FIG. 5). The IL4(38-37)-PE38KDEL differs from IL4(38-37)-PE38Q in two ways. First, it contains the truncated toxin PE38KDEL, which consists of amino acids 253–364 and 381–608 of PE with the native lysine residues at positions 590 and 606, and it ends with KDEL (SEQ ID NO:60) instead of RDEL (SEQ ID NO:61). Secondly, IL4(38-37)-PE38KDEL contains aspartate replacing Asn38 immediately following the initiator methionine. PE38KDEL was particularly well suited for in vivo study in view of the antitumor data already accumulated with B3(Fv)-PE38KDEL, anti-Tac (Fv)-PE38KDEL, and anti-ErbB2(Fv)-PE38KDEL (Brinkmann et al. *Proc. Natl. Acad. Sci. U.S.A.*, 88: 8616–8620 (1991), Kreitman et al., *Blood*, 426–434 (1994), Batra et al. *Proc. Natl. Acad. Sci., U.S.A.*, 89: 5867–5871 (1992)).

A) Polymerase chain reaction

Polymerase chain reaction (PCR) was performed using the Gene-Amp kit (USB, Cleveland, Ohio, U.S.A.) by denaturing at 94° C. for one minute, annealing at 55° C. (unless otherwise stated) for 2 minutes, and polymerizing at 72° C. for 3 minutes. A total of 30 cycles were used, with a 10 second/cycle extension to polymerization. 5% (V/V) formamide was used in the PCR reactions. Primers were separated from PCR products using Centricon 100 (Amicon, Beverly, Mass.) and restricted without further purification. Plasmids were sequenced using a Dyedeoxy Terminator cycle sequencing kit and an automated sequencer (Applied Biosystems, Foster City, Calif.).

B) Plasmid construction

The composition of proteins encoded by pRKL4D1K, pRKL459K, pRKL438QRD and pRKL4QRD is diagramed in FIG. 5. The two circularly permuted(CP)IL4-toxins contain IL4 residues 38–129 connected through a GGNGG (SEQ ID NO:50) linker to IL4 residues 1–37. IL4(38-37)-PE38KDEL differs from IL4(38-37)-PE38Q in that it contains aspartate replacing asparagine at the N-terminus (just after the initiator methionine) to improve production. All four toxins contain the amino acids ASGGPE (SEQ ID NO:51) connecting the ligand to PE. The latter two toxins were described in Example 2.

pRKL4DG1K is an intermediate plasmid encoding IL4 (3E-37)-PE38KDEL with the amino acids AS(G$_4$S)$_4$ (SEQ ID NO:56) connecting amino acid 37 of IL4 to amino acid 253 of PE. pRKL4H1K is identical to pRKL4D1K except it encodes the amino acids HKN instead of D between the initiator methionine and residue 39 of IL4. pRKL4D1KM encodes IL4(38-37)-PE38KDEL$^{Asp553}$, which identical IL4 (38-37)-PE38KDEL except it contains the E553D mutation which abolishes ADP-ribosylation activity (Carroll, et al. *J. Biol. Chem.*, 262: 8707–8711 (1987)). pRKL29K encodes the immunotoxin IL2-PE38KDEL, which contains the irrelevant ligand, interleukin-2, having the same size as IL4. pVCDT1-IL2 encodes DT388-IL2 (Chaudhary et al., *Biochem. Biophys. Res. Commun.*, 180: 545–551 1991)). pRKB3F encodes B3(Fv)-PE38KDEL (Brinkmann et al. *Proc. Natl. Acad. Sci. U.S.A.*, 88: 8616–8620 (1991)). pWDMH4.38Q encodes hIL4-PE38QQR, which is identical to IL4-PE38Q except it ends with REDLR (SEQ ID NO:65) instead of RDEL (SEQ ID NO:61) (Debinski et al. *Int. J. Cancer*, 58: 744–748 (1994), Kreitman et al. *Biochemistry*, 33: 11637–11644 (1994)). pRKL49K encodes IL4-(G$_4$S)$_4$-PE38KDEL (see Example 2). pRK749K encodes anti-Tac (Fv)-PE38KDEL and pRK79KM encodes a E553D mutant of this protein (Kreitman et al. *Blood*, 426–434 (1994). pRKL4 encodes native IL4 (see Example 1). pRKL4038 encodes IL4(38-37) alone without the toxin.

In all recombinant toxins except IL4-(G$_4$S)$_4$-PE38KDEL, the sequence KAS at the end of the ligand is encoded by the sequence 5'-aaa-gct-ttc-3', which contains a HindIII site. The beginning of all ligands is encoded by a sequence (containing an NdeI site. An XbaI site exists 39 bases upstream from the coding regions of all plasmids. All PE-encoding plasmids contain a SacII site at codon 413 of PE.

pRKL4038 was prepared by ligating a fragment encoding CP-IL4 (encoded by the 0.38 Kb NdeI-HindIII fragment of pRKL438QRD) to the 3.0 Kb HindIII-NdeI fragment of pRKL4. To replace N$^{38}$ at the N-terminus with aspartate, pRKL4038 was amplified with the oligonucleotide primers BK117 (5'-gga-gat-ata-cat-atg-gac-aca-act-gag-aag-gaa-3', SEQ ID NO:25) and BK64 (3'-cgt-tat-tga-tcg-tat-tgg-gga-5', SEQ ID NO:58). To place a HindIII site at the 5' end of the toxin gene, pRKL49K was amplified with primers BK116 (5'-tat-tca-aag-taa-gct-tcc-ggo-gga-gga-ggt-tca-3', SEQ ID NO:24) and BK63 (3'-ccg-tgc-gtc-ttg-acc-tgc-cac-5', SEQ ID NO:11). This latter PCR step required an annealing temperature of 42–50° C. pRKL4DG1K was obtained by ligating the 0.39 Kb NdeI-HindIII fragment of the first product and the 0.45 Kb HindIII-SacII fragment of the second product to the 3.6 Kb SacII-NdeI fragment of pRK749K. pRKL4D1K was then obtained by ligating the 0.45 Kb XbaI-HindIII fragment of pRKL4DG1K to the 4.0 Kb HindIII-XbaI fragment of pRK749K. To place the amino acids HKN at the N-terminus, pRKL4038 was amplified with BK11B (5'-taa-gaa-gga-cat-atg-cat-aag-aac-aca-act-gag-aag-3') (SEQ ID NO:70) and BK64. pRKL4H1K was then obtained by ligating the 0.39 Kb NdeI-HindIII fragment to the 4.1 Kb HindIII-NdeI fragment of pRKB3F. pRKL4D1KM was obtained by ligating the 0.44 XbaI-HindII fragment of pRKL4DG1K to the 4.0 Kb HindIII-XbaI fragment of pRK79KM. pRKL.29K was obtained by ligating the 0.42 Kb NdeI-HindIII fragment of pVCDT1-IL2 to the 4.1 Kb HindIII-NdeI fragment of pRKB3F. pRKL459K was obtained by legating the 0.44 Kb XbaI-HindIII fragment of pWDMH4.38Q to the 4.0 Kb HindIII-XbaI fragment of pRK749K.

C) Plasmid expression and protein purification

Plasmids were expressed and proteins purified as described above in Example 1(b). Briefly, plasmids encoding IL4-toxins and control molecules were expressed in *E. coli* BL21(λDE3) and the insoluble inclusion bodies purified by washing with detergent containing Triton-X-100. The inclusion bodies were dissolved in denaturing solution containing 7 M guanidine:HCl and reduced with 65 mM dithioerythritol. The protein was renatured by 1:100 dilution into a redox buffer containing 0.9 mM oxidized glutathione and 0.5 M L-arginine and then purified by anion exchange and sizing chromatography. Recombinant proteins were >95% pure by SDS-PAGE.

Example 8

Effect of Modified N-Terminus on Growth of Transformed *E. coli*

As shown in Table 2, *E. coli*. BL21(λDE3) transformed with plasmid encoding the CP-IL4-toxin IL4(38-37)-PE38Q grew only 2% as well as the expression bacteria transformed with plasmid encoding the native IL4-toxin IL4-PE38Q or IL4-PE38KDEL which began with the amino acid sequence MHKCD (SEQ ID NO:71). A possible explanation for this important technical problem is that the new amino terminus (MNTTE) (SEQ ID NO:63) interacts with the *E. coli* in a manner which interfered with cell growth or reproduction. This problem was not solved by adding the first two amino acids of native IL4 (HK) to the N-terminus of IL4(38-37) to make MHKNTT . . . (SEQ ID NO:72), since, as shown in Table 2, E. coli expressing this construction also grew very poorly. However, when the asparagine at the amino terminus of IL4(38-37)-PE38KDEL was changed to aspartate so that the amino terminal sequence became MDTTE . . . (SEQ ID NO:69), bacterial growth was very good, reaching a level that was 40% that of native IL4-toxin. The N38D mutation has been used in IL4 previously to prevent hyperglycosylation during its expression in yeast (Powers et al., Biochemistry,* 32: 6744–6762 (1993), Curtis et al. *Prot. Struct. Funct. Genet.,* 11: 111–119 (1991), Vitetta et al. *J. Exp. Med.,* 166: 476–488 (1987)). The new N-terminus generated by circular permutation of the ligand leads to diminished bacterial growth and low protein expression, which is overcome by altering the amino terminus from MNTTE (SEQ ID NO:63) to MDTTE (SEQ ID NO:64).

with phytohemagglutinin (10 $\mu$g/ml) for 3 days and IL2 for 2 days. The cells ($4\times10^4$/well, 100 $\mu$l/well) were incubated with toxins in media consisting of 2% RPMI, 88% leucine-free RPMI and 10% FBS for ~40 hours, pulsed with [$^3$H]-leucine (1 $\mu$Ci/well) for 6–8 hours, harvested and counted. $IC_{50}$'s are the toxin concentrations necessary for 50% inhibition of protein synthesis. Experiments were performed in triplicate and the median of each triplicate used to calculate $IC_{50}$'s. Several independent experiments were conducted for each cell line.

B) Binding Activity of IL4(38-37)-PE38KDEL

To quantitate the improvement in binding affinity of the CF-IL4-toxin IL4(38-37)-PE38KDEL over the native IL4-toxin IL4-PE38KDEL, the IL4-toxins were tested for their ability to displace [$^{125}$I]-IL4 from the IL4R Daudi cells. IL4(5 $\mu$g) was iodinated with 1 mCi Na [$^{125}$I] by the Enzymobead method (Bio-Rad, Melville, N.Y., U.S.A.). Daudi cells ($1\times10^6$) were incubated in 0.2 ml alquots with 0.1 nM ($2\times10^4$ CPM) [$^{125}$I]-IL4 and various concentrations

TABLE 2

Effect of the amino terminus of IL4-toxin on growth of transformed *E. coli*

| Plasmid | IL4-toxin name | N-terminus after initiator Met | | *E. coli* growth $OD_{650}$/plate |
|---|---|---|---|---|
| pRKL4QRD | IL4-PE38Q | HKCDITLQ | (SEQ ID NO:66) | 44 |
| pRKL459K | IL4-PE38KDEL | HKCDITLQ | (SEQ ID NO:66) | 41 |
| pRKL438QRD | IL4(38-37)-PE38Q | NTTEKETF | (SEQ ID NO:67) | 0.95 |
| pRKL4H1K | IL4(HK)(38-37)-PE38KDEL | HKNTTEKETF | (SEQ ID NO:68) | 0.17 |
| pRKL4D1K | IL4(38-37)-PE38KDEL | DTTEKETF | (SEQ ID NO:68) | 16 |

Competent BL21($\lambda$DE3) (50 $\mu$l) was incubated with 2 $\mu$g of plasmid at 4° C. for 30 minutes and 42° C. for 1 minute, shaken with SOC media at 37° C. for 30 minutes and plated on 2 plates of LB-agar containing ampicillin 100 $\mu$g/ml. After incubating 14 hours at 37° C., the bacterial cells were resuspended and the $OD_{650}$ determined.

Example 9

Binding Activity and Cytotoxicity of IL4(38-37)-PE38KDEL

A) Cells and cell culture

The human epidermoid carcinoma cell line A431 contains ~500 IL4 receptors per cell (IL-4R/cell). Antitumor experiments were performed using a derivative of A431, termed ATAC-4, which also displays IL2R$\alpha$ subunits (Kreitman, et al., *Blood,* 83: 426–434 (1994)). This derivative of A431 was used because it was cloned from a single cell, and was more homogenous with respect to IL4R expression than the parent A431 line.

The suspension cell lines Daudi, BL-41 and JD-38 were incubated with toxins in 96-well plates at $4\times10^5$ cells/ml. The remaining adherent cell lines were plated at $1–1.5\times10^4$/well 24 hours prior to the addition of toxin. The media was RPMI containing 10% fetal bovine serum (FBS) for the Burkitt's lymphoma, breast cancer and colon cancer cell lines, and DMEM containing 5% PBS for the epidermoid and renal cell lines. After incubating the ceus with toxins for 24 hours at 37° C., the cells were pulsed with ($^3$H)-leucine (1 $\mu$Ci/well) for 4–6 hours, harvested onto glass fiber filters and counted in a Betaplate (Pharmacia-LKB, Piscataway, N.J., U.S.A.) scintillation counter. PHA cells were prepared by incubating normal peripheral blood mononuclear cells of toxins in media consisting of RPMI containing 10% FBS. After incubating at 4° C. for 1–2 hours, the cells were centrifuged over n-butyl phthalate and counted in a $\gamma$-counter. Assays were performed in triplicate.

The $EC_{50}$, the protein concentration necessary for 50% displacement of [$^{125}$I]-IL4, was 1.25 nM for IL4(38-37)-PE38KDEL and 10 nM for IL4-PE38KDEL. The binding affinity of IL4(38-37)-PE38Q was similar to that of IL4(38-37)-PE38KDEL and the binding affinity of IL4-PE38Q was similar to that of IL4-PE38KDEL. Thus even though the amino terminus was MDTTE (SEQ ID NO:64) instead of MNTTE (SEQ ID NO:63), the binding was still 8–10-fold improved compared to native IL4-toxin.

TABLE 3

Effect of circular permutation of IL4-toxin on cytotoxicity

| | | $IC_{50}$ (ng/ml) | |
|---|---|---|---|
| Cell Line | Cell Type | IL4(38-37)-PE38KDEL | IL4-PE38KDEL |
| MCF-7 | Breast Cancer | 0.6 | 2.6 |
| ZR-75-1 | Breast Cancer | 6 | 13 |
| Daudi | Burkitt's Lymphoma | 0.4 | 2.2 |
| BL-41 | Burkitt's Lymphoma | 25 | 125 |
| JD-38 | Burkitt's Lymphoma | 20 | 65 |
| HT-29 | Colon Cancer | 0.4 | 1.8 |
| LS174T | Colon Cancer | 9 | 30 |
| Colo-201 | Colon Cancer | 0.45 | 2.3 |
| Colo-205 | Colon Cancer | 0.8 | 4 |
| SW1116 | Colon Cancer | 8.5 | 35 |
| SW403 | Colon Cancer | 6.5 | 35 |

TABLE 3-continued Effect of circular permutation of IL4-toxin on cytotoxicity

| | | $IC_{50}$ (ng/ml) | |
|---|---|---|---|
| Cell Line | Cell Type | IL4(38-37)-PE38KDEL | IL4-PE38KDEL |
| A431 | Epidermoid | 0.1 | 0.45 |
| CAKI-I | Renal cell | 40 | 95 |
| RC2 | Renal cell | 1.7 | 7 |
| RC21 | Renal cell | 0.7 | 2.7 |
| RC43 | Renal cell | 35 | 75 |
| UOK101 | Renal cell | 15 | 40 |
| PHA | T-cells, Activated | 0.3 | 1.4 |

C) Cytotoxic activity of IL4(38-37)-PE38KDEL

To determine the cytotoxic activity of IL4(38-37)-PE38KDEL, the CP-ILA-toxin and the native IL4-toxin IL4-PE38KDEL were incubates with a variety of different types of tumor cells and protein synthesis was measured by determining [$^3$H]-leucine uptake. Table 3 shows the $IC_{50}$'s (the toxin concentrations necessary for 50% inhibition of protein synthesis). IL4(38-37)PE38KDEL was several-fold more cytotoxic than IL4-PE38KDEL toward all cell lines. The cytotoxic advantage of IL4(38-37)-PE38KDEL ranged from just about 2-fold on CAKI-I, ZR-75-1, RC43 and UOK101 cells to >5-fold for Daudi, Colo-201 and SW403 cells.

D) Specificity of the cytotoxic activity.

To determine whether the cytotoxicity of IL4(38-37)-PE38KDFL toward A431 cells was specific in requiring IL4R binding, internalization and ADP-ribosylation activity, several control experiments were performed. IL2-PE38KDEL contains the same truncated toxin as IL4(38-37)-PE38KDEL but contains a different binding domain; IL2. IL2-PE38KDEL had no cytotoxicity at 10 ng/ml on A431 cells, indicating that the cytotoxicity of IL4(38-37)-PE38KDEL is not due to nonspecific internalization but requires specific binding. Another control molecule IL4(38-37)-PE38KDEL$^{Asp553}$ contains the E553D mutation which abolishes ADP-ribosylation activity (Carroll et al., *J. Biol. Chem.*, 262: 8707–8711 (1987)). IL4(38-37)-PE38KDEL$^{Asp533}$ was also not cytotoxic toward A431 cells, indicating that the cytotoxicity of IL4(38-37)-PE38KDEL requires toxin internalization, translocation to the cytosol and ADP-ribosylation of EF-2. Binding to the IL4R is also required, since an excess of IL4 can prevent the cytotoxicity of IL4(38-37)-PE38KDEL toward A431 cells.

Competition of the cytotoxicity of IL4(38-37)-PE38KDEL by an excess of IL4 was also, performed for MCF-7, Daudi, HT-29, LS174T, Colo-201, Colo-205, SW1116, SW403 and PHA cells and in all cases the cytotoxicity was reversed indicating IL4R-binding was required for cytotoxicity.

Example 10
Toxicity of IL4-Toxins in Mice

It is possible that the new junction between IL4 and PE in IL4(38-37)-PE38KDEL would allow the toxin to bind and internalize nonspecifically into normal tissues, particularly the liver, and hence nullify any potential therapeutic advantage of the CP-IL4-toxin over the native IL4-toxin. To examine this possibility, several different doses of either IL4(38-37)-PE38KDEL or IL4-PE38KDEL were injected i.v. into nude mice. Table 4 shows that IL4(38-37)-PE38KDEL and IL4-PE38KDEL were similar with respect to toxicity to mice. The calculated $LD_{50}$ for IL4(38-37)-PE38KDEL was 475 μg/Kg×3, compared to 525 μg/Kg×3 for IL4-PE38KDEL. This difference is not significant. Thus the toxicity of IL4 toxin is not significantly enhanced by circular permutation of the ligand.

To determine the organ in mice which determines the maximum tolerated dose, mice receiving IL4(38-37)-PE38KDEL were either sacrificed 2–3 days after the last dose, or blood was withdrawn from the orbital sinus and serum chemistries determined. In the highest doses administered, serum glutamine oxalate and glutamine pyruvate transaminases were elevated and H/E stains of liver indicated hemorrhagic necrosis. Thus the dose limiting toxicity of IL4(38-37)-PE38KDEL in mice is due to liver toxicity, similar to what has been seen with anti-Tac(Fv)-PE38KDEL (Kreitman et al. *Blood*, 83: 426–434 (1994)). This toxic effect is most likely due to nonspecific uptake of the toxin by the liver, since murine IL4R does not bind human IL4 (Morrison et al. *J. Biol. Chem.*, 267: 11957–11963 (1992)).

Example 11
Pharmacokinetics of IL4-Toxins in Mice

For the improved binding of the CP-IL4-toxin to give an improved therapeutic effect, the stability of the CP-IL4-toxin should be similar to that of native IL4-toxin. To determine if this is the case, 10 μg of IL4(38-37)-PE38KDEL or IL4-PE38KDEL was injected i.v., via the tail vein, into nude female mice weighing 16–22 g. At 2, 5, 10, 20, 30, 40, 60, 90, 120, 240 and 360 minutes following injection, blood (50–100 μl) was drawn from the orbital sinus. All mice were drawn at 2 minutes and 3–4 times thereafter. At least 3 mice were drawn for each time point. The serum was stored at −80° C. prior to determination of toxin levels.

Serum levels of recombinant toxins were determined by their cytotoxic activity toward Daudi cells, using a standard curve curve made from the respective purified toxin. The plasma disappearance of IL4(38-37)-PE38KDEL was nearly identical to that of IL4-PE38KDEL. The calculated $T_{1/2}\beta$ was 10 minutes in the case of both IL4(38-37)-PE38KDEL and IL4-PE38KDEL. Thus circular permutation of IL4 does not impair the stability of the toxin fusion in vivo.

Example 12
Antitumor Activity Against Human Il4R-Bearing Carcinoma in Mice

To determine if the improved binding and cytotoxicity of CP-IL4-toxin would lead to improved antitumor activity in vivo, nude mice were injected with A431 cells subcutaneously and treatment began four days later when tumors reached a size of 26–60 mm$^3$. Mice were treated i.v. with IL4(38-37)-PE38KDEL or IL4-PE38KDEL every other day for 3 doses. In all tumor experiments, tumor cells were injected on day 0 and mice were treated on days 4, 6 and 8. FIG. 6 shows the calculated tumor volumes during and after treatment. The data in FIG. 6 constitute averages of up to 5 different independent experiments. In all treatment groups, tumors decreased in size significantly by day 6, just 2 days after initiation of therapy, and usually reached a maximum response by day 8. For both IL4(38-37)-PE38KDEL (FIG. 6A, B and C) and IL4-PE38KDEL (FIG. 6D, E and F), a dose-response effect was observed. By the Mann-Whitney rank order test, day-15 tumor sizes were smaller with 100 μg/Kg×3 compared to 50 μg/Kg×3 of IL4(38-37)-PE38KDEL (p<0.006), and with 200 μg/Kg×3 compared to 50 μg/Kg×3 of IL4-PE38KDEL (p<0.024). At each of the three dose levels, 50, 100 and 200 μg/Kg×3, day-13 or day-15 tumor sizes were smaller after IL4(38-37)-

PE38KDEL than after IL4-PE38KDEL (p<0.002, 0.0001 and 0.095, for the 50, 100 and 200 µg/Kg dose levels, respectively). Moreover, day 13 or day-15 tumor sizes were also smaller after 50 µg/Kg×3 of IL4(38-37)-PE38KDEL than after 100 µg/Kg×3 of IL4-PE38KDEL (p<0.005) and were smaller after 100 µg/Kg×3 of IL4(38-37)PE38KDEL than after 200 µg/Kg×3 of IL4-PE38KDEL (p<0.002). Thus IL4(38-37)-PE38KDEL was more active in vivo than IL4-PE38KDEL, and the difference was at least 2-fold.

Table 5 shows in how many mice tumors completely regressed when treated with either IL4(38-37)-PE38KDEL or IL4-PE38KDEL. A complete response (CR) is defined as complete disappearance of tumor persisting at least until day 15. At doses at or above 100 µg/Kg×3, all mice treated with IL4(38-37)-PE38KDEL obtain a CR. At 50 µg/Kg×3, 80% (24/30) of the mice treated with IL4(38-37)-PE38KDEL obtained a CR, compared to only 3/10 mice treated with IL4-PE38KDEL. In fact, even at a four-fold higher dose, 200 µg/Kg×3, only 70% (7/10) of mice obtained CR's with IL4-PE38KDEL. This indicates that the antitumor effect of the CP-IL4-toxin IL4(38-37)-PE38KDEL is at least four-fold higher than that of the native IL4-toxin IL4-PE38KDEL. However, since some mice in all treatment groups obtilined CR, the error bars around the mean tumor sizes are large (FIG. 6). Nevertheless, chi-square analysis of CR rates in mice (Table IV) indicated that IL4(38-37)-PE38KDEL, 50 µg/Kg×3 was more effective than twice that dose of IL4-PE38KDEL (p<0.025) and that IL4(38-37)-PE38KDEL 100 µg/Kg×3 was more effective than twice that dose of IL4-PE38KDEL (p<0.005).

Antitumor study. Nude female mice 6–8 weeks of age and weighing 16–22 g were injected usually with 0.5–1×10$^6$ A431 cells subcutaneously on day 0 and by day 4 small tumors had developed. Mice were then treated i.v. with recombinant toxins on days 4, 6 and 8. Tumor volumes were calculated based on the formula volume=(length)(width)$^2$ (0.4).

TABLE 5

Antitumor responses with IL4-toxins

| Dose level | CR rate (complete remissions/total mice) | |
|---|---|---|
| (µg/Kg i.v. QOD × 3) | IL4(38-37)-PE38KDEL | IL4-PE38KDEL |
| 25 | 2/10 | |
| 50 | 24/30 | 3/10 |
| 70 | | 4/10 |
| 100 | 30/30 | 4/10 |
| 140 | | 5/10 |
| 200 | 5/5 | 7/10 |

Mice (~20 g) were injected subcutaneously on day 0 and tumors developed by day 4. CR (complete remission) is defined as total disappearance of tumor persisting at least until day 15.

Example 13
Durable Complete Remissions

Figure 7A:
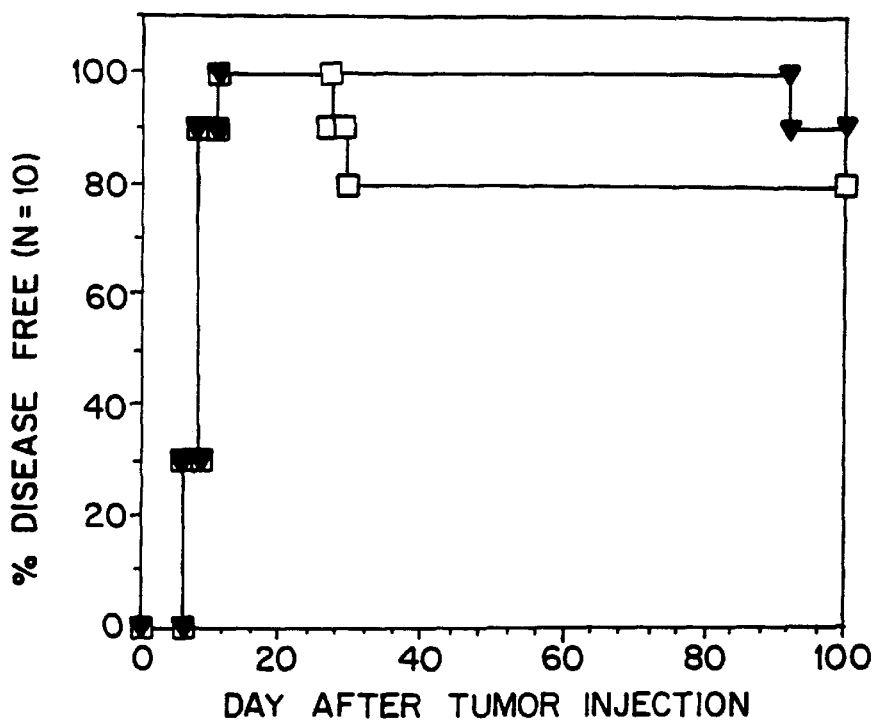
Figure 7B:
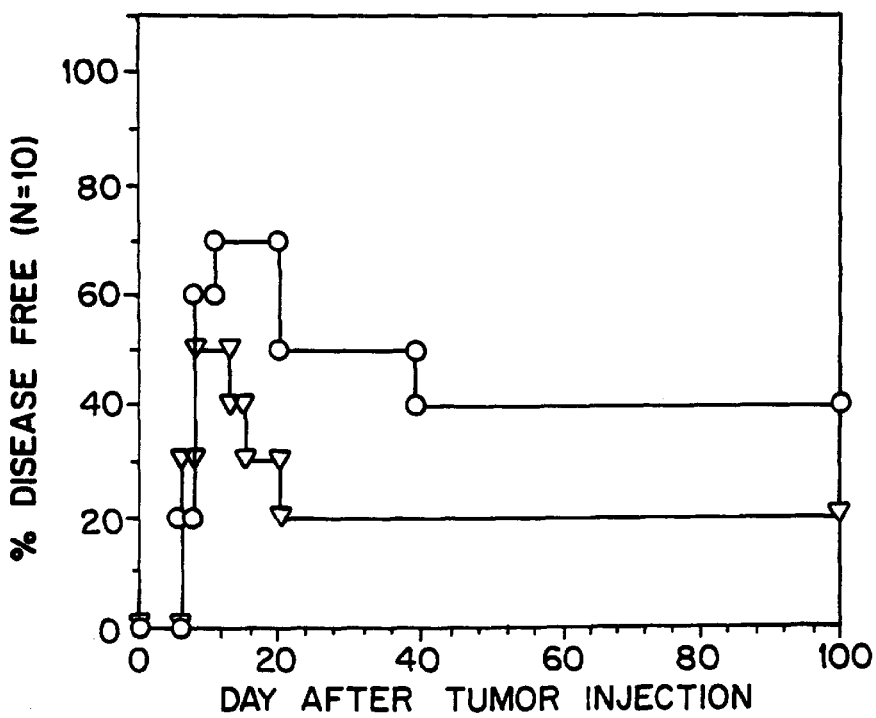

To determine how durable the CR's were to IL4-toxins, two independent experiments were performed where groups of 5 mice (total of 10 mice/group) were treated with IL4-(38-37)-PE38KDEL at 50 or 100 µg/Kg QOD×3, or IL4-PE38KDEL at 100 or 200 µg/Kg QOD×3 and then followed for 100 days. FIG. 7 shows the combined data of the two experiments showing the percent of animals developing CR's and percent of aminals maintaining these CR's. All animal treated with IL4-(38-37)-PE38KDEL obtained CR compared with 50% and 70% of the mice treated with IL4-PE38KDEL at 100 or 200 µg/Kg QOD×3, respectively. Only one of ten animals treated with IL4(38-37)-PE38KDEL 100 µg/Kg×3 relapsed, and this occurred after nearly 3 months. Two of ten animals treated with IL4-(38-37)-PE38KDEL 50 µg/Kg×3 relapsed in the first month and none relapsed thereafter. Animals treated with IL4-PE38KDEL relapsed more frequently, so that at 100 days 40% and 20% of mice treated with 100 µg/Kg×3 and 200 µg/Kg×3, respectively, were still in CR. By the Kaplan-Meier method, the likelihood of remaining in CR, once it was obtained, was higher for mice receiving IL4(38-37)-PE38KDEL 50 µg/Kg i.v. QOD×3 than for mice receiving IL4-PE38KDEL 200 µg/Kg i.v. QOD×3 (p<0.03), indicating a greater than four-fold difference between the two agents. By harvesting tumors from several animals relapsing after IL4-toxin treatment, regrowing the cells in vitro, and testing for IL4-toxin sensitivity, it was possible to determine whether the surviving tumor cells had lost receptor. It was found that tumor cells grown from relapsed IL4-toxin-treated mice were several-fold to >10-fold less sensitive to IL4-toxins compared to tumors harvested from treated mice. Thus, IL4(38-37)-PE38KDEL induced CR's which were more durable than those induced by IL4-PE38KDEL, probably because IL4(38-37)-PE38KDEL was superior in killing cells displaying lower IL4R numbers.

To determine whether the antitumor activity of IL4(38-37)-PE38KDEL required specific binding, internalization and ADP-ribosylation in the tumor cells, the tumor-bearing mice were treated with the control molecules IL2-PE38KDEL and IL4(38-37)-PE38KDEL$^{Asp553}$. Neither of these toxins were cytotoxic against A431 cells in tissue culture at 10 ng/ml. Treatment with IL2-PE38KDEL showed no antitumor activity, indicating that the antitumor activity of IL4(38-37)-PE38KDEL was not due to nonspecific effects of the toxin. Also, IL4(38-37)-PE38KDEL$^{Asp553}$ failed to cause antitumor activity, indicating that the antitumor activity of IL4(38-37)-PE38KDEL was not simply due to the binding of the IL4 portion of the toxin to the tumor cells. Thus the antitumor effect of IL4(38-37)-PE38KDEL required specific binding, internalization and ADP-ribosylation within the cytosol of the target cells.

Example 14
Biological Activity and Structural Inferences
A) Mitogenic activity of CP variants of IL4

It has been shown that mutations in human IL4 which prevent its proliferative activity often have much less effect on binding (Kruse et al. *EMBO J.*, 11: 3237–3244 (1992)). It is therefore theoretically possible that CP-IL4 mutants might bind to the IL4R with full affinity but be unable to initiate the signal transduction which leads to proliferation. Thus, the proliferative activity of circularly permuted IL4s was examined (FIG. 3(B)).

Accordingly, different concentrations of IL4, IL4(38-37) and IL4(105-104) were incubated with about 6×10$^4$ CTLL$^{hIL4R}$ cells (Idzerda et al., *J. Exp. Med.* 861–873 (1990)) in 200 µl of DMEM with 10% FBS for 6 hours and then incubated for 18 hours with [$^3$H]-thymidine (0.5 µCi/well) to measure cellular proliferation rate. The CTLL$^{hIL4R}$ cells are murine cells, which are transfected with a human IL4R cDNA, and proliferate in a specific manner when exposed to human IL4(Id.). To verify that the native IL4 used in these assays had full activity, its binding activity and appearance on SDS-PAGE was compared to that of clinical grade IL4 (5×10$^7$ U/mg).

The concentration required for increasing the [$^3$H]-thymidine incorporation to 30,000 cpm, which is approximately half-maximal, was 0.12 nM for IL4, 0.2 nM for IL4(105-104) and 0.24 nM for IL4(38-37). Thus, the proliferative activity of the CP-IL4 molecules was 50–100% of that of IL4, confirming that their three dimensional structures must be similar to that of IL4.

B) Upregulation of B-cell CD23 by CP variants of IL4

Another effect of IL4 signal transduction is the induction of CD23 on the surface of B-lymphocytes (Defrance et al. *J. Exp. Med.*, 165: 1459–1467 (1987)). To assess whether the CP variants were capable of this activity, RAMOS Burkitt's lymphoma cells were incubated overnight, at 37° C., with 10 ng/ml of either IL4, IL4(38-37) or IL4(105-104). Cells were then stained with anti-CD-23(AMAC, Inc., Westbrook, Mich., U.S.A.) or IgG1 isotype control and analyzed by FACScan (Becton-Dickinson, Sandy, Utah, U.S.A.)., stained with anti-CD23, and analyzed by FACS. All 3 molecules induced CD23 upregulation with a similar increase in mean fluorescence intensity. Thus circularization of IL4 does not impair the ability of the growth factor to upregulate CD23.

C) Circular Dichroism of CP variations of IL4

To directly measure the structural effect on IL4 of circular permutation, IL4(38-37) and IL4(105-104) were analyzed by circular dichroism (CD). CD spectra were measured in a Jasco J-500 spectropolarimeter from 260-195 nm, as described elsewhere (McPhie et al. *Archiv. Biochem. Biophys.,* 293: 46–53 (1992)). Protein solutions (50–100 $\mu$g/ml) in 0.1 M phosphate buffer were held in 1 mm pathlength quartz cuvettes which were thermostated at 25° C. Protein concentrations were measured by absorbance measurements at 280 and 215 nm, in a Cary 119 spectrophotometer, as previously described (Prasad et al. *Biochemistry,* 25: 5214–5219 (1986)). The derived spectra were analyzed in terms of secondary structure using the CONTIN program (Povencher et al., *Biochemistry,* 20: 33–37 (1981)).

The CD spectra of IL4 and the CP variants indicate that the three proteins are similar in conformation. Negative bands at 208 nm and 222 nm and an intense positive band below 195 nm are characteristic of proteins which are rich in $\alpha$-helix. The $[\theta]_{215}$, which is a global measure of protein folding, was 138°$cm^2$/mmol, compared to 158 for IL4(38-37) and 123 for IL4(105-104). To determine if the decreased value for IL4(105-104) was due to a loss of $\alpha$-helix or $\beta$-sheet, The CONTIN program was used, which supplies a series of acceptable fits to the measured spectra in terms of 15 standard spectra of protein of known crystal structures (Povencher et al. *Biochemistry,* 20: 33–37 (1981)). The values for intact IL4 and IL4(38-37) are in good agreement with reported assignments for IL4, namely 54% $\alpha$-helix and 4.5% $\beta$-sheet (Garrett et al. *Biochemistry,* 31: 4347–4353 (1992)). The fitted secondary structure for IL4(105-104), however, did indicate some loss of $\alpha$-helix and a slight excess of $\beta$-sheet.

The CD studies suggested that while IL4(38-37) is not significantly different structurally from IL4, the IL4(105-104) molecule exhibits a slight loss of $\alpha$-helix and a slight excess of $\beta$-sheet. It is possible that the new C-terminus for this protein, Asp104, lies adjacent to the short $\beta$-strand (residues 106–107) which anchors the last (D) helix according to the known NMR structure and that the increased charge density at this site may disturb the $\alpha$-helix somewhat. Nevertheless, the binding and signal transduction properties of this mutant are well preserved.

The above data indicate that while residues near the IL4 C-terminus may be important for binding and mitogenic activity (Le et al. *Biochemistry,* 30: 9576–9582 (1991), Morrison et al., *J. Biol. Chem.,* 267: 11957–11963)), a free N- or C-terminus is not needed for either action. It is likely that the residues important for receptor binding and signal transduction interact with the receptor independently of either termini, and that their interaction is not impaired by the loop formed after fusion of the native N- and C-termini. Binding, T-cell proliferation, and NMR studies on IL4 mutants have recently suggested that residues near the N-terminus and on helix C bind to the IL4R, while residues near the C-terminus bind to a second receptor responsible for signal transduction (Kruse et al., (1993), supra., Muller et al. *J. Mmol. Biol.,* 237: 423–436(1994)). This second receptor is likely to be the common $\gamma$-receptor, which has been found to be important for signal transduction of the IL4R (Russel et al. *Science,* 262: 1880–1883 (1993), Kondo et al. *Science,* 262: 1874–1877 (1993)). The influence of this subunit for IL4 binding, however, is only 2.5 to 3-fold (Russel et al., supra). This model, together with the present finding that a circularized C and N terminus of IL4 does not impair binding or signal transduction, may explain why fusion of IL4 to toxins through its C-terminus is detrimental to IL4R-binding. If the C-terminal residues and the C-terminus itself lack importance to IL4R-binding, it is likely that fusion of the C-terminus to another protein disturbs the nearby N-terminal residues which are a part of "site 1" and are critical for IL4R binding. The present data suggest that IL4(38-37) is useful for fusion to other proteins if other aspects of IL4 need to be preserved, such as signal transduction.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference.

What is claimed is:

1. A circularly permuted ligand selected from the group consisting of interleukin 4 (IL-4), interleukin 2 (IL-2), granulocyte colony stimulating factor (G-CSF), and granulocyte/macrophage colony stimulating factor (GM-CSF) that is a modification of an original ligand having amino acid residues numbered sequentially 1 through J with an amino terminus at residue 1 and a carboxyl terminus at residue J, said modified ligand having the formula shown below:

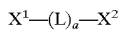

in which:

a is 0 or 1:

$X^1$ is a peptide consisting of an amino acid sequence having the sequence of residues n+1 through J of said original ligand;

$X^2$ is a peptide consisting of an amino acid sequence having the sequence of residues 1 through n of said original ligand;

n is an integer ranging from 1 to J−1; and

L is a linker; and further wherein the amino acid terminus of the modified ligand is located in $X^1$ and the carboxyl terminus of the modified ligand is located in $X^2$.

2. The circularly permuted ligand of claim 1, in which a is 1 and L is a peptide.

3. The circularly permuted ligand of claim 2, in which L is GGNGG (SEQ ID NO:50).

4. The circularly permuted ligand of claim 1, wherein said original ligand is interleukin 4 (IL-4).

5. The circularly permuted ligand of claim 4, wherein the first asparagine in the amino terminus of said original ligand is changed to an aspartate.

6. The circularly permuted ligand of claim 1, wherein said original ligand is interleukin 2 (IL-2).

7. The circularly permuted ligand of claim 1, wherein said original ligand is G-CSF.

8. The circularly permuted ligand of claim 1, wherein said original ligand is GM-CSF.

9. The circularly permuted ligand of claim 1, in which:

X¹ comprises the amino acid sequence having methionine followed by residues 38 through 129 of SEQ ID NO:2 (interleukin 4); and X² comprises the amino acid sequence having residues 1 through 37 of SEQ ID NO:2 (interleukin 4).

10. The circularly permuted ligand of claim 9, in which a is 1 and L is the peptide GGNGG (SEQ ID NO:50).

11. The circularly permuted ligand of claim 1, in which:

X¹ comprises the amino acid sequence having methionine followed by residues 105 through 129 of SEQ ID NO:2 (interleukin 4); and X² comprises the amino acid sequence having residues 1 through 104 of SEQ ID NO:2 (interleukin 4).

12. The circularly permuted ligand of claim 11, in which a is 1 and L is the peptide GGNGG (SEQ ID NO:50).

13. The circularly permuted ligand of claim 1, in which:

X¹ comprises the amino acid sequence having residues 39 through 134 of SEQ ID NO:3 (interleukin 2); and X² comprises the amino acid sequence having residues 1 through 38 of SEQ ID NO:3 (interleukin 2).

14. The circularly permuted ligand of claim 13, in which a is 1 and L is the peptide GGNGG (SEQ ID NO. 50).

15. The circularly permuted ligand of claim 1, in which:

X¹ comprises the amino acid sequence having residues 69 through 175 of SEQ ID NO:5 (G-CSF); and X² comprises the amino acid sequence having residues 1 through 68 of SEQ ID NO:5 (G-CSF).

16. The circularly permuted ligand of claim 15 in which a is 1 and L is the peptide GGGNGGG (SEQ ID NO.52).

17. The circularly permuted ligand of claim 1, in which:

X¹ comprises the amino acid sequence having residues 36 through 128 of SEQ ID NO:4 (GM-CSF); and X² comprises the amino acid sequence having residues 1 through 36 of SEQ ID NO:4 (GM-CSF).

18. The circularly permuted ligand of claim 17 in which a is 1 and L is the peptide GGGNGGG (SEQ ID NO. 52).

19. A chimeric molecule comprising a circularly permuted interleukin ligand component that is a modification of an original interleukin ligand having amino acid residues numbered sequentially 1 through J with an amino terminus at residue 1 and a carboxyl terminus at residue J, said chimeric molecule having the following formula:

$$(T^1)_a—(S^1)_b—X^1—(L)_c—X^2—(S^2)_d—(T^2)_e$$

in which:

X¹ is a peptide consisting of an amino acid sequence having the sequence of residues n+1 through J of said original interleukin ligand;

L is a linker;

X² is a peptide consisting of an amino acid sequence having the sequence of residues 1 through n of said original interleukin ligand;

S¹ and S² are peptide spacers;

n is an integer ranging from 1 to J–1;

b, c and d are each independently 0 or 1;

a and e are either 0 or 1, provided that a and e cannot both be 0; and

T¹ and T² are proteins.

20. The chimeric molecule of claim 19, wherein said chimeric molecule is a fusion protein.

21. The chimeric molecule of claim 20, in which a is zero;

b is zero;

c is 1;

d is 1;

e is 1; and

T² is a Pseudomonas exotoxin (PE) in which domain Ia is lacking.

22. The chimeric molecule of claim 21, in which:

X¹ comprises methionine followed by the amino acid sequence having residues 38 through 129 of SEQ ID NO:2 (interleukin 4);

L is GGNGG (SEQ ID NO:50);

X² comprises the amino acid sequence having residues 1 through 37 of SEQ ID NO:2 (interleukin 4);

S² is ASGGPE (SEQ ID NO:57); and

T² is selected from the group consisting of PE38Q and PE38KDEL.

23. The chimeric molecule of claim 21, in which:

X¹ comprises the amino acid methionine followed by the amino acid sequence having residues 105 through 129 of SEQ ID NO:2 (interleukin 4);

L is GGNGG (SEQ ID NO:50);

X² comprises the amino acid sequence having residues 1 through 104 of SEQ ID NO:2 (interleukin 4);

S² is SGGPE (SEQ ID NO:51); and

T² is selected from the group consisting of PE38Q and PE38KDEL.

24. The chimeric molecule of claim 21, in which:

X¹ comprises amino acid methionine followed by the amino acid sequence having residues 39 through 134 of SEQ ID NO:3 (interleukin 2);

L is GGNGG (SEQ ID NO:50);

X² comprises the amino acid sequence having residues 1 through 38 of SEQ ID NO:3 (interleukin 2);

S² is SGGPE (SEQ ID NO:51); and

T² is selected from the group consisting of PE38Q and PE38KDEL.

25. The chimeric molecule of claim 20, in which:

a is 1;

b is 1;

c is 1;

d is zero;

e is zero; and

T¹ is a truncated Diphtheria toxin (DT).

26. The chimeric molecule of claim 25 in which:

X¹ comprises the amino acid methionine followed by the amino acid sequence having residues 38 through 129 of SEQ ID NO:2 (interleukin 4);

L is GGNGG (SEQ ID NO:50);

X² comprises the amino acid sequence having residues 1 through 37 of SEQ ID NO:2 (interleukin 4);

S¹ is HM; and

T¹ is DT388.

27. The chimeric molecule of claim 25, in which:

X¹ comprises the amino acid methionine followed by the amino acid sequence having residues 105 through 129 of SEQ ID NO:2 (interleukin 4);

L is GGNGG (SEQ ID NO:50);

X² comprises the amino acid sequence having residues 1 through 104 of SEQ ID NO:2 (interleukin 4);

S¹ is RPHMAD (SEQ ID NO:53); and

T¹ is DT388.

28. The chimeric molecule of claim 20, in which:
a is 1;
b is 1;
d is 0;
e is 0; and
T¹ is an antibody.

29. The chimeric molecule of claim 28, in which:
X¹ comprises the amino acid methionine followed by the amino acid sequence corresponding to residues 38 through 129 of SEQ ID NO:3 (interleukin 4);
L is GGNGG (SEQ ID NO:50);
X² comprises the amino acid sequence having residues 1 through 37 of SEQ ID NO:2 (interleukin 4);
S¹ is ASGGPE (SEQ ID NO:57); and
T¹ is B3(Fv).

30. The chimeric molecule of claim 28, in which:
X¹ comprises the amino acid methionine followed by the amino acid sequence having residues 105 through 129 of SEQ ID NO:3 (interleukin 4);
L is GGNGG (SEQ ID NO:50);
X² comprises the amino acid sequence having residues 1 through 104 of SEQ ID NO:2 (interleukin 4);
S¹ is SGGPE (SEQ ID NO:51); and
T¹ is B3(Fv).

31. A method of inhibiting growth of tumor cells in an organism, said method comprising contacting said cells with a composition comprising a fusion protein said fusion protein comprising a modified ligand component selected from the group consisting of cytokines and colony stimulating factors that is a modification of an original ligand selected from the group consisting of cytokines and colony stimulating factors that specifically binds a tumor cell, said original ligand having amino acid residues numbered sequentially 1 through J with an amino terminus at residue 1 and a carboxyl terminus at residue J, the fusion protein having the following formula:

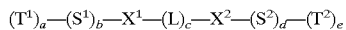

$(T^1)_a-(S^1)_b-X^1-(L)_c-X^2-(S^2)_d-(T^2)_e$ in which:
X¹ is a peptide consisting of an amino acid sequence having the sequence of residues n+1 through J of said original ligand;
L is a linker
X² is a peptide consisting of an amino acid sequence having the sequence of residues 1 through n of said original ligand;
S¹ and S² are peptide spacers;
n is an integer ranging from 1 to J−1; and
b, c, and d are each independently 0 or 1;
a and e are either 0 or 1, provided that a and e cannot both be 0; and
T¹ and T² are cytotoxins.

32. The method of claim 31, wherein said original ligand is interleukin 4 (IL-4).

33. The method of claim 32, in which:
X¹ is methionine followed by the amino acid sequence having residues 38 through 129 of SEQ ID NO:2 (interleukin 4);
L is GGNGG (SEQ ID NO:50);
X² is the amino acid sequence having residues 1 through 37 of SEQ ID NO:2 (interleukin 4);
S² is ASGGPE (SEQ ID NO:57); and
T² is selected from the group consisting of PE38Q and PE38KDEL.

34. The method of claim 32, in which:
X¹ is the amino acid methionine followed by the amino acid sequence having residues 105 through 129 of SEQ ID NO:2 (interleukin 4);
L is GGNGG (SEQ ID NO:50);
X² comprises the amino acid sequence corresponding to residues 1 through 104 of SEQ ID NO:2 (interleukin 4);
S² is SGGPE (SEQ ID NO:51); and
T² is selected from the group consisting of PE38Q and PE38KDEL.

35. The method of claim 31, wherein said original ligand is interleukin 2 (IL-2).

36. The method of claim 31, wherein said original ligand is granulocyte colony stimulating factor (G-CSF).

37. The method of claim 31, wherein said original ligand is granulocyte/macrophage colony stimulating factor (GM-CSF).

38. The method of claim 31, in which
a is zero;
b is zero;
c is 1;
d is 1;
e is 1; and
T² is a Pseudomonas exotoxin in which domain Ia is lacking.

39. The method of claim 31, in which:
a is 1;
b is 1;
c is 1;
d is zero;
e is zero; and
T¹ is a truncated Diphtheria toxin.

40. The method of claim 31 in which:
X¹ is the amino acid methionine followed by the amino acid sequence having residues 38 through 129 of SEQ ID NO:2 (interleukin 4);
L is GGNGG (SEQ ID NO:50);
X² the amino acid sequence having residues 1 through 37 of SEQ ID NO:2-(interleukin 4);
S¹ is HM; and
T¹ is DT388.

41. The method of claim 31, in which:
X¹ is the amino acid methionine followed by the amino acid sequence having residues 105 through 129 of SEQ ID NO:2 (interleukin 4);
L is GGNGG (SEQ ID NO:50);
X² is the amino acid sequence having residues 1 through 104 of SEQ ID NO:2 (interleukin 4);
S¹ is RPHMAD (SEQ ID NO:53); and
T¹ is DT388.

42. A method of specifically delivering a first molecule to a target cell in vivo said method comprising:
administering to a mammal a molecule comprising at circularly permuted ligand selected from the group consisting of cytokines and colony stimulating factors in a pharmaceutically acceptable carrier; wherein said ligand specifically binds said target cell.

43. The method of claim 42, wherein said ligand is selected from the group consisting of interleukin 2 (IL-2, interleukin 4 (IL-4), granulocyte/macrophage colony stimulating factor (GM-CSF), and granulocyte colony stimulating factor (G-CSF).

44. The method of claim 43, wherein said ligand is attached to a cytotoxin.

45. A chimeric molecule comprising a circularly permuted growth factor ligand component that is a modification of an original growth factor ligand having amino acid residues numbered sequentially 1 through J with an amino terminus at residue 1 and a carboxyl terminus at residue J, said

SEQUENCE LISTING (1) GENERAL INFORMATION:

(iii) NUMBER OF SEQUENCES: 72

(2) INFORMATION FOR SEQ ID NO:1:

(i) SEQUENCE CHARACTERISTICS:
(A) LENGTH: 614 amino acids
(B) TYPE: amino acid
(C) STRANDEDNESS:

(D) TOPOLOGY: linear (ii) MOLECULE TYPE: protein (ix) FEATURE:
(A) NAME/KEY: Protein
(B) LOCATION: 1..614
(D) OTHER INFORMATION: /note= "native Pseudomonas exotoxin (PE)"

(xi) SEQUENCE DESCRIPTION: SEQ ID NO:1:

```
Met Ala Glu Glu Ala Phe Asp Leu Trp Asn Glu Cys Ala Lys Ala Cys
1               5                   10                  15

Val Leu Asp Leu Lys Asp Gly Val Arg Ser Ser Arg Met Ser Val Asp
            20                  25                  30

Pro Ala Ile Ala Asp Thr Asn Gly Gln Gly Val Leu His Tyr Ser Met
        35                  40                  45

Val Leu Glu Gly Gly Asn Asp Ala Leu Lys Leu Ala Ile Asp Asn Ala
    50                  55                  60

Leu Ser Ile Thr Ser Asp Gly Leu Thr Ile Arg Leu Glu Gly Gly Val
65                  70                  75                  80

Glu Pro Asn Lys Pro Val Arg Tyr Ser Tyr Thr Arg Gln Ala Arg Gly
                85                  90                  95

Ser Trp Ser Leu Asn Trp Leu Val Pro Ile Gly His Glu Lys Pro Ser
            100                 105                 110

Asn Ile Lys Val Phe Ile His Glu Leu Asn Ala Gly Asn Gln Leu Ser
        115                 120                 125

His Met Ser Pro Ile Tyr Thr Ile Glu Met Gly Asp Glu Leu Leu Ala
    130                 135                 140

Lys Leu Ala Arg Asp Ala Thr Phe Phe Val Arg Ala His Glu Ser Asn
145                 150                 155                 160

Glu Met Gln Pro Thr Leu Ala Ile Ser His Ala Gly Val Ser Val Val
                165                 170                 175

Met Ala Gln Thr Gln Pro Arg Arg Glu Lys Arg Trp Ser Glu Trp Ala
            180                 185                 190

Ser Gly Lys Val Leu Cys Leu Leu Asp Pro Leu Asp Gly Val Tyr Asn
        195                 200                 205

Tyr Leu Ala Gln Gln Arg Cys Asn Leu Asp Asp Thr Trp Glu Gly Lys
    210                 215                 220

Ile Tyr Arg Val Leu Ala Gly Asn Pro Ala Lys His Asp Leu Asp Ile
225                 230                 235                 240

Lys Pro Thr Val Ile Ser His Arg Leu His Phe Pro Glu Gly Gly Ser
                245                 250                 255

Leu Ala Ala Leu Thr Ala His Gln Ala Cys His Leu Pro Leu Glu Thr
            260                 265                 270

Phe Thr Arg His Arg Gln Pro Arg Gly Trp Glu Gln Leu Glu Gln Cys
        275                 280                 285

Gly Tyr Pro Val Gln Arg Leu Val Ala Leu Tyr Leu Ala Ala Arg Leu
    290                 295                 300

Ser Trp Asn Gln Val Asp Gln Val Ile Arg Asn Ala Leu Ala Ser Pro
305                 310                 315                 320

Gly Ser Gly Gly Asp Leu Gly Glu Ala Ile Arg Glu Gln Pro Glu Gln
                325                 330                 335

Ala Arg Leu Ala Leu Thr Leu Ala Ala Ala Glu Ser Glu Arg Phe Val
            340                 345                 350

Arg Gln Gly Thr Gly Asn Asp Glu Ala Gly Ala Ala Asn Ala Asp Val
        355                 360                 365
```

```
Val Ser Leu Thr Cys Pro Val Ala Ala Gly Glu Cys Ala Gly Pro Ala
    370                 375                 380

Asp Ser Gly Asp Ala Leu Leu Glu Arg Asn Tyr Pro Thr Gly Ala Glu
385                 390                 395                 400

Phe Leu Gly Asp Gly Gly Asp Val Ser Phe Ser Thr Arg Gly Thr Gln
                    405                 410                 415

Asn Trp Thr Val Glu Arg Leu Leu Gln Ala His Arg Gln Leu Glu Glu
                420                 425                 430

Arg Gly Tyr Val Phe Val Gly Tyr His Gly Thr Phe Leu Glu Ala Ala
            435                 440                 445

Gln Ser Ile Val Phe Gly Gly Val Arg Ala Arg Ser Gln Asp Leu Asp
        450                 455                 460

Ala Ile Trp Arg Gly Phe Tyr Ile Ala Gly Asp Pro Ala Leu Ala Tyr
465                 470                 475                 480

Gly Tyr Ala Gln Asp Gln Glu Pro Asp Ala Arg Gly Arg Ile Arg Asn
                    485                 490                 495

Gly Ala Leu Leu Arg Val Tyr Val Pro Arg Ser Ser Leu Pro Gly Phe
                500                 505                 510

Tyr Arg Thr Ser Leu Thr Leu Ala Ala Pro Glu Ala Ala Gly Glu Val
            515                 520                 525

Glu Arg Leu Ile Gly His Pro Leu Pro Leu Arg Leu Asp Ala Ile Thr
        530                 535                 540

Gly Pro Glu Glu Glu Gly Gly Arg Leu Glu Thr Ile Leu Gly Trp Pro
545                 550                 555                 560

Leu Ala Glu Arg Thr Val Val Ile Pro Ser Ala Ile Pro Thr Asp Pro
                    565                 570                 575

Arg Asn Val Gly Gly Asp Leu Asp Pro Ser Ser Ile Pro Asp Lys Glu
                580                 585                 590

Gln Ala Ile Ser Ala Leu Pro Asp Tyr Ala Ser Gln Pro Gly Lys Pro
            595                 600                 605

Pro Arg Glu Asp Leu Lys
    610

(2) INFORMATION FOR SEQ ID NO:2:

(i) SEQUENCE CHARACTERISTICS:
        (A) LENGTH: 129 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..129
        (D) OTHER INFORMATION: /note= "interleukin 4 (IL4)"

(xi) SEQUENCE DESCRIPTION: SEQ ID NO:2:

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
```

```
                        65                  70                  75                  80
Arg Phe Leu Lys Arg Leu Asp Arg Asn Leu Trp Gly Leu Ala Gly Leu
                85                  90                  95
Asn Ser Cys Pro Val Lys Glu Ala Asn Gln Ser Thr Leu Glu Asn Phe
                100                 105                 110
Leu Glu Arg Leu Lys Thr Ile Met Arg Glu Lys Tyr Ser Lys Cys Ser
            115                 120                 125
Ser
```

(2) INFORMATION FOR SEQ ID NO:3:

(i) SEQUENCE CHARACTERISTICS:
        (A) LENGTH: 133 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..133
        (D) OTHER INFORMATION: /note= "interleukin 2 (IL2)"

(xi) SEQUENCE DESCRIPTION: SEQ ID NO:3:

```
Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Phe Lys Phe Tyr Met Pro Lys
            35                  40                  45
Lys Ala Thr Glu Leu Lys His Leu Gln Cys Leu Glu Glu Glu Leu Lys
        50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Cys Gln Ser Ile
            115                 120                 125
Ile Ser Thr Leu Thr
        130
```

(2) INFORMATION FOR SEQ ID NO:4:

(i) SEQUENCE CHARACTERISTICS:
        (A) LENGTH: 127 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..127
        (D) OTHER INFORMATION: /note= "granulocyte-macrophage
            colony-stimulating factor (GM-CSF)"

(xi) SEQUENCE DESCRIPTION: SEQ ID NO:4:

```
Ala Pro Ala Arg Ser Pro Ser Pro Ser Thr Gln Pro Trp Glu His Val
1               5                   10                  15
```

```
Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
50                      55                  60

Gly Leu Arg Gly Ser Leu Thr Lys Leu Lys Gly Pro Leu Thr Met Met
65                      70                  75                  80

Ala Ser His Tyr Lys Gln His Cys Pro Pro Thr Pro Glu Thr Ser Cys
                    85                  90                  95

Ala Thr Gln Thr Ile Thr Phe Glu Ser Phe Lys Glu Asn Leu Lys Asp
                100                 105                 110

Phe Leu Leu Val Ile Pro Phe Asp Cys Trp Glu Pro Val Gln Glu
                115                 120                 125
```

(2) INFORMATION FOR SEQ ID NO:5:

(i) SEQUENCE CHARACTERISTICS:
        (A) LENGTH: 174 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..174
        (D) OTHER INFORMATION: /note= "granulocyte
            colony-stimulating factor (G-CSF)"

(xi) SEQUENCE DESCRIPTION: SEQ ID NO:5:

```
Thr Pro Leu Gly Pro Ala Ser Ser Leu Pro Gln Ser Phe Leu Leu Lys
1                   5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
                100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
        130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single (D) TOPOLOGY: linear (ii) MOLECULE TYPE: DNA (ix) FEATURE:
          (A) NAME/KEY: -
          (B) LOCATION: 1..17
          (D) OTHER INFORMATION: /note= "BK24 primer"

(xi) SEQUENCE DESCRIPTION: SEQ ID NO:6:

AATACGACTC ACTATAG                                                           17

(2) INFORMATION FOR SEQ ID NO:7:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: -
          (B) LOCATION: 1..24
          (D) OTHER INFORMATION: /note= "BK50 primer"

(xi) SEQUENCE DESCRIPTION: SEQ ID NO:7:

GGCACCGTTG CGAATCCGGC CGCG                                                   24

(2) INFORMATION FOR SEQ ID NO:8:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: -
          (B) LOCATION: 1..27
          (D) OTHER INFORMATION: /note= "BK54 primer"

(xi) SEQUENCE DESCRIPTION: SEQ ID NO:8:

TGCTTTACGG GCTACGCCCA GGACCAG                                                27

(2) INFORMATION FOR SEQ ID NO:9:

(i) SEQUENCE CHARACTERISTICS:
          (A) LENGTH: 57 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: -
          (B) LOCATION: 1..57
          (D) OTHER INFORMATION: /note= "BK55 primer"

(xi) SEQUENCE DESCRIPTION: SEQ ID NO:9:

GGGACCTCCG GACGATTTGC CTGAGGAGAC GGTGACCTCG GTACCTTGGC CCCAGTA               57

(2) INFORMATION FOR SEQ ID NO:10:

(i) SEQUENCE CHARACTERISTICS:
          (A) LENGTH: 36 base pairs
          (B) TYPE: nucleic acid
          (C) STRANDEDNESS: single (D) TOPOLOGY: linear (ii) MOLECULE TYPE: DNA (ix) FEATURE:
                    (A) NAME/KEY: -
                    (B) LOCATION: 1..36
                    (D) OTHER INFORMATION: /note= "BK56 primer"

(xi) SEQUENCE DESCRIPTION: SEQ ID NO:10:

GGGACCTCCA GCTTTACTCT CGAGCTTTGT CCCCGA                              36

(2) INFORMATION FOR SEQ ID NO:11:

(i) SEQUENCE CHARACTERISTICS:
                    (A) LENGTH: 21 base pairs
                    (B) TYPE: nucleic acid
                    (C) STRANDEDNESS: single
                    (D) TOPOLOGY: linear (ii) MOLECULE TYPE: DNA (ix) FEATURE:
                    (A) NAME/KEY: -
                    (B) LOCATION: 1..21
                    (D) OTHER INFORMATION: /note= "BK63 primer"

(xi) SEQUENCE DESCRIPTION: SEQ ID NO:11:

CACCGTCCAG TTCTGCGTGC C                                              21

(2) INFORMATION FOR SEQ ID NO:12:

(i) SEQUENCE CHARACTERISTICS:
                    (A) LENGTH: 21 base pairs
                    (B) TYPE: nucleic acid
                    (C) STRANDEDNESS: single
                    (D) TOPOLOGY: linear (ii) MOLECULE TYPE: DNA (ix) FEATURE:
                    (A) NAME/KEY: -
                    (B) LOCATION: 1..21
                    (D) OTHER INFORMATION: /note= "BK78 primer"

(xi) SEQUENCE DESCRIPTION: SEQ ID NO:12:

ATACGACTCA CTATAGGGAG A                                              21

(2) INFORMATION FOR SEQ ID NO:13:

(i) SEQUENCE CHARACTERISTICS:
                    (A) LENGTH: 51 base pairs
                    (B) TYPE: nucleic acid
                    (C) STRANDEDNESS: single
                    (D) TOPOLOGY: linear (ii) MOLECULE TYPE: DNA (ix) FEATURE:
                    (A) NAME/KEY: -
                    (B) LOCATION: 1..51
                    (D) OTHER INFORMATION: /note= "BK83 primer"

(xi) SEQUENCE DESCRIPTION: SEQ ID NO:13:

GGGCATAAAC CCGGGCATAA AACGCATGCA CCTACTTCAA GTTCTACAAA G             51

(2) INFORMATION FOR SEQ ID NO:14:

(i) SEQUENCE CHARACTERISTICS:
                    (A) LENGTH: 42 base pairs
                    (B) TYPE: nucleic acid
                    (C) STRANDEDNESS: single (D) TOPOLOGY: linear (ii) MOLECULE TYPE: DNA (ix) FEATURE:
         (A) NAME/KEY: -
         (B) LOCATION: 1..42
         (D) OTHER INFORMATION: /note= "BK84 primer"

(xi) SEQUENCE DESCRIPTION: SEQ ID NO:14:

TCAAGCTGAA TTCTAGGTGA GTGTTGAGAT GATGCTTTGA CA          42

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: -
         (B) LOCATION: 1..21
         (D) OTHER INFORMATION: /note= "BK87 primer"

(xi) SEQUENCE DESCRIPTION: SEQ ID NO:15:

CGGCCACGAT GCGTCCGGCG T                                 21

(2) INFORMATION FOR SEQ ID NO:16:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: -
         (B) LOCATION: 1..57
         (D) OTHER INFORMATION: /note= "BK96 primer"

(xi) SEQUENCE DESCRIPTION: SEQ ID NO:16:

GGGCTTGGAT CCCCCCCCAC CTGAACCTCC TCCCCCGCTC GAACACTTTG AATATTT     57

(2) INFORMATION FOR SEQ ID NO:17:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: -
         (B) LOCATION: 1..60
         (D) OTHER INFORMATION: /note= "BK97 primer"

(xi) SEQUENCE DESCRIPTION: SEQ ID NO:17:

GAGGTCGGAT CCGGCGGAGG CGGATCTGGC GGAGGTGGCT CGGGCGGCAG CCTGGCCGCG    60

(2) INFORMATION FOR SEQ ID NO:18:

(i) SEQUENCE CHARACTERISTICS:
        (A) LENGTH: 42 base pairs
        (B) TYPE: nucleic acid
        (C) STRANDEDNESS: single (D) TOPOLOGY: linear (ii) MOLECULE TYPE: DNA (ix) FEATURE:
        (A) NAME/KEY: -
        (B) LOCATION: 1..42
        (D) OTHER INFORMATION: /note= "BK-110 primer"

(xi) SEQUENCE DESCRIPTION: SEQ ID NO:18:

TGTTGCTCCG GAGGTAACGG TGGGCACAAG TGCGATATCA CC          42

(2) INFORMATION FOR SEQ ID NO:19:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..45
        (D) OTHER INFORMATION: /note= "BK-111 primer"

(xi) SEQUENCE DESCRIPTION: SEQ ID NO:19:

CTTGTGCCCA CCGTTACCTC CGGACGAACA CTTTGAATAT TTCTC       45

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..33
        (D) OTHER INFORMATION: /note= "BK-112 primer"

(xi) SEQUENCE DESCRIPTION: SEQ ID NO:20:

CTCAGTTGAA GCTTTGGAGG CAGCAAAGAT GTC                    33

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..33
        (D) OTHER INFORMATION: /note= "BK-113 primer"

(xi) SEQUENCE DESCRIPTION: SEQ ID NO:21:

TTTGCTGCCC ATATGAACAC AACTGAGAAG GAA                    33

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: DNA (ix) FEATURE:
        (A) NAME/KEY: -
        (B) LOCATION: 1..30
        (D) OTHER INFORMATION: /note= "BK-114 primer"

(xi) SEQUENCE DESCRIPTION: SEQ ID NO:22:

ACTCTGGTAA GCTTCCTTCA CAGGACAGGA                                              30

(2) INFORMATION FOR SEQ ID NO:23:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..36
        (D) OTHER INFORMATION: /note= "BK-115 primer"

(xi) SEQUENCE DESCRIPTION: SEQ ID NO:23:

CCTGTGAAGC ATATGAACCA GAGTACGTTG GAAAAC                                       36

(2) INFORMATION FOR SEQ ID NO:24:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..33
        (D) OTHER INFORMATION: /note= "BK-116 primer"

(xi) SEQUENCE DESCRIPTION: SEQ ID NO:24:

TATTCAAAGT AAGCTTCCGG GGGAGGAGGT TCA                                          33

(2) INFORMATION FOR SEQ ID NO:25:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..33
        (D) OTHER INFORMATION: /note= "BK-117 primer"

(xi) SEQUENCE DESCRIPTION: SEQ ID NO:25:

GGAGATATAC ATATGGACAC AACTGAGAAG GAA                                          33

(2) INFORMATION FOR SEQ ID NO:26:

(i) SEQUENCE CHARACTERISTICS:
        (A) LENGTH: 48 base pairs
        (B) TYPE: nucleic acid
        (C) STRANDEDNESS: single (D) TOPOLOGY: linear (ii) MOLECULE TYPE: DNA (ix) FEATURE:
         (A) NAME/KEY: -
         (B) LOCATION: 1..48
         (D) OTHER INFORMATION: /note= "BK-132 primer"

(xi) SEQUENCE DESCRIPTION: SEQ ID NO:26:

GTTTAACTTT AAGCTTCCGG AGGTCCCGAG GACACAACTG AGAAGGAA                48

(2) INFORMATION FOR SEQ ID NO:27:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..36
         (D) OTHER INFORMATION: /note= "BK-133 primer"

(xi) SEQUENCE DESCRIPTION: SEQ ID NO:27:

CTCGGGACCT CGAGCTCATT TGGAGGCAGC AAAGAT                              36

(2) INFORMATION FOR SEQ ID NO:28:

(i) SEQUENCE CHARACTERISTICS:
         (A) LENGTH: 42 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..42
         (D) OTHER INFORMATION: /note= "BK-135 primer"

(xi) SEQUENCE DESCRIPTION: SEQ ID NO:28:

ACACTCACCG GAGGTAACGG TGGGGCACCT ACTTCAAGTT CT                       42

(2) INFORMATION FOR SEQ ID NO:29:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..36
         (D) OTHER INFORMATION: /note= "BK-136 primer"

(xi) SEQUENCE DESCRIPTION: SEQ ID NO:29:

AAACTGAATT CAAGCTTACC TGGTGAGTTT GGGATT                              36

(2) INFORMATION FOR SEQ ID NO:30:

(i) SEQUENCE CHARACTERISTICS:
         (A) LENGTH: 30 base pairs
         (B) TYPE: nucleic acid
         (C) STRANDEDNESS: single (D) TOPOLOGY: linear (ii) MOLECULE TYPE: DNA (ix) FEATURE:
        (A) NAME/KEY: -
        (B) LOCATION: 1..30
        (D) OTHER INFORMATION: /note= "BK-137 primer"

(xi) SEQUENCE DESCRIPTION: SEQ ID NO:30:

AAACTCACCC ATATGCTCAC ATTTAAGTTT                                           30

(2) INFORMATION FOR SEQ ID NO:31:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..39
        (D) OTHER INFORMATION: /note= "BK-138 primer"

(xi) SEQUENCE DESCRIPTION: SEQ ID NO:31:

AGGTGCCCCA CCGTTACCTC CGGTGAGTGT TGAGATGAT                                 39

(2) INFORMATION FOR SEQ ID NO:32:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..42
        (D) OTHER INFORMATION: /note= "BK-139 primer"

(xi) SEQUENCE DESCRIPTION: SEQ ID NO:32:

GAGGGCGGAG GAAACGGAGG TGGGGCACCC GCCCGCTCGC CC                             42

(2) INFORMATION FOR SEQ ID NO:33:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..36
        (D) OTHER INFORMATION: /note= "BK-140 primer"

(xi) SEQUENCE DESCRIPTION: SEQ ID NO:33:

TTCTAGAATT CAAGCTTACT CAGCAGCAGT GTCTCT                                    36

(2) INFORMATION FOR SEQ ID NO:34:

(i) SEQUENCE CHARACTERISTICS:
        (A) LENGTH: 33 base pairs
        (B) TYPE: nucleic acid
        (C) STRANDEDNESS: single

```
            (D) TOPOLOGY: linear (ii) MOLECULE TYPE: DNA (ix) FEATURE:
            (A) NAME/KEY: -
            (B) LOCATION: 1..33
            (D) OTHER INFORMATION: /note= "BK-141 primer"

(xi) SEQUENCE DESCRIPTION: SEQ ID NO:34:

ACTGCTGCTC ATATGGATGA AACAGTAGAA GTC                                    33

(2) INFORMATION FOR SEQ ID NO:35:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..45
            (D) OTHER INFORMATION: /note= "BK-142 primer"

(xi) SEQUENCE DESCRIPTION: SEQ ID NO:35:

GGGTGCCCCA CCTCCGTTTC CTCCGCCCTC CTGGACTGGC TCCCA                       45

(2) INFORMATION FOR SEQ ID NO:36:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..39
            (D) OTHER INFORMATION: /note= "BK-143 primer"

(xi) SEQUENCE DESCRIPTION: SEQ ID NO:36:

GCCTGCAGCC ATATGGCACC CGCCCGCTCG CCCAGCCCC                              39

(2) INFORMATION FOR SEQ ID NO:37:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..42
            (D) OTHER INFORMATION: /note= "BK-144 primer"

(xi) SEQUENCE DESCRIPTION: SEQ ID NO:37:

CTCATGAATT CAAGCTTACT CCTGGACTGG CTCCCAGCAG TC                          42

(2) INFORMATION FOR SEQ ID NO:38:

(i) SEQUENCE CHARACTERISTICS:
            (A) LENGTH: 33 base pairs
            (B) TYPE: nucleic acid
            (C) STRANDEDNESS: single
```

(D) TOPOLOGY: linear (ii) MOLECULE TYPE: DNA (ix) FEATURE:
            (A) NAME/KEY: -
            (B) LOCATION: 1..33
            (D) OTHER INFORMATION: /note= "BK-149 primer"

(xi) SEQUENCE DESCRIPTION: SEQ ID NO:38:

AATTCAAGCT TCACGTGTGA GTTTGGGATT CTT                                  33

(2) INFORMATION FOR SEQ ID NO:39:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..33
            (D) OTHER INFORMATION: /note= "BK-150 primer"

(xi) SEQUENCE DESCRIPTION: SEQ ID NO:39:

AATTCAAGAA GCTTCTGCAG CAGTGTCTCT ACT                                  33

(2) INFORMATION FOR SEQ ID NO:40:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..30
            (D) OTHER INFORMATION: /note= "BK-151 primer"

(xi) SEQUENCE DESCRIPTION: SEQ ID NO:40:

CTGTGCACCC ATATGACCGT AACAGACATC                                      30

(2) INFORMATION FOR SEQ ID NO:41:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..30
            (D) OTHER INFORMATION: /note= "BK-152 primer"

(xi) SEQUENCE DESCRIPTION: SEQ ID NO:41:

GATGTCGTAA GCTTTCAACT CGGTGCACAG                                      30

(2) INFORMATION FOR SEQ ID NO:42:

(i) SEQUENCE CHARACTERISTICS:
            (A) LENGTH: 36 base pairs
            (B) TYPE: nucleic acid
            (C) STRANDEDNESS: single (D) TOPOLOGY: linear (ii) MOLECULE TYPE: DNA (ix) FEATURE:
         (A) NAME/KEY: -
         (B) LOCATION: 1..36
         (D) OTHER INFORMATION: /note= "BK-153 primer"

(xi) SEQUENCE DESCRIPTION: SEQ ID NO:42:

ACAGTGCAGC ATATGACCCC CCTGGGCCCT GCCAGC                                    36

(2) INFORMATION FOR SEQ ID NO:43:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..33
         (D) OTHER INFORMATION: /note= "BK-154 primer"

(xi) SEQUENCE DESCRIPTION: SEQ ID NO:43:

AATCTAAGCT TGGGGCTGGG CAAGGTGGCG TAG                                       33

(2) INFORMATION FOR SEQ ID NO:44:

(i) SEQUENCE CHARACTERISTICS:
         (A) LENGTH: 42 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..42
         (D) OTHER INFORMATION: /note= "BK-155 primer"

(xi) SEQUENCE DESCRIPTION: SEQ ID NO:44:

GGGGGCGGAG GAAACGGAGG TGGGACCCCC CTGGGCCCTG CC                             42

(2) INFORMATION FOR SEQ ID NO:45:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..27
         (D) OTHER INFORMATION: /note= "BK-156 primer"

(xi) SEQUENCE DESCRIPTION: SEQ ID NO:45:

CTGCAAAGCT TGGCTGGGGC AGCTGCT                                              27

(2) INFORMATION FOR SEQ ID NO:46:

(i) SEQUENCE CHARACTERISTICS:
         (A) LENGTH: 33 base pairs
         (B) TYPE: nucleic acid
         (C) STRANDEDNESS: single (D) TOPOLOGY: linear (ii) MOLECULE TYPE: DNA (ix) FEATURE:
                (A) NAME/KEY: -
                (B) LOCATION: 1..33
                (D) OTHER INFORMATION: /note= "BK-157 primer"

(xi) SEQUENCE DESCRIPTION: SEQ ID NO:46:

TGCCCCAGCC ATATGCTGCA GCTGGCAGGC TGC                                  33

(2) INFORMATION FOR SEQ ID NO:47:

(i) SEQUENCE CHARACTERISTICS:
                (A) LENGTH: 42 base pairs
                (B) TYPE: nucleic acid
                (C) STRANDEDNESS: single
                (D) TOPOLOGY: linear (ii) MOLECULE TYPE: DNA (ix) FEATURE:
                (A) NAME/KEY: -
                (B) LOCATION: 1..42
                (D) OTHER INFORMATION: /note= "BK-158 primer"

(xi) SEQUENCE DESCRIPTION: SEQ ID NO:47:

GGTCCCACCT CCGTTTCCTC CGCCGGGCTG GGCAAGGTGG CG                        42

(2) INFORMATION FOR SEQ ID NO:48:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: DNA (ix) FEATURE:
                (A) NAME/KEY: -
                (B) LOCATION: 1..21
                (D) OTHER INFORMATION: /note= "VK116 primer"

(xi) SEQUENCE DESCRIPTION: SEQ ID NO:48:

TGGCGCGGTT TCTATATCGC C                                               21

(2) INFORMATION FOR SEQ ID NO:49:

(i) SEQUENCE CHARACTERISTICS:
                (A) LENGTH: 48 base pairs
                (B) TYPE: nucleic acid
                (C) STRANDEDNESS: single
                (D) TOPOLOGY: linear (ii) MOLECULE TYPE: DNA (ix) FEATURE:
                (A) NAME/KEY: -
                (B) LOCATION: 1..48
                (D) OTHER INFORMATION: /note= "VK281 primer"

(xi) SEQUENCE DESCRIPTION: SEQ ID NO:49:

GGCCGGTCGC GGGAATTCTT AGAGCTCGTC TTTCGGCGGT TGCCGGG                   48

(2) INFORMATION FOR SEQ ID NO:50:

(i) SEQUENCE CHARACTERISTICS:
                (A) LENGTH: 5 amino acids
                (B) TYPE: amino acid
                (C) STRANDEDNESS:

(D) TOPOLOGY: linear (ii) MOLECULE TYPE: peptide (xi) SEQUENCE DESCRIPTION: SEQ ID NO:50:

Gly Gly Asn Gly Gly
1               5

(2) INFORMATION FOR SEQ ID NO:51:

(i) SEQUENCE CHARACTERISTICS:
          (A) LENGTH: 5 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:51:

Ser Gly Gly Pro Glu
1               5

(2) INFORMATION FOR SEQ ID NO:52:

(i) SEQUENCE CHARACTERISTICS:
          (A) LENGTH: 7 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:52:

Gly Gly Gly Asn Gly Gly Gly
1               5

(2) INFORMATION FOR SEQ ID NO:53:

(i) SEQUENCE CHARACTERISTICS:
          (A) LENGTH: 6 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:53:

Arg Pro His Met Ala Asp
1               5

(2) INFORMATION FOR SEQ ID NO:54:

(i) SEQUENCE CHARACTERISTICS:
          (A) LENGTH: 5 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:54:

Gly Gly Gly Gly Ser
1               5

(2) INFORMATION FOR SEQ ID NO:55:

(i) SEQUENCE CHARACTERISTICS:
          (A) LENGTH: 20 amino acids
          (B) TYPE: amino acid
          (C) STRANDEDNESS:

```
            (D) TOPOLOGY: linear (ii) MOLECULE TYPE: peptide (xi) SEQUENCE DESCRIPTION: SEQ ID NO:55:

Gly Gly Gly Gly Ser Gly Gly Gly Ser Gly Gly Gly Ser Gly
1               5                   10                  15

Gly Gly Gly Ser
            20

(2) INFORMATION FOR SEQ ID NO:56:

(i) SEQUENCE CHARACTERISTICS:
            (A) LENGTH: 22 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:56:

Ala Ser Gly Gly Gly Gly Ser Gly Gly Gly Ser Gly Gly Gly Gly
1               5                   10                  15

Ser Gly Gly Gly Gly Ser
            20

(2) INFORMATION FOR SEQ ID NO:57:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:57:

Ala Ser Gly Gly Pro Glu
1               5

(2) INFORMATION FOR SEQ ID NO:58:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..21
            (D) OTHER INFORMATION: /note= "BK64 primer"

(xi) SEQUENCE DESCRIPTION: SEQ ID NO:58:

AGGGGTTATG CTAGTTATTG C                                                 21

(2) INFORMATION FOR SEQ ID NO:59:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:59:
```

Arg Glu Asp Leu Lys
1               5

(2) INFORMATION FOR SEQ ID NO:60:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:60:

Arg Glu Asp Leu
1

(2) INFORMATION FOR SEQ ID NO:61:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:61:

Arg Asp Glu Leu
1

(2) INFORMATION FOR SEQ ID NO:62:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:62:

Lys Asp Glu Leu
1

(2) INFORMATION FOR SEQ ID NO:63:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:63:

Met Asn Thr Thr Glu
1               5

(2) INFORMATION FOR SEQ ID NO:64:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:64:

―continued

```
Met Asp Thr Thr Glu
1               5
```

(2) INFORMATION FOR SEQ ID NO:65:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:65:

```
Arg Glu Asp Leu Arg
1               5
```

(2) INFORMATION FOR SEQ ID NO:66:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:66:

```
His Lys Cys Asp Ile Thr Leu Gln
1               5
```

(2) INFORMATION FOR SEQ ID NO:67:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:67:

```
Asn Thr Thr Glu Lys Glu Thr Phe
1               5
```

(2) INFORMATION FOR SEQ ID NO:68:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:68:

```
His Lys Asn Thr Thr Glu Lys Glu Thr Phe
1               5                   10
```

(2) INFORMATION FOR SEQ ID NO:69:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:69:

```
Asp Thr Thr Glu Lys Glu Thr Phe
1               5
```

(2) INFORMATION FOR SEQ ID NO:70:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..36
        (D) OTHER INFORMATION: /note= "BK11B primer"

(xi) SEQUENCE DESCRIPTION: SEQ ID NO:70:

TAAGAAGGAC ATATGCATAA GAACACAACT GAGAAG      36

(2) INFORMATION FOR SEQ ID NO:71:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:71:

```
Met His Lys Cys Asp
1               5
```

(2) INFORMATION FOR SEQ ID NO:72:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:72:

```
Met His Lys Asn Thr Thr
1               5
```